US009452274B2

(12) United States Patent
Addington et al.

(10) Patent No.: US 9,452,274 B2
(45) Date of Patent: Sep. 27, 2016

(54) METERED DOSE ATOMIZER

(71) Applicant: PNEUMOFLEX SYSTEMS, LLC, Melbourne, FL (US)

(72) Inventors: W. Robert Addington, Melbourne Beach, FL (US); Stuart P. Miller, Indialantic, FL (US)

(73) Assignee: Pneumoflex Systems, LLC, Melbourne, FL (US)

( * ) Notice: Subject to any disclaimer, the term of this patent is extended or adjusted under 35 U.S.C. 154(b) by 0 days.

(21) Appl. No.: 14/166,903

(22) Filed: Jan. 29, 2014

(65) Prior Publication Data

US 2014/0202458 A1    Jul. 24, 2014

Related U.S. Application Data

(63) Continuation-in-part of application No. 13/799,196, filed on Mar. 13, 2013, now abandoned, which is a continuation-in-part of application No. 13/353,611, filed on Jan. 19, 2012, now Pat. No. 8,671,934.

(60) Provisional application No. 61/434,613, filed on Jan. 20, 2011.

(51) Int. Cl.
*A61M 11/00* (2006.01)
*A61M 11/02* (2006.01)
(Continued)

(52) U.S. Cl.
CPC ............ *A61M 16/14* (2013.01); *A61B 5/087* (2013.01); *A61B 5/0823* (2013.01); *A61B 5/097* (2013.01); *A61B 5/4839* (2013.01);
(Continued)

(58) Field of Classification Search
CPC .... A61M 11/00; A61M 11/02; A61M 11/08; A61M 11/06; A61M 15/0086; A61M 16/14; A61M 2205/8225; A61M 2206/14; A61J 17/006
USPC ............. 239/338, 370; 261/78.1; 128/200.21
See application file for complete search history.

(56) References Cited

U.S. PATENT DOCUMENTS 75,991 A * 3/1868 Shurtleff .................. 128/200.22
341,712 A   5/1886 Wilson
(Continued)

FOREIGN PATENT DOCUMENTS

EP   0667168     2/1994
WO  2011006184   1/2011

OTHER PUBLICATIONS

Joseph L. Rau, 2004 Philip Kittredge Memorial Lecture, the Inhalation of Drugs: Advantages and Problems, Respiratory Care, Mar. 2005, vol. 50, No. 3, pp. 367-382.

(Continued)

*Primary Examiner* — Peter S Vasat
(74) *Attorney, Agent, or Firm* — Allen, Dyer, Doppelt, Milbrath & Gilchrist, P.A.

(57) ABSTRACT

An atomizer has a venturi nozzle positioned at an outlet end of an air line and has a discharge end and is oriented horizontally when in use and forms a mixing chamber at its discharge end. A valve is positioned at a canister port and actuable to allow a metered flow of gas at a predetermined pressure and time through the air line and venturi nozzle. A suction line extends from the venturi nozzle and mixing chamber to a medication receiver and draws medication upward and mixes it with gas passing through the venturi nozzle into the mixing chamber and atomizes the medication into a mist.

10 Claims, 51 Drawing Sheets

(51) Int. Cl.
*A61M 16/14* (2006.01)
*A61M 15/00* (2006.01)
*A61B 5/08* (2006.01)
*A61B 5/087* (2006.01)
*A61B 5/097* (2006.01)
*A61B 5/00* (2006.01)
*A61J 17/00* (2006.01)
*A61M 11/06* (2006.01)
*A61M 16/20* (2006.01)
*A61M 16/00* (2006.01)

(52) U.S. Cl.
CPC ........... *A61B 5/7282* (2013.01); *A61J 17/00* (2013.01); *A61M 11/06* (2013.01); *A61M 15/0036* (2014.02); *A61M 15/0086* (2013.01); *A61M 15/0091* (2013.01); *A61M 16/201* (2014.02); *A61M 15/0021* (2014.02); *A61M 2016/0027* (2013.01); *A61M 2016/0039* (2013.01); *A61M 2205/13* (2013.01); *A61M 2205/3569* (2013.01); *A61M 2205/3592* (2013.01); *A61M 2205/502* (2013.01); *A61M 2205/8225* (2013.01); *A61M 2206/14* (2013.01)

(56) References Cited

U.S. PATENT DOCUMENTS

| | | |
|---|---|---|
| 2,280,050 A | 4/1942 | Alexander et al. |
| 3,097,645 A | 7/1963 | Lester |
| 3,104,062 A * | 9/1963 | Mahon .......... 239/338 |
| 3,888,253 A | 6/1975 | Watt et al. |
| 3,998,226 A | 12/1976 | Harris |
| 4,150,071 A * | 4/1979 | Pecina .......... 261/78.2 |
| 4,253,468 A | 3/1981 | Lehmbeck |
| 4,318,397 A | 3/1982 | Kobayashi |
| 4,333,450 A | 6/1982 | Lester |
| 4,792,097 A | 12/1988 | Kremer, Jr. et al. |
| 4,809,706 A | 3/1989 | Watson et al. |
| 4,852,582 A | 8/1989 | Pell |
| 4,884,460 A | 12/1989 | Nowacki et al. |
| 4,951,661 A | 8/1990 | Sladek |
| RE33,717 E | 10/1991 | Svoboda |
| 5,186,166 A | 2/1993 | Riggs et al. |
| 5,301,666 A | 4/1994 | Lerk et al. |
| 5,312,046 A | 5/1994 | Knoch et al. |
| 5,411,208 A | 5/1995 | Burgener |
| 5,598,838 A | 2/1997 | Servidio et al. |
| 5,649,530 A | 7/1997 | Ballini |
| 5,666,946 A | 9/1997 | Langenback |
| 5,676,132 A | 10/1997 | Tillotson et al. |
| 5,678,563 A | 10/1997 | Addington et al. |
| 5,685,291 A | 11/1997 | Marsh |
| 5,823,187 A | 10/1998 | Estes et al. |
| 5,839,430 A | 11/1998 | Cama |
| 5,904,140 A | 5/1999 | McGoogan |
| 6,004,268 A | 12/1999 | Addington et al. |
| 6,029,660 A | 2/2000 | Calluaud et al. |
| 6,044,841 A | 4/2000 | Verdun et al. |
| 6,050,953 A | 4/2000 | Warwick et al. |
| 6,085,741 A | 7/2000 | Becker |
| 6,183,423 B1 | 2/2001 | Gaumond et al. |
| 6,223,745 B1 | 5/2001 | Hammarlund et al. |
| 6,267,006 B1 | 7/2001 | Bugli et al. |
| 6,328,030 B1 | 12/2001 | Kidwell et al. |
| 6,398,728 B1 | 6/2002 | Bardy |
| 6,411,843 B1 | 6/2002 | Zarychta |
| 6,568,387 B2 | 5/2003 | Davenport et al. |
| 6,598,602 B1 | 7/2003 | Sjoholm |
| 6,615,826 B1 | 9/2003 | Gabrio et al. |
| 6,655,376 B2 | 12/2003 | Addington et al. |
| 6,679,250 B2 | 1/2004 | Walker et al. |
| 6,698,422 B2 | 3/2004 | Fugelsang et al. |
| 6,729,327 B2 | 5/2004 | McFarland |
| 6,735,471 B2 | 5/2004 | Hill et al. |
| 6,805,118 B2 * | 10/2004 | Brooker et al. .......... 128/203.12 |
| 6,848,443 B2 | 2/2005 | Schmidt et al. |
| 7,013,894 B2 | 3/2006 | McFarland |
| 7,080,643 B2 | 7/2006 | Grychowski et al. |
| 7,191,780 B2 | 3/2007 | Faram |
| 7,264,179 B2 | 9/2007 | Robbins |
| 7,270,123 B2 | 9/2007 | Grychowski et al. |
| 7,290,541 B2 | 11/2007 | Irvi et al. |
| 7,322,349 B2 | 1/2008 | Power |
| 7,568,480 B2 | 8/2009 | Foley et al. |
| 7,614,280 B1 | 11/2009 | Gardner et al. |
| 7,634,995 B2 | 12/2009 | Grychowski et al. |
| 7,712,466 B2 | 5/2010 | Addington et al. |
| 7,721,729 B2 | 5/2010 | Von Hollen et al. |
| 7,726,306 B2 | 6/2010 | Addington et al. |
| 7,841,335 B2 | 11/2010 | Harrington et al. |
| 7,841,336 B2 | 11/2010 | Rivera et al. |
| 7,870,857 B2 | 1/2011 | Dhuper et al. |
| 7,971,588 B2 | 7/2011 | Fink et al. |
| 8,109,266 B2 | 2/2012 | Addington et al. |
| 8,245,708 B2 | 8/2012 | Smaldone et al. |
| 8,371,299 B2 | 2/2013 | Denyer et al. |
| 8,408,200 B2 | 4/2013 | Clark et al. |
| 8,597,184 B2 | 12/2013 | Addington et al. |
| 8,671,934 B2 | 3/2014 | Addington et al. |
| 2001/0050086 A1 | 12/2001 | Addington et al. |
| 2002/0121275 A1 | 9/2002 | Johnson et al. |
| 2003/0079742 A1 | 5/2003 | Giroux |
| 2003/0121517 A1 | 7/2003 | McFarland |
| 2003/0136399 A1 | 7/2003 | Foley et al. |
| 2003/0205229 A1 | 11/2003 | Crockford et al. |
| 2004/0172010 A1 | 9/2004 | Addington et al. |
| 2004/0181161 A1 | 9/2004 | Addington et al. |
| 2004/0187864 A1 | 9/2004 | Adams |
| 2004/0206351 A1 | 10/2004 | McFarland, Jr. |
| 2005/0081844 A1 | 4/2005 | Grychowski et al. |
| 2007/0135736 A1 | 6/2007 | Addington et al. |
| 2007/0137648 A1 | 6/2007 | Addington et al. |
| 2007/0163572 A1 | 7/2007 | Addington et al. |
| 2007/0255090 A1 | 11/2007 | Addington et al. |
| 2008/0004540 A1 | 1/2008 | Nakao et al. |
| 2008/0283049 A1 * | 11/2008 | Mahoney et al. ....... 128/200.14 |
| 2009/0025718 A1 | 1/2009 | Denyer et al. |
| 2009/0050141 A1 | 2/2009 | King et al. |
| 2009/0062855 A1 | 3/2009 | Lemery et al. |
| 2010/0137736 A1 | 6/2010 | Addington et al. |
| 2010/0137737 A1 | 6/2010 | Addington et al. |
| 2010/0147298 A1 | 6/2010 | Loescher et al. |
| 2010/0204602 A1 | 8/2010 | Addington et al. |
| 2011/0040157 A1 | 2/2011 | Addington et al. |
| 2011/0040211 A1 | 2/2011 | Addington et al. |
| 2011/0046653 A1 | 2/2011 | Addington et al. |
| 2012/0053482 A1 | 3/2012 | Addington et al. |
| 2012/0145153 A1 | 6/2012 | Bassin et al. |
| 2012/0186582 A1 | 7/2012 | Addington et al. |
| 2012/0190999 A1 | 7/2012 | Addington et al. |
| 2013/0081617 A1 | 4/2013 | Cavendish |
| 2013/0192594 A1 | 8/2013 | Addington et al. |

OTHER PUBLICATIONS

Cates et al., "Holding Chambers Versus Nebulisers for Inhaled Steroids in Chronic Asthma (Review)," The Cochrane Collaboration, the Cochrane Database of Systematic Reviews 2006, Issue 1, pub 2, DOI: 10.1002/14651858, CD001491, pub 2, 23 pages.

Lasserson et al. "Differences in Motor Activation of Voluntary and Reflex Cough in Humans" PubMed: Thorax. Aug. 2006; 61(8): 699-705.

"Battle of the MDI an DPI Patent Trends" Sep. 27, 2009; pp. 1-7: http://www.inhalationreport.com/2009/09/27/battle-of-the-mdi-and-dpi-patent-trends.

"Inhaler 2.0—What's the Future of Inhalation Devices?" Jan. 25, 2010; 2 pgs. http://www.inhalationreport.com/2010/01/25/inhaler-2-0-whats-the-future-of-inhalation-devices/.

Adi et al. "Co-deposition of a triple therapy drug formulation for the treatment of chronic obstructive pulmonary disease using solution-

(56) References Cited

OTHER PUBLICATIONS based pressurised metered dose inhalers" J. Pharm Pharmacol. Sep. 2012; 64(9) 1245-53. (Abstract Only).

Coleman et al. "Therapeutic aerosol delivery during mechanical ventilation" http://www.ncbi.nlm.nih.gov/pubmed/8792952?report=abstract: Printed Jul. 2, 2013: (Abstract Only).

Berlinski et al. "Albuteral delivery by 4 different nebulizers placed in 4 different positions in a pediatric ventilator in vitro model" Respiratory Care: Jul. 2013; vol. 58, No. 7. pp. 1124-1133.

Ari et al. "Evaluation of aerosol generator devices at 3 locations in humidified and non-humidified circuits during adult mechanical ventilation" Respiratory Care: Jul. 2010; vol. 55, No. 7, pp. 837-844.

Leung et al., "Comparison of breath-enhanced to breath-actuated nebulizers for rate, consistency, and efficiently*" http://jounal.publications.chestnet.org/article.aspl?articleid=1082940: printed Jul. 3, 2010; pp. 1-10.

Barlow et al. "Frequency Modulation and Spatiotemporal Stability of the sCPC in Preterm Infants with RDS" Hindawi Publishing Corp. International Journal of Pediatrics: vol. 2012, Article ID 581538; 9 pgs. May 29, 2012.

Doherty et al. "Nebuliser Therapy in the Intensive Care Unit" Thorax 1997;52(Supp12) pp. S56-S59.

Sakalidis et al. "Oxygen saturation and suck-swallow-breathe coordination of term infants during breastfeeding and feeding from a teat releasing mil only with vacuum" International Journal of Pediatrics; vol. 2012, article ID 130769, 10 pgs. accepted date Apr. 25, 2012.

Tomori et al. "Reversal of functional disorders by aspiration, expiration, and cough reflexes and their voluntary counterparts" www.frontiersin.org; Dec. 2012; vol. 3, article 467, 14 pgs.

Uldry et al. "Maximal values of sniff nasal inspiratory pressure in healthy subjects" thorax.bmj.com 1995;50: pp. 371-375 printed Apr. 16, 2014.

Amirav et al. "Lung aerosol deposition in suckling infants" Arch Dis Child 2012;97: pp. 497-501; printed May 19, 2012.

Patel et al. "Recovery from poststroke urinary incontinence: associated factors and impact on outcome" J Am Geriatr Soc. Sep. 2001;49(9) Abstract only.

Bean et al. "Influence of poststroke urinary incontinence on disability: the nursing home setting" Am J Phys Med Rehabil. Mar. 2003; 82(3) Abstract only.

Heritier et al. "Sniff nasal inspiratory pressure. A noninvasive assessment of inspiratory muscle strength" www.atsjournals.org/doi/abs/10.1164/ajrccm.150.6.7952632?journalcode=ajrccm; printed Oct. 1, 2013 Abstract only.

* cited by examiner

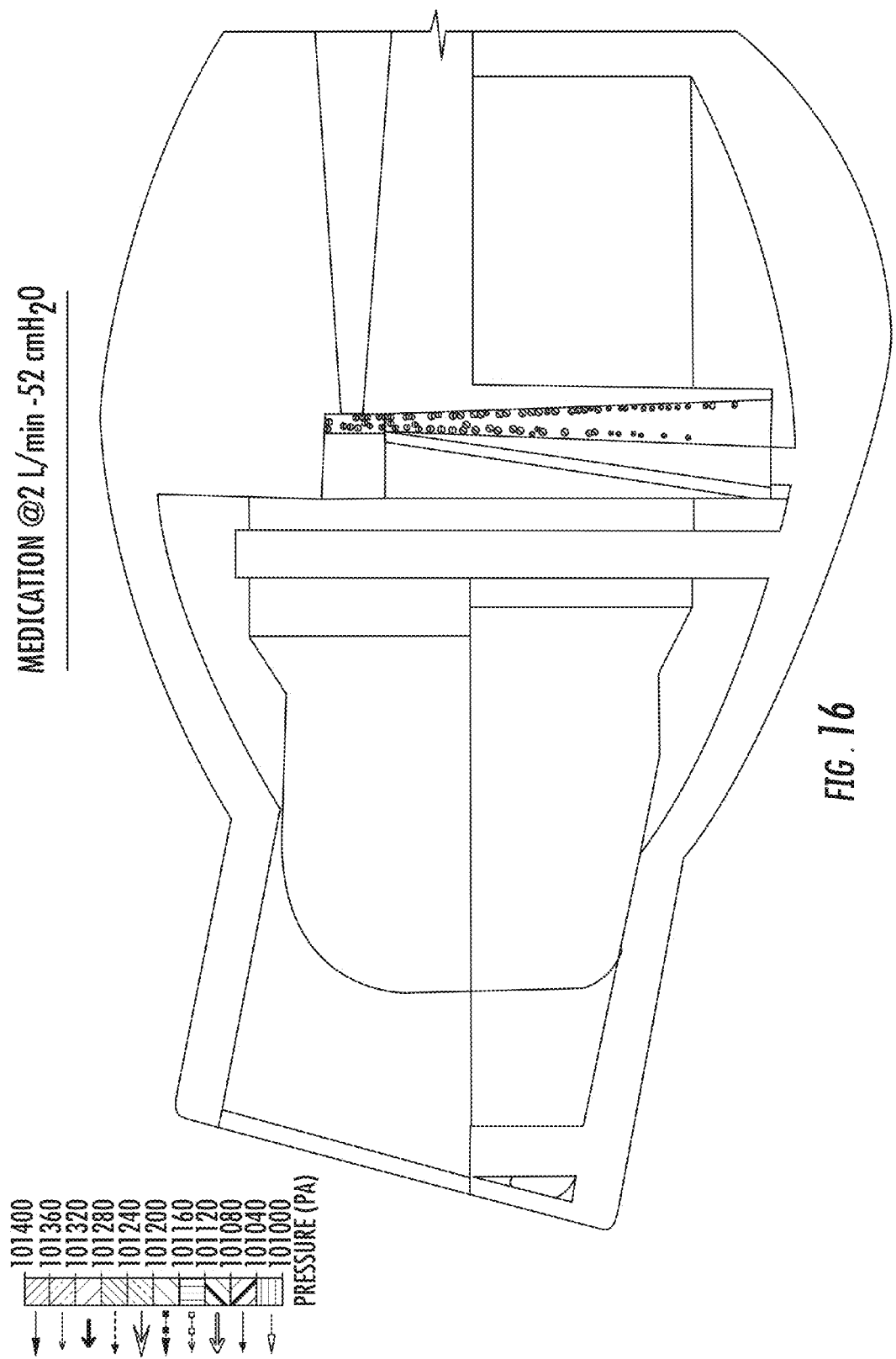

RESPIRATORY PRESSURES

TABLE 2- MEASURED AND PREDICTED MIP AND MEP FOR MALES AND FEMALES

| AGE BRACKET | MIP, cmH$_2$O | | MEP, cmH$_2$O | |
|---|---|---|---|---|
| YEARS | MEASURED | PREDICTED | MEASURED | PREDICTED |
| MEN | | | | |
| 20-29 | -113.5 ± 18.11 | -136.72 ± 2.53 * | 148 ± 29.46 | 146.43 ± 2.65 |
| 30-39 | -120 ± 16.16 | -129.14 ± 1.81 * | 135.5 ± 31.92 | 138.81 ± 1.83 |
| 40-49 | -100.42 ± 16.44 | -119.97 ± 2.38 * | 127.08 ± 19.59 | 129.53 ± 2.41 |
| 50-59 | -86 ± 26.23 | -114.46 ± 10.85 * | 112.5 ± 27.21 | 120.91 ± 2.75 |
| 60-69 | -85.00 ± 22.61 | -104.34 ± 2.10 * | 104.00 ± 22.09 | 113.70 ± 2.13 |
| 70-80 | -53 ± 19.18 | -93.7 ± 2.23 * | 74.5 ± 22.79 | 102.93 ± 2.26 |
| WOMEN | | | | |
| 20-29 | -80.50 ± 20.06 | -99.42 ± 1.25 * | 100.00 ± 18.41 | 101.94 ± 1.55 |
| 30-39 | -82.5 ± 22.88 | -93.64 ± 1.69 * | 94 ± 17.61 | 95.29 ± 1.77 |
| 40-49 | -78.6 ± 20.94 | -88.50 ± 1.44 * | 105.5 ± 25.54 | 88.27 ± 1.70 |
| 50-59 | -69 ± 19.41 | -83.84 ± 1.61 * | 88.5 ± 21.35 | 82.54 ± 2.01 |
| 60-69 | -63.5 ± 13.55 | -78.70 ± 1.88 * | 71 ± 9.07 | 76.13 ± 2.34 |
| 70-80 | -52 ± 11.83 | -73.31 ± 1.55 * | 66.5 ± 14.15 | 69.42 ± 1.93 |

* VALUES EXPRESSED AS MEAN ± SD; EACH AGE BRACKET COMPRISED 10 SUBJECTS. * P ≤ 0.05 VS MEASURED VALUES FROM THE CORRESPONDING AGE BRACKET (SHAPIRO-WILK TEST; STUDENT T-TEST;WILCOXON TEST).

FIG. 17

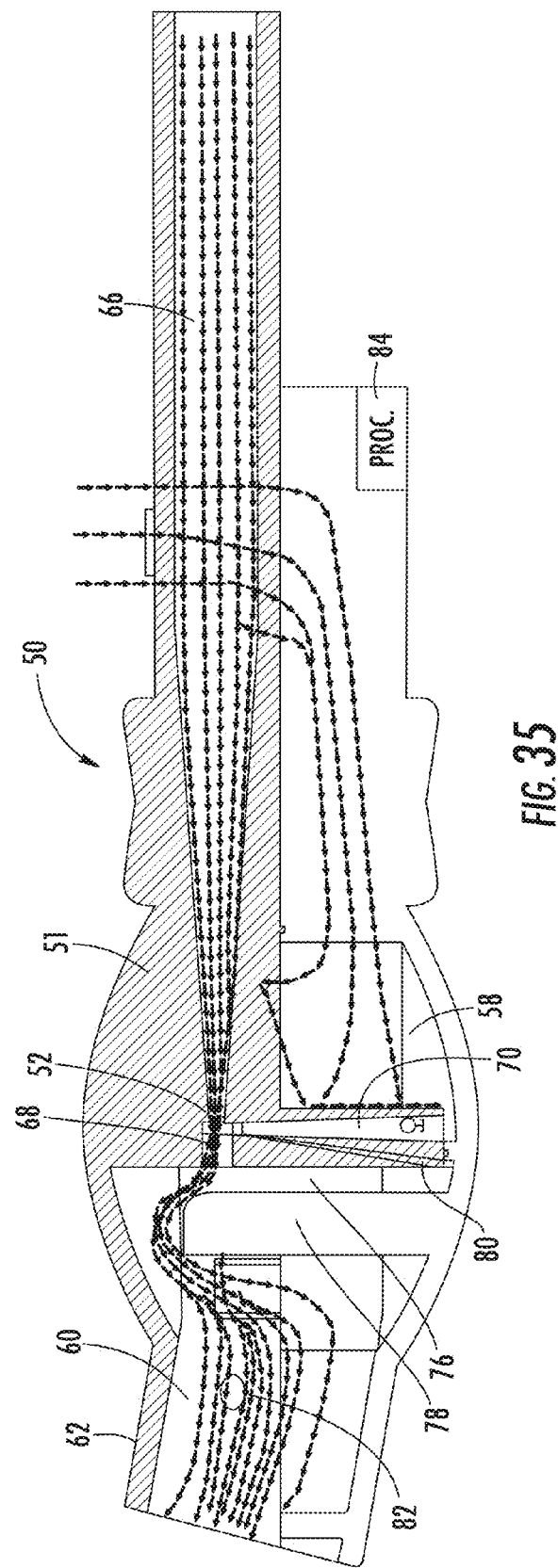

FIG. 40

TOTAL DELIVERED DRUG RESULTS

| TRIAL | DEVICE | FEED PRESSURE (psi) | PULSE DURATION (sec) | DRUG | DOSE | # OF ACTUATIONS | TOTAL DRUG RECOVERY (ug) | DRUG PER ACC (ug) |
|---|---|---|---|---|---|---|---|---|
| 1 | PNEUMOFLEXION | 7.2* | 0.5 | ALBUTEROL SULFATE (2.5mg/2.5ml) | 0.5ml | 20 | 10.279 | 0.514 |
| 2 | PNEUMOFLEXION | 7.2* | 1.0 | ALBUTEROL SULFATE (2.5mg/2.5ml) | 0.5ml | 10 | 13.566 | 1.357 |
| 3 | PNEUMOFLEXION | 7.2* | 2.0 | ALBUTEROL SULFATE (2.5mg/2.5ml) | 0.5ml | 10 | 21.240 | 2.124 |
| 4 | PNEUMOFLEXION | 15.5** | 0.5 | ALBUTEROL SULFATE (2.5mg/2.5ml) | 0.5ml | 20 | 38.344 | 1.917 |
| 5 | PNEUMOFLEXION | 15.5** | 1.0 | ALBUTEROL SULFATE (2.5mg/2.5ml) | 0.5ml | 10 | 37.487 | 3.749 |
| 6 | PNEUMOFLEXION | 15.5** | 2.0 | ALBUTEROL SULFATE (2.5mg/2.5ml) | 0.5ml | 10 | 60.041 | 6.004 |

\* EQUIVALENT TO PRESSURE AT A STEADY STATE FLOW OF 2 lpm
\** EQUIVALENT TO PRESSURE AT A STEADY STATE FLOW OF 3 lpm

FIG. 45B

METERED DOSE ATOMIZER

PRIORITY APPLICATION(S)

This application is a continuation-in-part application of application Ser. No. 13/799,196 filed Mar. 13, 2013, which is a continuation-in-part application of Ser. No. 13/353,611 filed Jan. 19, 2012, which claims priority to U.S. provisional application Ser. No. 61/434,613 filed Jan. 20, 2011, the disclosures which are hereby incorporated herein by reference in their entirety.

FIELD OF THE INVENTION

The present invention relates to the field of nebulizers, and more particularly, this invention relates to nebulizers having a venturi.

BACKGROUND OF THE INVENTION

Inhalation is a very old method of drug delivery. In the twentieth century it became a mainstay of respiratory care and was known as aerosol therapy. Use of inhaled epinephrine for relief of asthma was reported as early as 1929, in England. Dry powder inhalers have been used to administer penicillin dust to treat respiratory infections. In 1956, the first metered dosed inhaler was approved for clinical use.

The scientific basis for aerosol therapy developed relatively late, following the 1974 Sugar Loaf conference on the scientific basis of respiratory therapy. A more complete history of the development of aerosol therapy and the modern nebulizer is described in the 2004 Phillip Kitridge Memorial Lecture entitled, "The Inhalation of Drugs: Advantages and Problems by Joseph L. Row; printed in the March 2005 issue of Respiratory Care, vol. 50, no. 3.

Table 8 of the Respiratory Care article, referred to above, page 381, lists the characteristics of an ideal aerosol inhaler as follows:

TABLE 8

Dose reliability and reproducibility
High lung-deposition efficiency (target lung deposition of 100% of nominal dose)
Production of the fine particles ≤5 μm diameter, with correspondingly low mass median diameter
Simple to use and handle
Short treatment time
Small size and easy to carry
Multiple-dose capability
Resistance to bacterial contamination
Durable
Cost-effective
No drug released to ambient-air
Efficient (small particle size, high lung deposition) for the specific drug being aerosolized
Liked by patients and health care personnel Standard nebulizers typically fail to achieve a number of these characteristics because they waste medication during exhalation. Further, the particle size is often too large to reach the bottom of the lungs where the medication may be most needed. There is difficulty in estimating the dose of the drug being given to a patient and there is difficulty in reproducing that dose. There is a possibility of contamination when opening the initially sterile kit, pouring medication into the cup, and assembling the pieces for use by a patient. There is also considerable inefficiency in the medication delivery, with much of it being deposited in the throat, rather than in the lungs.

Commonly assigned U.S. Pat. No. 8,109,266, the disclosure which is hereby incorporated by reference in its entirety, discloses a nebulizer having a flow meter function that is applied to venturi type intra-oral nebulizers as disclosed in commonly assigned U.S. Pat. Nos. 7,712,466 and 7,726,306, the disclosures which are hereby incorporated by reference in their entirety. These nebulizers are horizontally configured, and in one example, include a venturi at a rainfall chamber. Further enhancements to the nebulizers are desirable.

SUMMARY OF THE INVENTION

An atomizer includes an atomizer body that has an air channel section and atomizer outlet. An air line extends through the air channel section and has an inlet and an outlet. A venturi nozzle is positioned at the outlet end of the air line and has a discharge end and is oriented horizontally when in use and forms a mixing chamber at its discharge end. A canister port is located at the inlet end of the air line and receives a gas canister. A valve is positioned at the canister port and actuable to allow a metered flow of gas at a predetermined pressure and time to flow from the gas canister and through the air line and venturi nozzle. A medication receiver is carried by the atomizer body proximal to the venturi nozzle and mixing chamber. A suction line extends from the venturi nozzle and mixing chamber to the medication receiver and draws medication upward from a medication container received within the medication receiver and mixes it with gas passing through the venturi nozzle into the mixing chamber and atomizes the medication into a mist.

In one example, the valve is actuated to deliver gas when pressure is applied downward on the gas canister. In another example, a medication container is received within the medication receiver and the suction line connects into the medication container. The valve actuates a pulsed and metered flow of gas during atomization. In another example, the atomizer outlet includes a flared extension and a diffuser is formed upon which the gas that is mixed with medication in the mixing chamber impacts to aid in forming the mist.

In another example, the atomizer body is substantially L-shaped and forms a vertical portion and a horizontal portion. The venturi nozzle is formed within the horizontal portion of the atomizer and the canister port is carried within the vertical portion of the atomizer body and receives the gas canister in one example in a vertical orientation. A medication receiver is carried in the horizontal portion of the atomizer body proximal to the venturi nozzle and mixing chamber.

In another example, the venturi nozzle, mixing chamber and suction line are formed together and replaceable as one unit and supported by the medication receiver. The suction line extends through the top support surface of the medication receiver and connects into the medication container received within the medication receiver. The suction line includes a flange that is seated on the top support surface of the medication receiver to support the venturi nozzle, mixing chamber and suction line in position within the atomizer body.

BRIEF DESCRIPTION OF THE DRAWINGS

Other objects, features and advantages of the present invention will become apparent from the detailed description of the invention which follows, when considered in light of the accompanying drawings in which:

FIG. 16 is a sectional view of the nebulizer of FIG. 1 showing the medication flow upward at 2 L/min −52 $cmH_2O$.

FIG. 17 is a table showing respiratory pressures for the measured and predicted MIP and MEP for males and females.

FIG. 35 is a partial, sectional view of the nebulizer of FIG. 2B in accordance with a non-limiting example.

FIG. 38 shows a nebulizer testing set-up used to test the nebulizer in accordance with a non-limiting example for particle size distribution and determine a change in nebulizer MMAD (Mass Median Aerodynamic Diameter) during nebulization.

FIG. 39 is a graph showing a particle size distribution by mass for different flow rates of the nebulizer such as described in the test of FIG. 38 in accordance with a non-limiting example.

FIG. 40 is another graph showing particle size distribution by mass for the nebulizer similar as described in the test of FIG. 38 in accordance with a non-limiting example, but a smaller diameter feed orifice as compared to the nebulizer example of FIG. 39.

FIG. 41 is a graph showing the change in nebulizer MMAD during nebulization as described in the test of FIG. 38.

FIG. 42 shows a nebulizer testing set-up for evaluating the nebulizer in accordance with a non-limiting example under pulsed conditions.

FIG. 43 is a graph showing the average peak particle size distribution for different trials under different pulsed conditions as described in the test of FIG. 42 in accordance with a non-limiting example.

Figure 42:
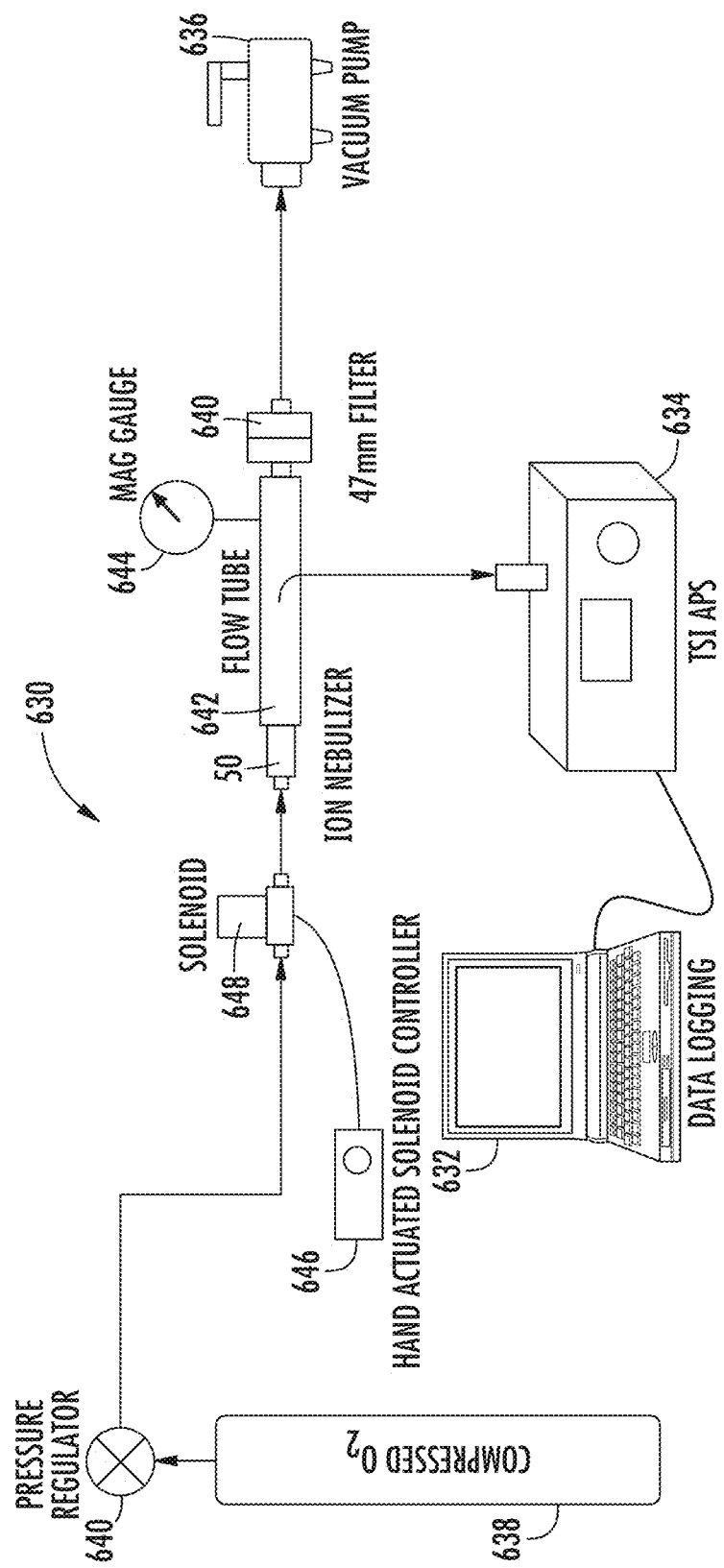
Figure 44:
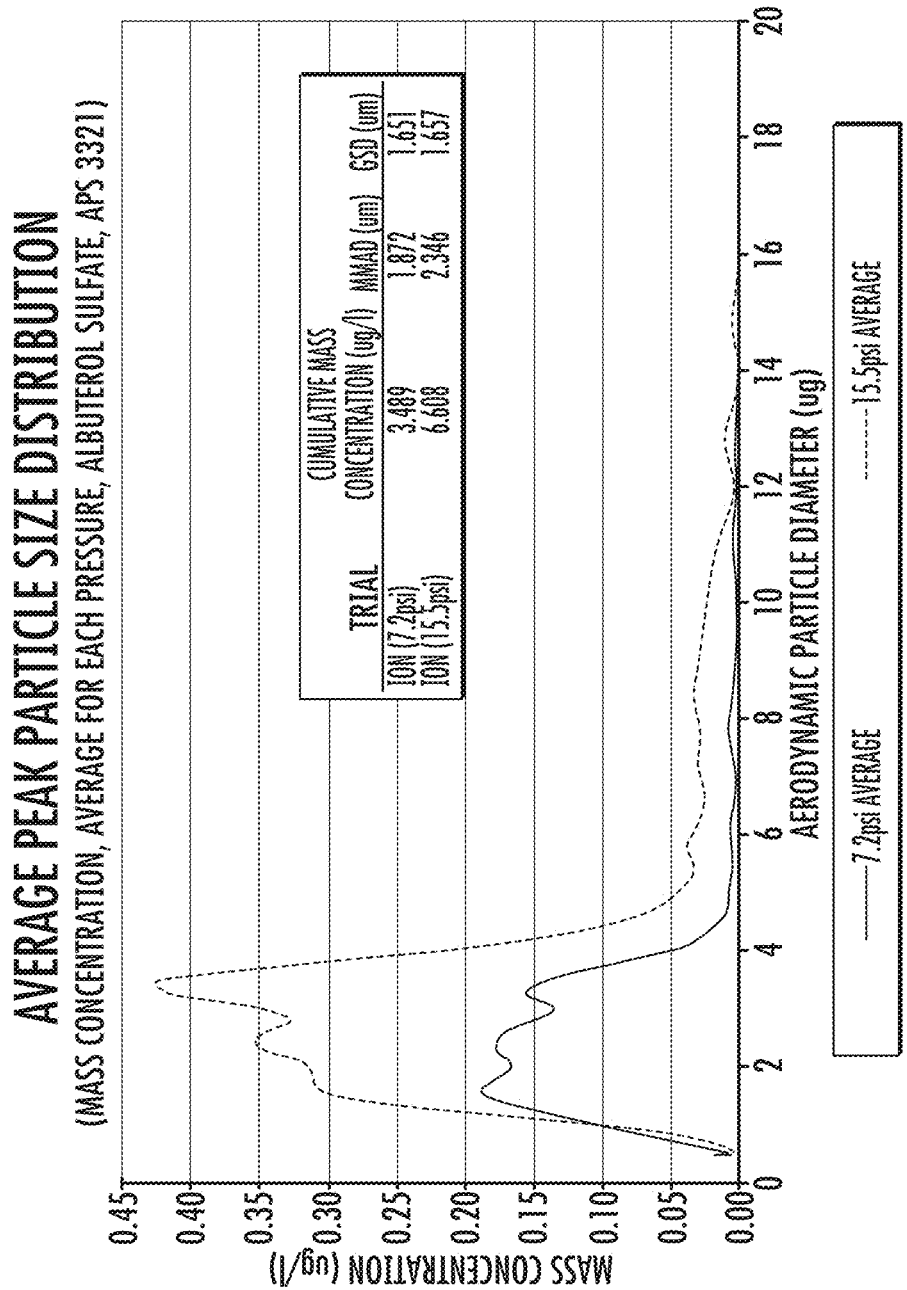

FIG. 44 is a graph showing the average peak particle size distribution with the mass concentration and average for each pulse pressure as described in the test of FIG. 42 in accordance with a non-limiting example.

Figure 45A:
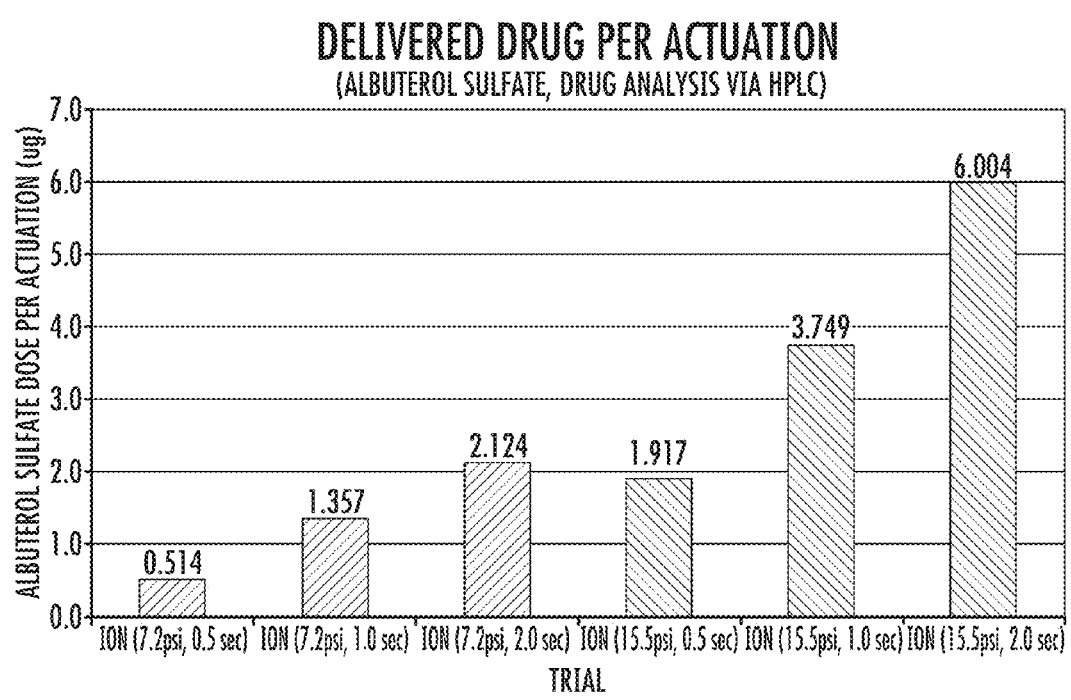

FIG. 45A is a bar chart showing the amount of delivered drug as albuterol sulfate per actuation as described in the test of FIG. 42 in accordance with a non-limiting example.

FIG. 45B is a chart showing the total delivered drug results from the pulsed air trials using the test set-up shown in FIG. 42.

Figure 28:
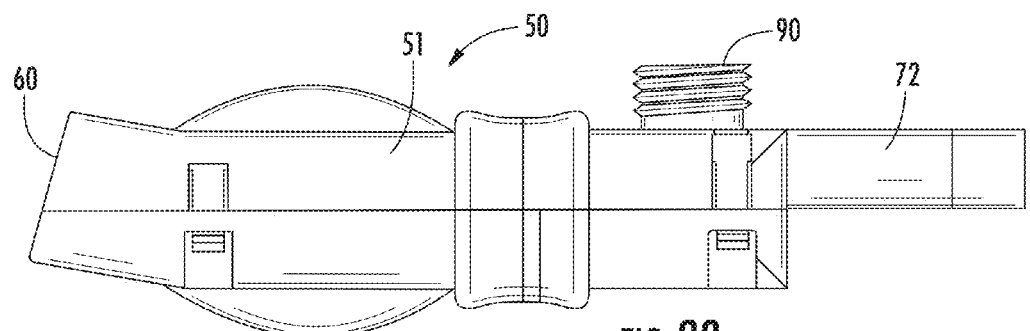
FIG. 28 is a side elevation view of the nebulizer shown in FIGS. 1-16.
Figure 29:
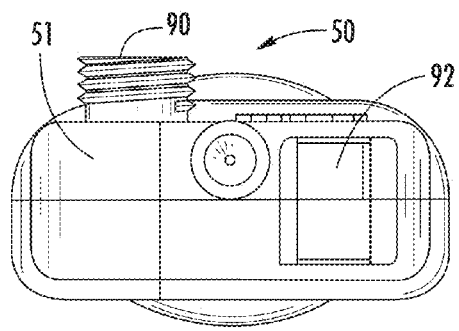
FIG. 29 is an end elevation view of the nebulizer shown in FIG. 28.
Figure 30:
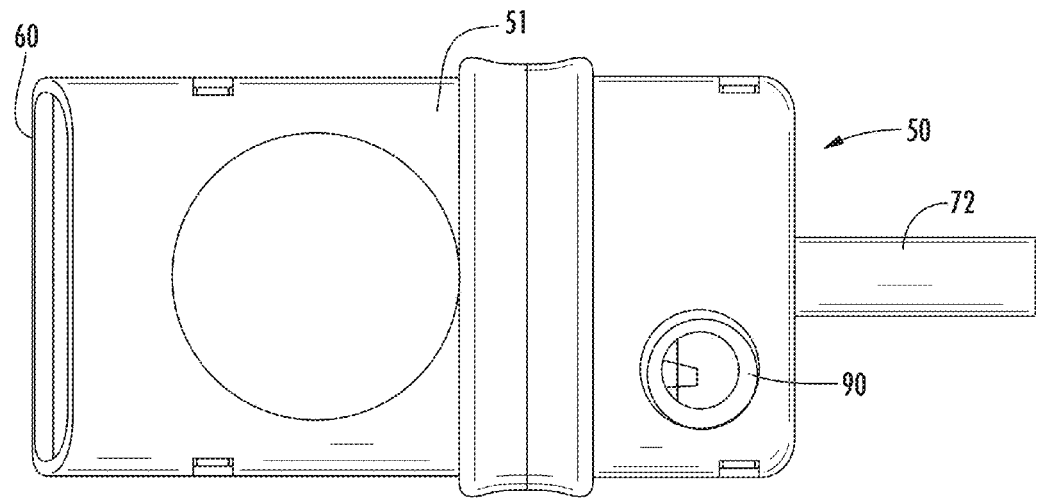
FIG. 30 is a plan view of the nebulizer shown in FIG. 28.
Figure 31:
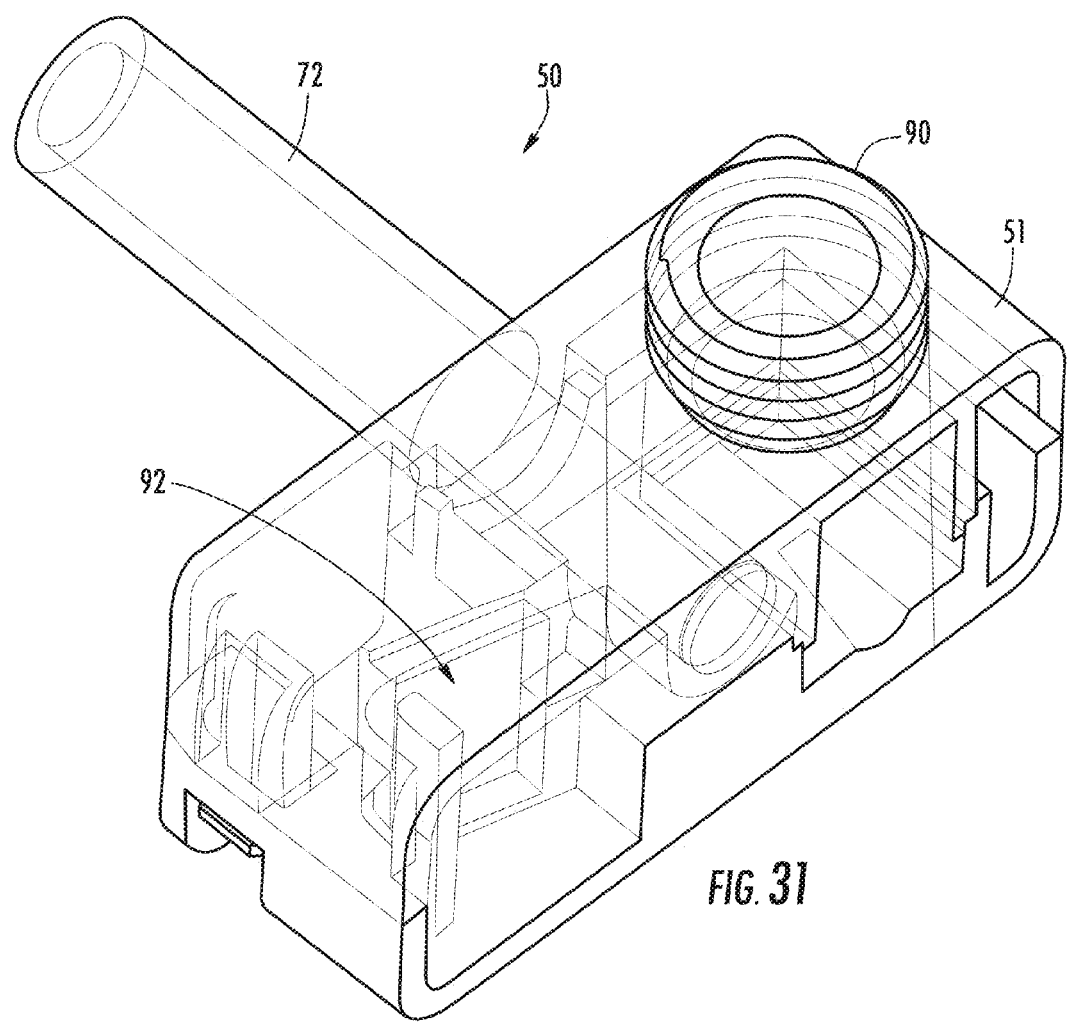
FIG. 31 is a phantom diagram showing internal components of a portion of the nebulizer body that includes the air channel section, air line and vent in accordance with a non-limiting example.
Figure 32:
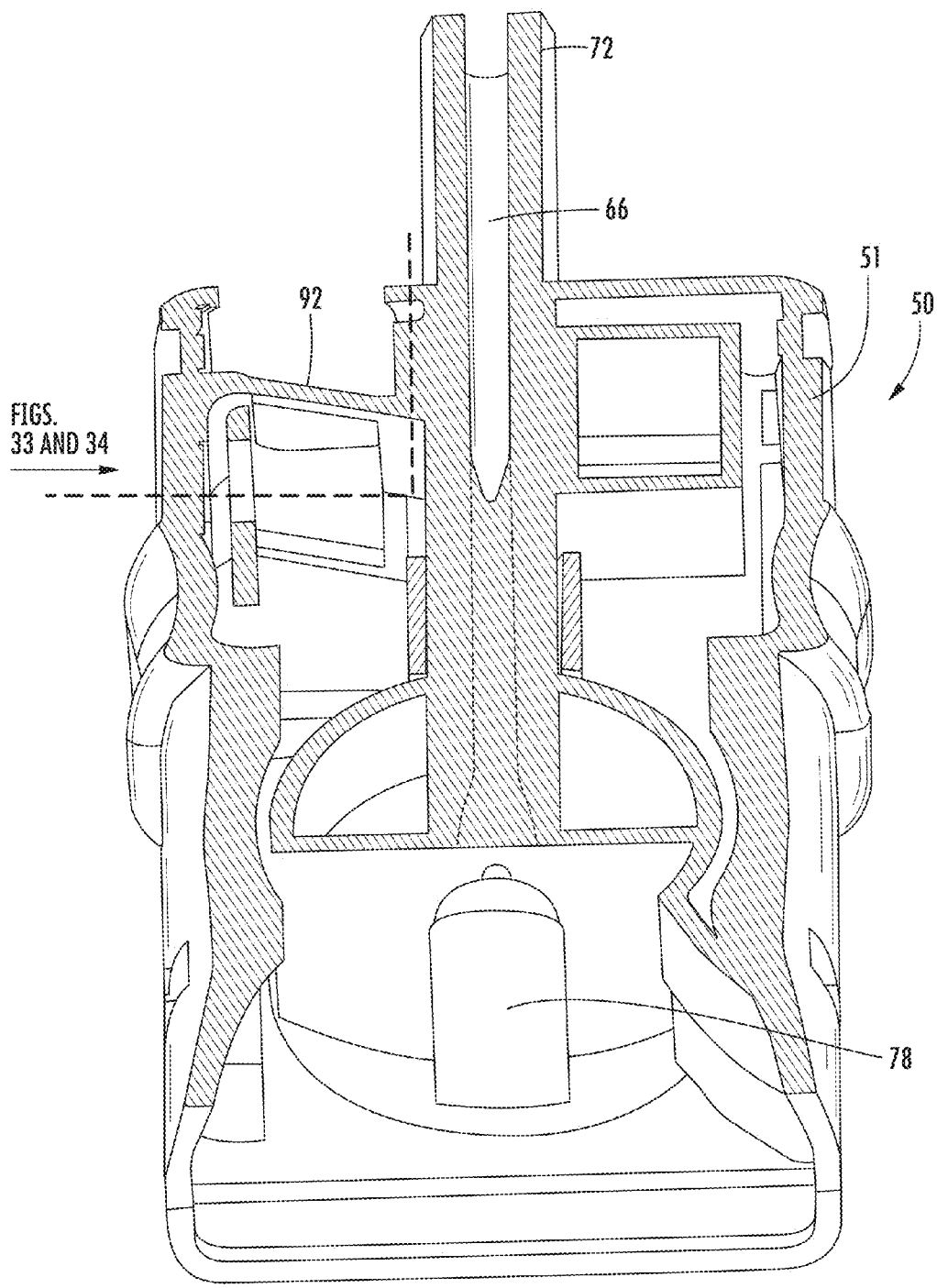
FIG. 32 is a perspective view in partial cut-away of the nebulizer body showing components of the nebulizer body.
Figure 33:
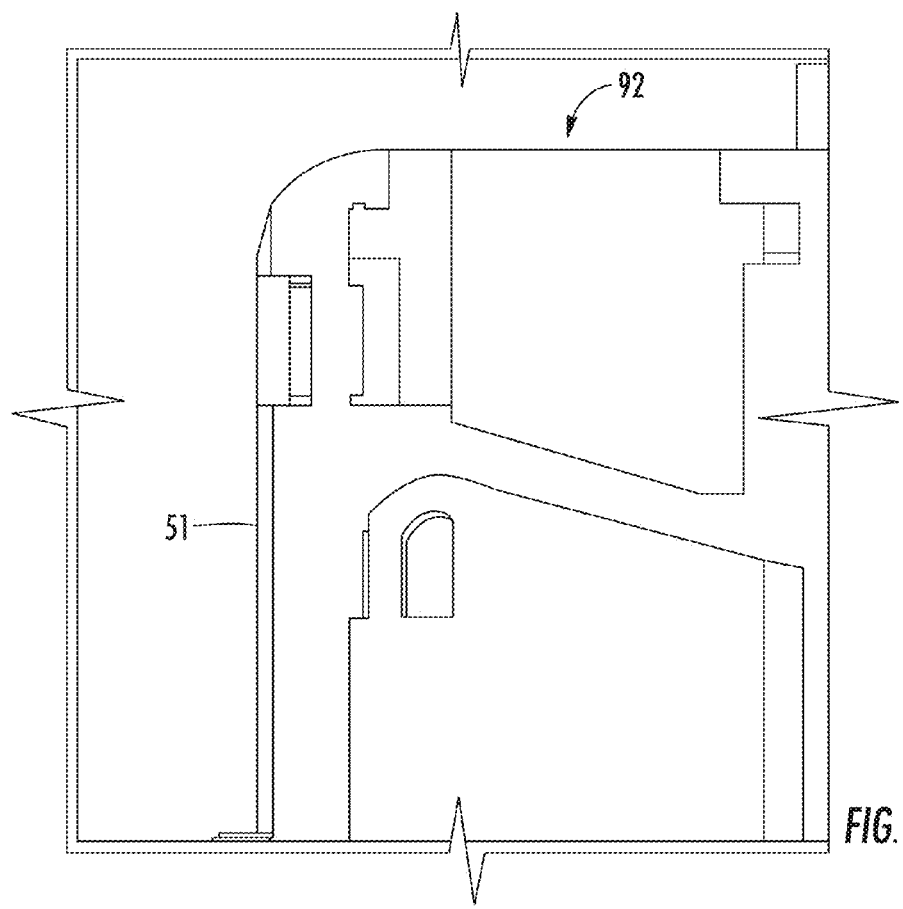
FIG. 33 is a top plan view of a portion of the nebulizer body shown in FIG. 32 and showing details of the vent in accordance with a non-limiting example.
Figure 34:
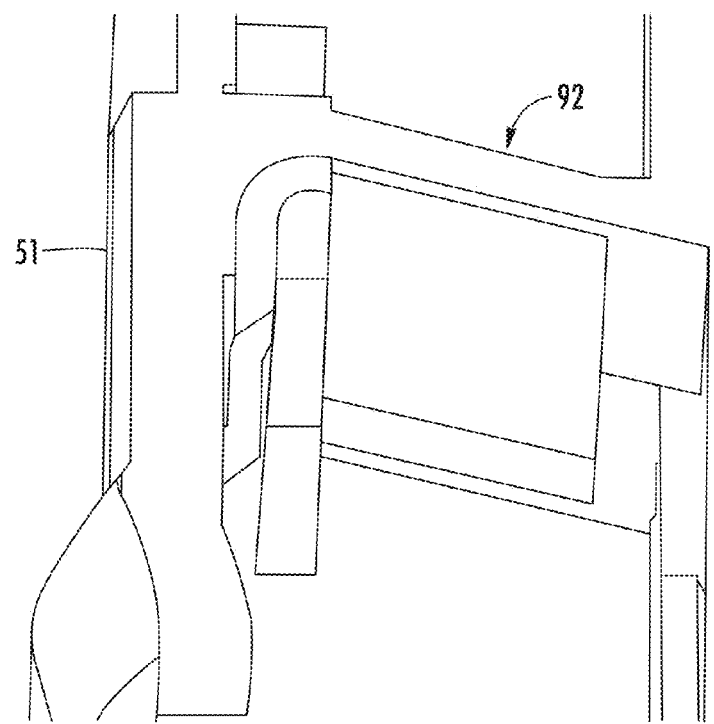
FIG. 34 is another top plan view of the vent of FIG. 33.
Figure 46:
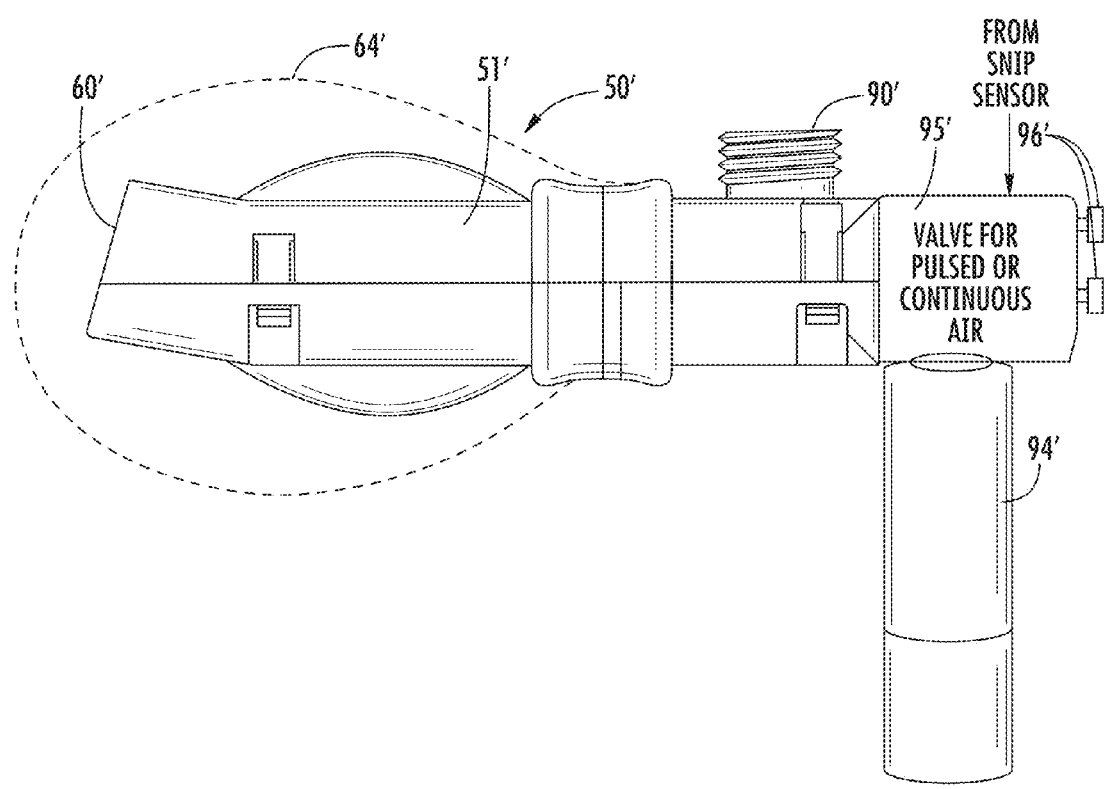

FIG. 46 is a side elevation view of a nebulizer similar to that shown in FIG. 28, but including a gas canister connected to a valve to provide either a pulsed or continuous air flow through the nebulizer that may be actuated by a negative inspiratory pressure.

Figure 47:
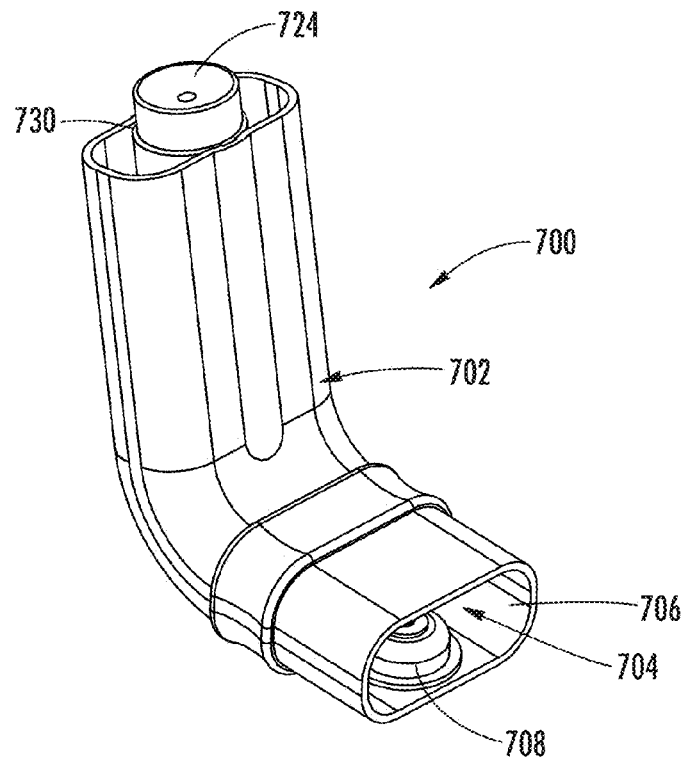

FIG. 47 is a perspective view of a metered dose nebulizer in accordance with a non-limiting example.

Figure 48:
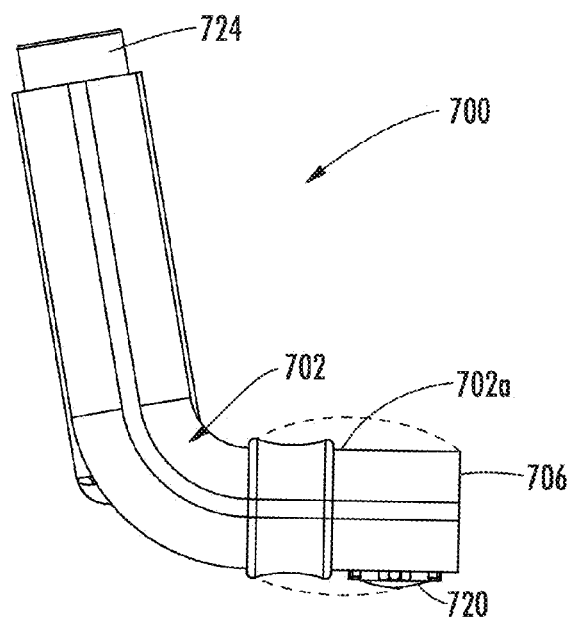

FIG. 48 is a side elevation view of the metered dose nebulizer shown in FIG. 47 in accordance with a non-limiting example.

Figure 49:
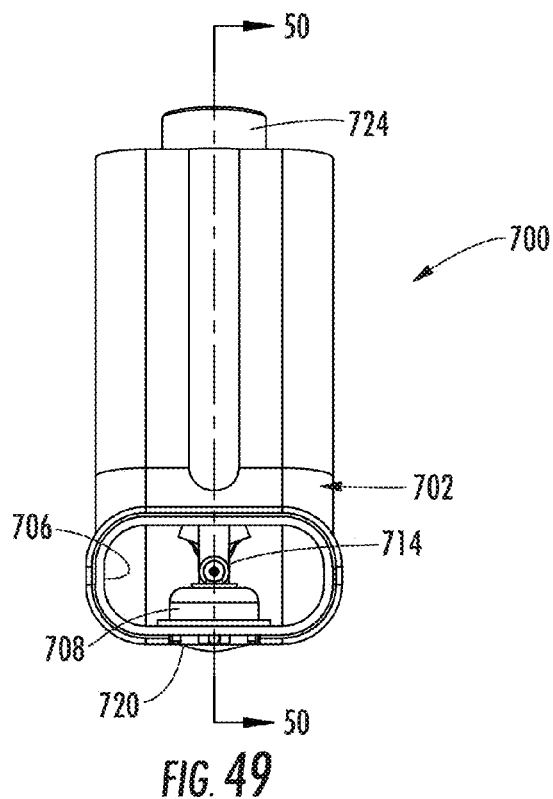

FIG. 49 is a front elevation view of the metered dose nebulizer shown in FIG. 47 in accordance with a non-limiting example.

Figure 50:
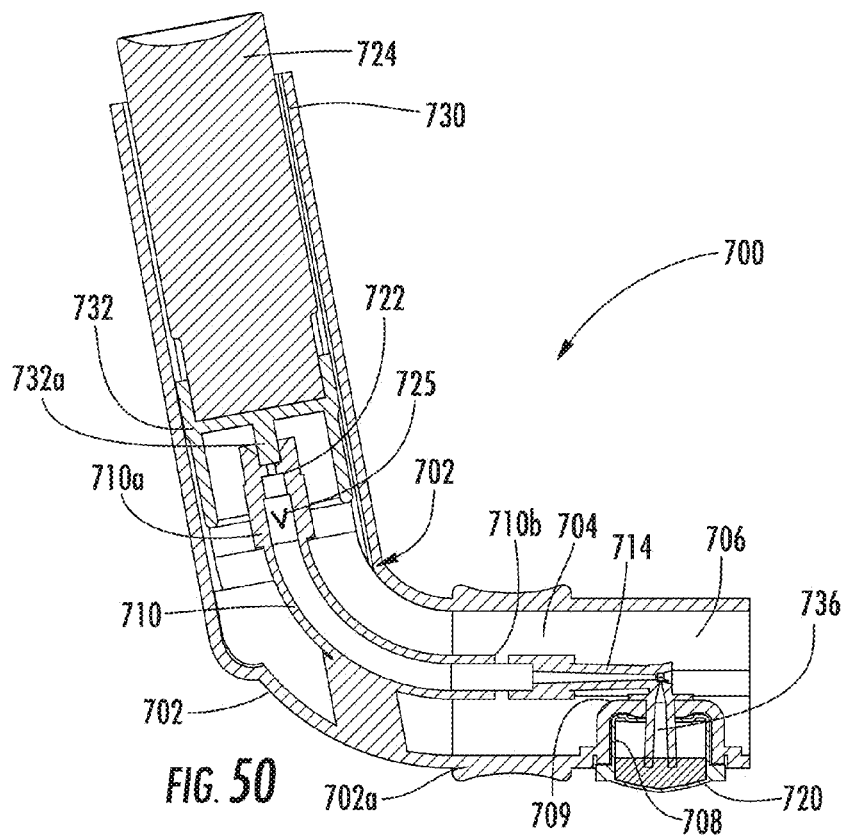

FIG. 50 is a sectional view taken along line 50-50 of FIG. 49 of the metered dose nebulizer in accordance with a non-limiting example.

Figure 51:
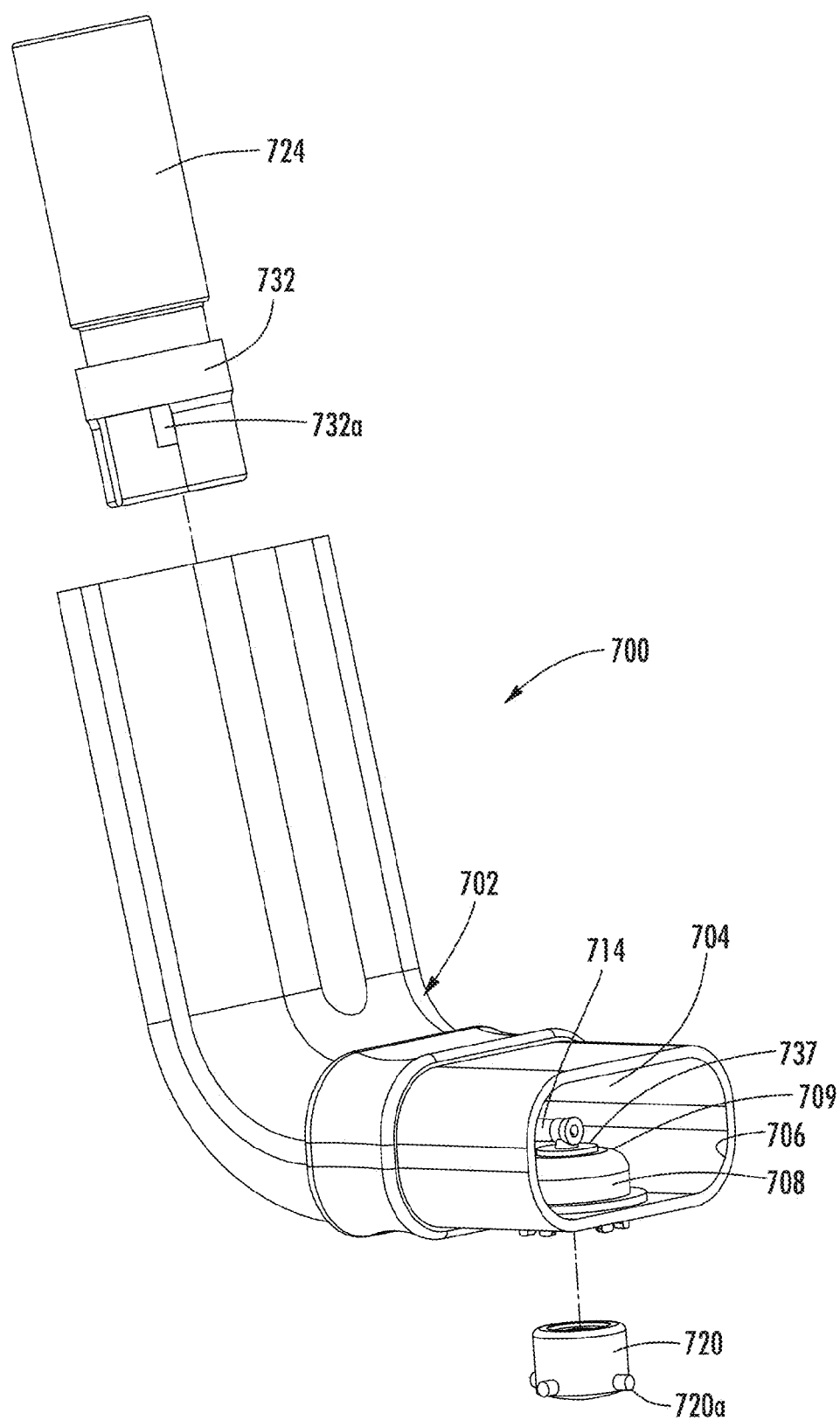

FIG. 51 is an exploded perspective view of the metered dose nebulizer shown in FIG. 47 in accordance with a non-limiting example.

Figure 52:
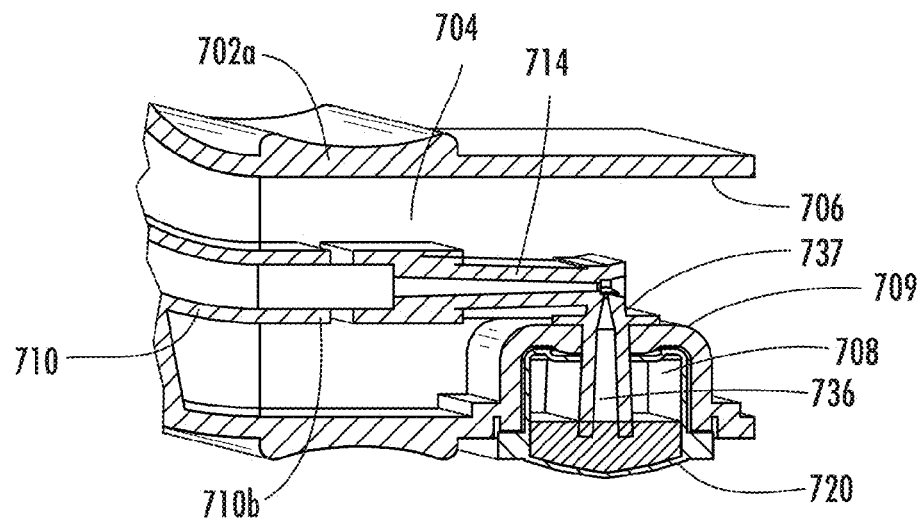

FIG. 52 is an enlarged isometric, partial sectional view of the nebulizer outlet for the nebulizer shown in FIGS. 47-51 and showing the venturi nozzle and suction line formed together and replaceable within the nebulizer body as one unit.

Figure 53:
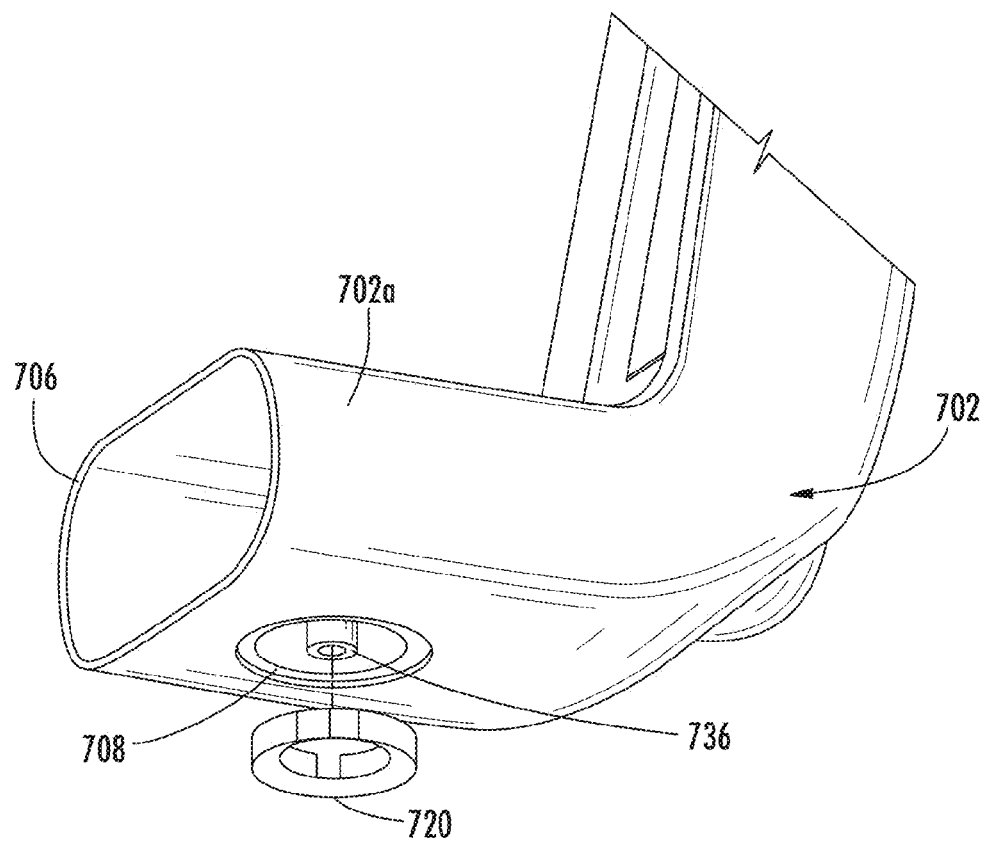

FIG. 53 is an enlarged perspective view of a portion of the underside of the nebulizer body at its nebulizer outlet and showing the medication container that can be inserted within the medication receiver and connected into the suction line.

Figure 54:
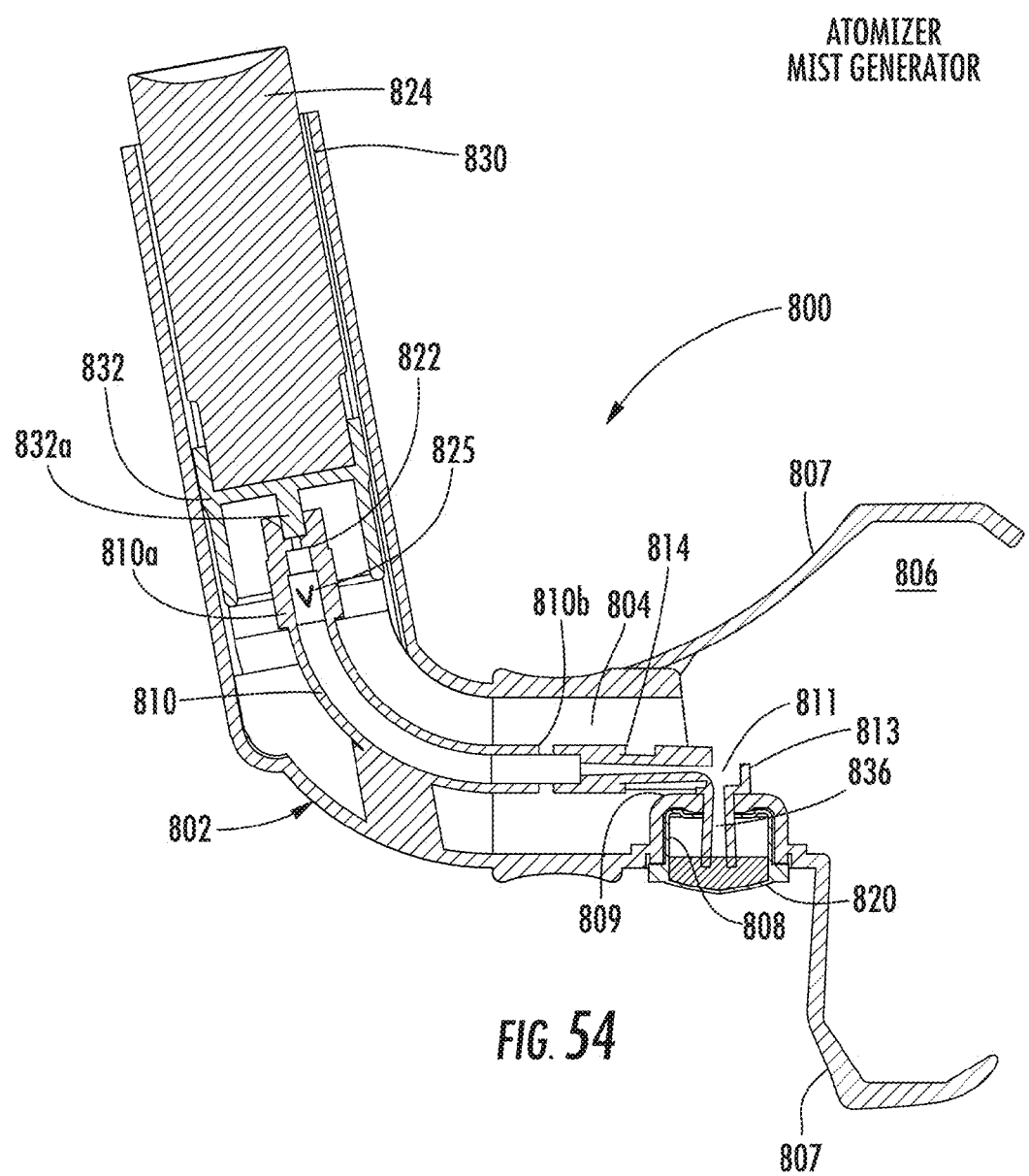

FIG. 54 is a sectional view of a metered dose atomizer similar to the nebulizer sectional view shown in FIG. 50, but modified to form a metered dose atomizer in accordance with a non-limiting example.

Figure 18:
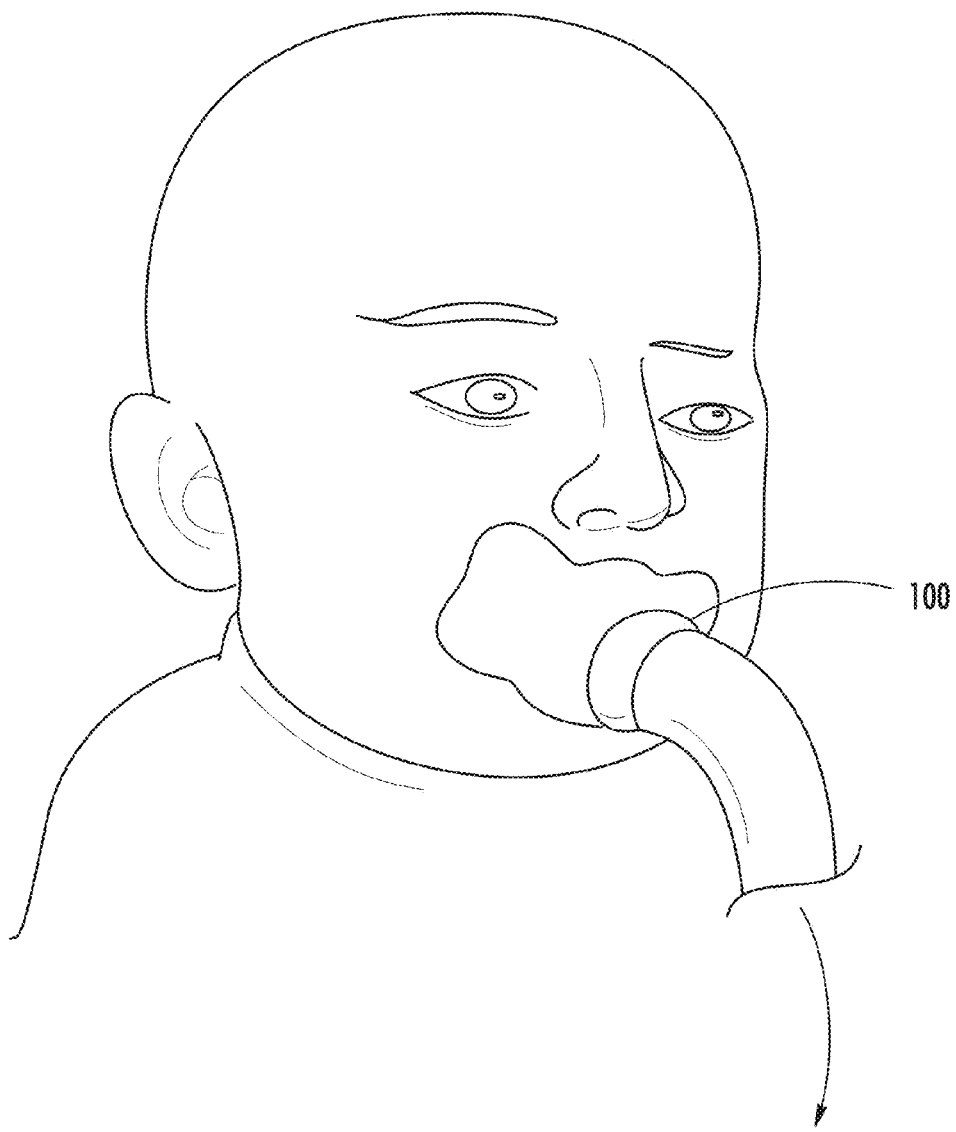
FIG. 18 is a general environmental view of a child sucking on a pediatric nebulizer such as disclosed in FIGS. 19-22 in accordance with non-limiting examples.
Figure 55:
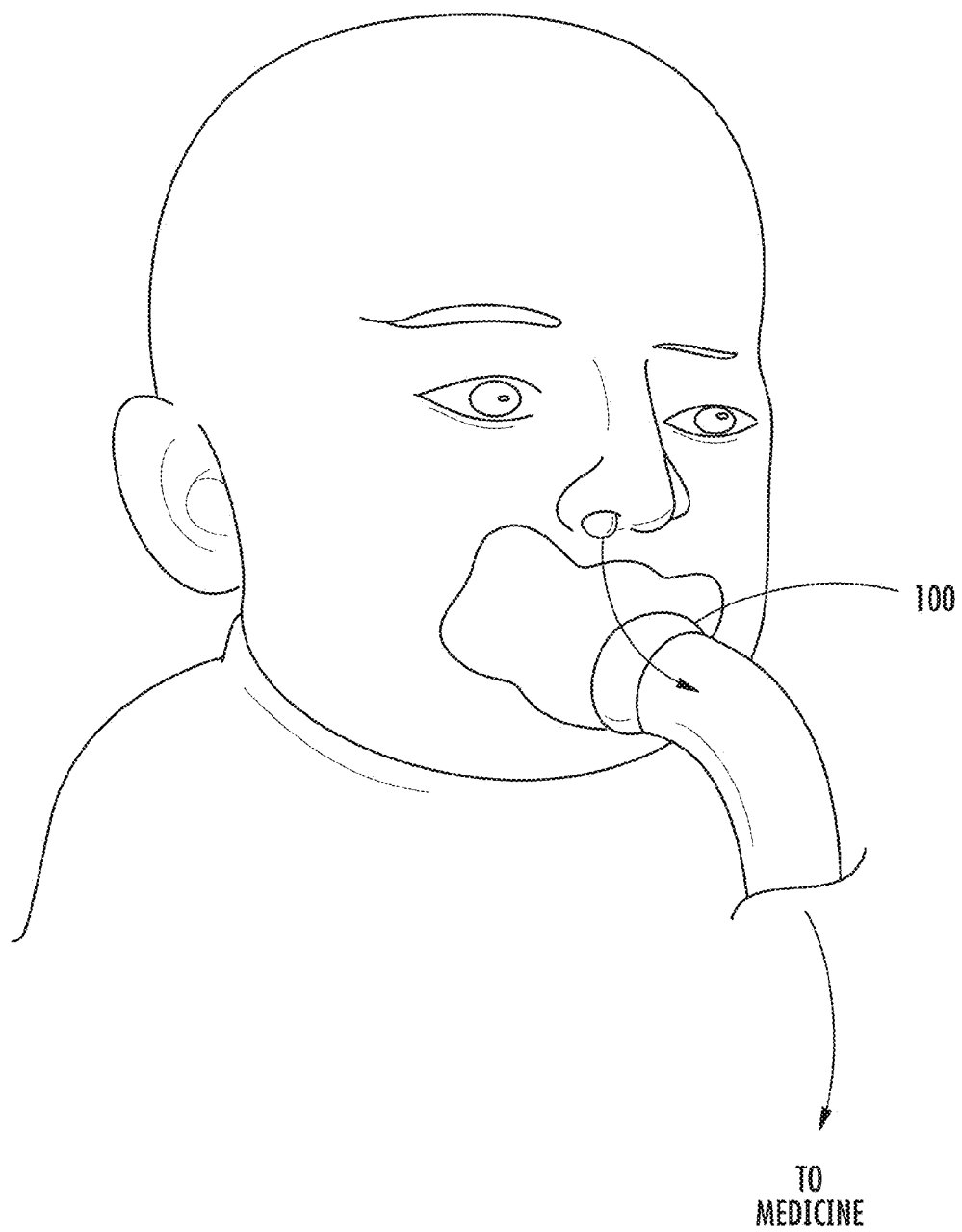

FIG. 55 is another general environmental view of a child sucking on a pediatric nebulizer such as the nebulizer shown in FIG. 18 and disclosed in FIGS. 19-22 and modified in accordance with non-limiting examples and showing a sensor for SNIP (Sniff Nasal Inspiratory Pressure) that can be used to actuate operation of the pediatric nebulizer.

DETAILED DESCRIPTION OF THE PREFERRED EMBODIMENTS

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

In accordance with a non-limiting example as shown in the examples of FIGS. 1-16 and 28-35, and disclosed in the incorporated by reference Ser. No. 13/799,196 and now allowed Ser. No. 13/353,611 applications, the nebulizer uses a vent that is formed in the nebulizer body and communicates with the air channel section and medication reservoir to vent the air channel section and medication reservoir to outside ambient air. A primary suction line extends from the medication reservoir to the low pressure mixing chamber through which medication is drawn upward and mixed with air passing through the venturi nozzle and nebulized for discharge through the nebulizer outlet. This vent is configured to vent the air channel section and medication reservoir to atmospheric pressure such that at standard temperature and pressure (STP), a differential pressure results between the venturi nozzle and medication reservoir such that no medication is drawn upward through the primary suction line for nebulization and discharge through the nebulizer outlet into a negative inspiratory pressure is created from inhalation by a user. The air line extends through the air channel section and includes the venturi nozzle and is configured at its end to form the low pressure mixing chamber. Air is continually pressurized in the air line from an air source, but at a low pressure that works in conjunction with the vent such that at standard temperature and pressure (STP), the differential pressure resulting between the venturi nozzle and medication reservoir is such that no medication is drawn upward through the primary suction line for nebulization and discharge. The various pressure flow diagrams in FIGS. 2-16 show the various applied pressures and suction and when medication is drawn upward through the primary suction line and nebulization occurs and the forces involved, such as through inhalation.

In accordance with a non-limiting example as disclosed in the Ser. Nos. 13/799,196 and 13/353,611 applications, the nebulizer initiates nebulization upon inhalation. The nebulizer is configured as an intra-oral nebulizer and can be operated with half liter air flow using the low pressure air source in one example. Nebulization is activated by a patient breathing and inhaling. Micro amounts of medication are released only when required during inspiration and will not flow into the gut because of the low velocity and the configuration of the nebulizer as an intra-oral nebulizer. This is also aided because the venturi nozzle is positioned intra-orally. Because most dosages of the nebulized medication go into the lungs upon inhalation, if dangerous drugs are being inhaled during nebulization, it is not likely that they will be released into the ambient and surrounding air to harm others.

There are various mechanics of jet nebulizers that should be understood. A jet nebulizer is a device that is used to deliver medication to the respiratory system using a supplied air source. Traditional nebulizers have a vertical column of air passing through a reservoir of medication, which has a separation at the top of the nozzle allowing the air and medication to mix. This mixture accounts for the initial medication droplet formation due to the drastic change in surface area and aerodynamic effects of the mixture region. This initial droplet formation can be estimated from a linear stability analysis and an aerodynamic loading analysis using parameters such as the Reynolds number, Mach number, and Weber number. This initial droplet formation in this region is normally not sufficient for the desired deposition of the medication in the respiratory tract. To further reduce the droplet size, these droplets travel at high speed and collide with a baffle. This impact energy greatly reduces the droplet size to an acceptable level for deposition of medicine.

This traditional approach has several draw backs. One of the primary factors is that additional medication is required to deliver the proper dose to the desired region of the respiratory tract. Droplet formation occurs outside of the mouth in traditional devices and then has to travel through tubes, masks and the mouth. This additional travel period allows more particle to particle interaction. These particle collisions allow for particle combining, creating a larger diameter. Deposition will not occur with these larger diameter droplets, and therefore waste occurs.

Figure 1:
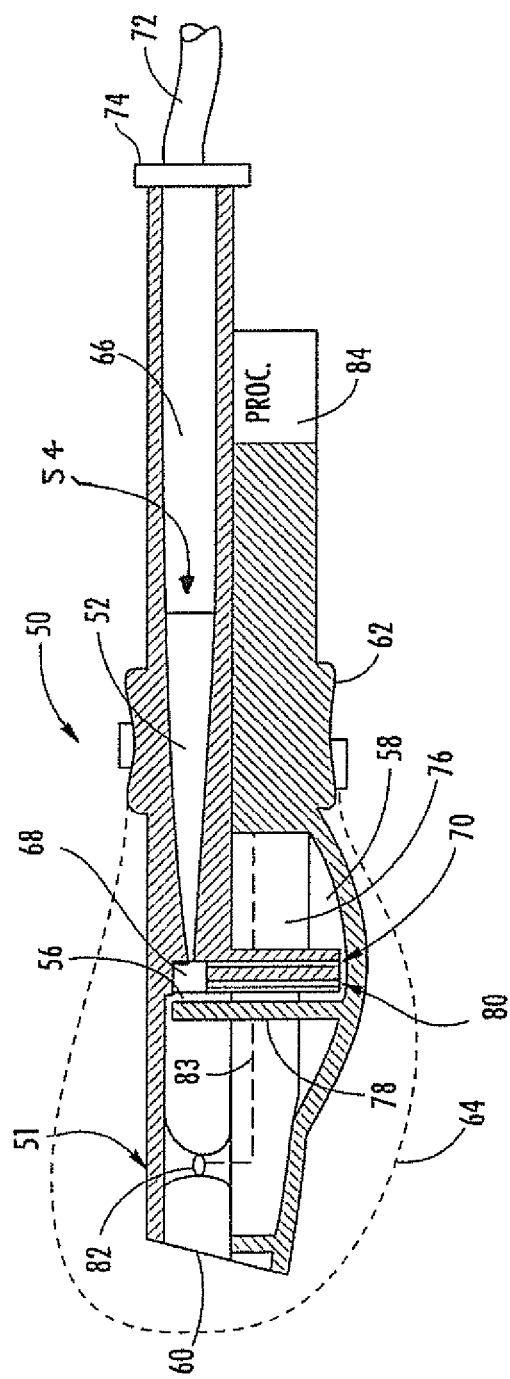
FIG. 1 is cross-sectional view of a nebulizer in accordance with a non-limiting example that is activated by negative inspiratory pressure and can be configured as a pediatric nebulizer in one non-limiting example and include in one embodiment a flow meter function.

Reducing these particle interactions is possible using the nebulizer as shown in FIG. 1. This nebulizer operates to nebulize in the mouth and operates as a horizontal nebulizer to allow for smaller droplet sizes for deposition at a lower zone in the respiratory tract and use less medication, resulting in less waste.

The illustrated nebulizer operates such that the differential pressures result with the nebulizer operating at a flow condition when at standard atmospheric pressure. Nebulization does not occur. As pressure decreases within the nebulizer due to inhalation, the differential pressures result in medication as fluid to flow up a suction line into the nozzle.

Figure 2:
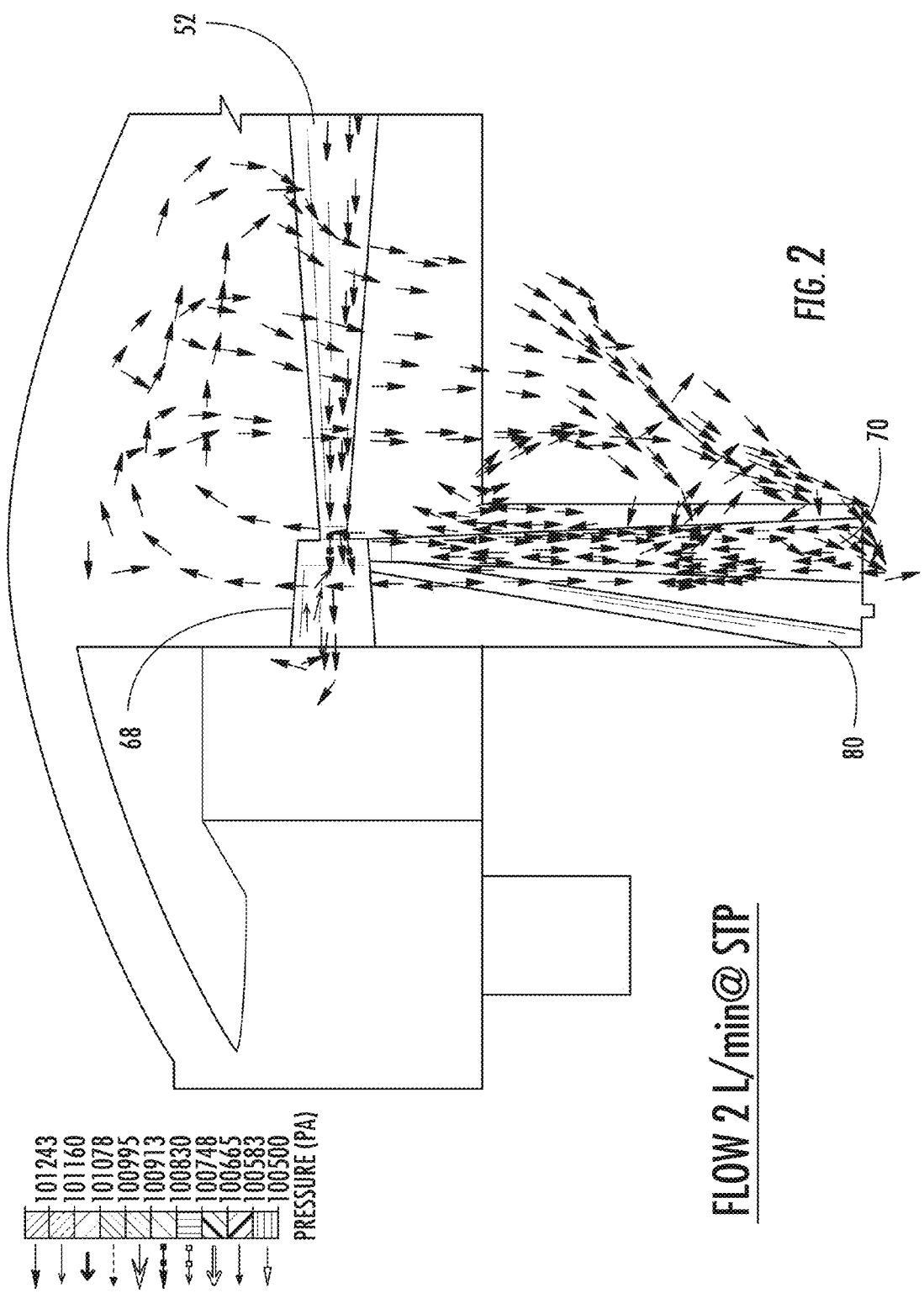
FIGS. 2-3 are sectional views of the nebulizer shown in FIG. 1 and showing a flow diagram of the airflow at 2 L/min at standard temperature and pressure (STP).
Figure 3:
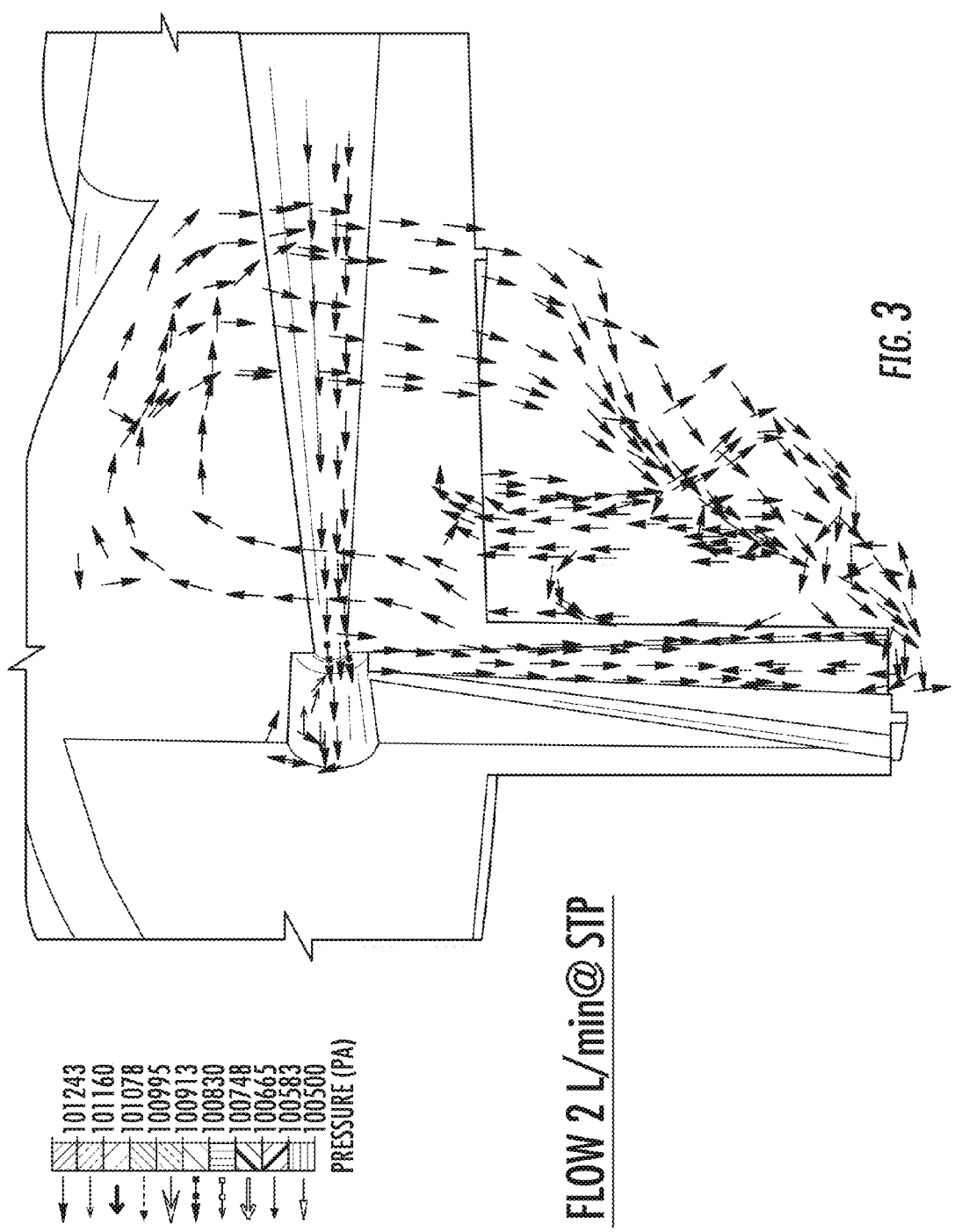
Figure 4:
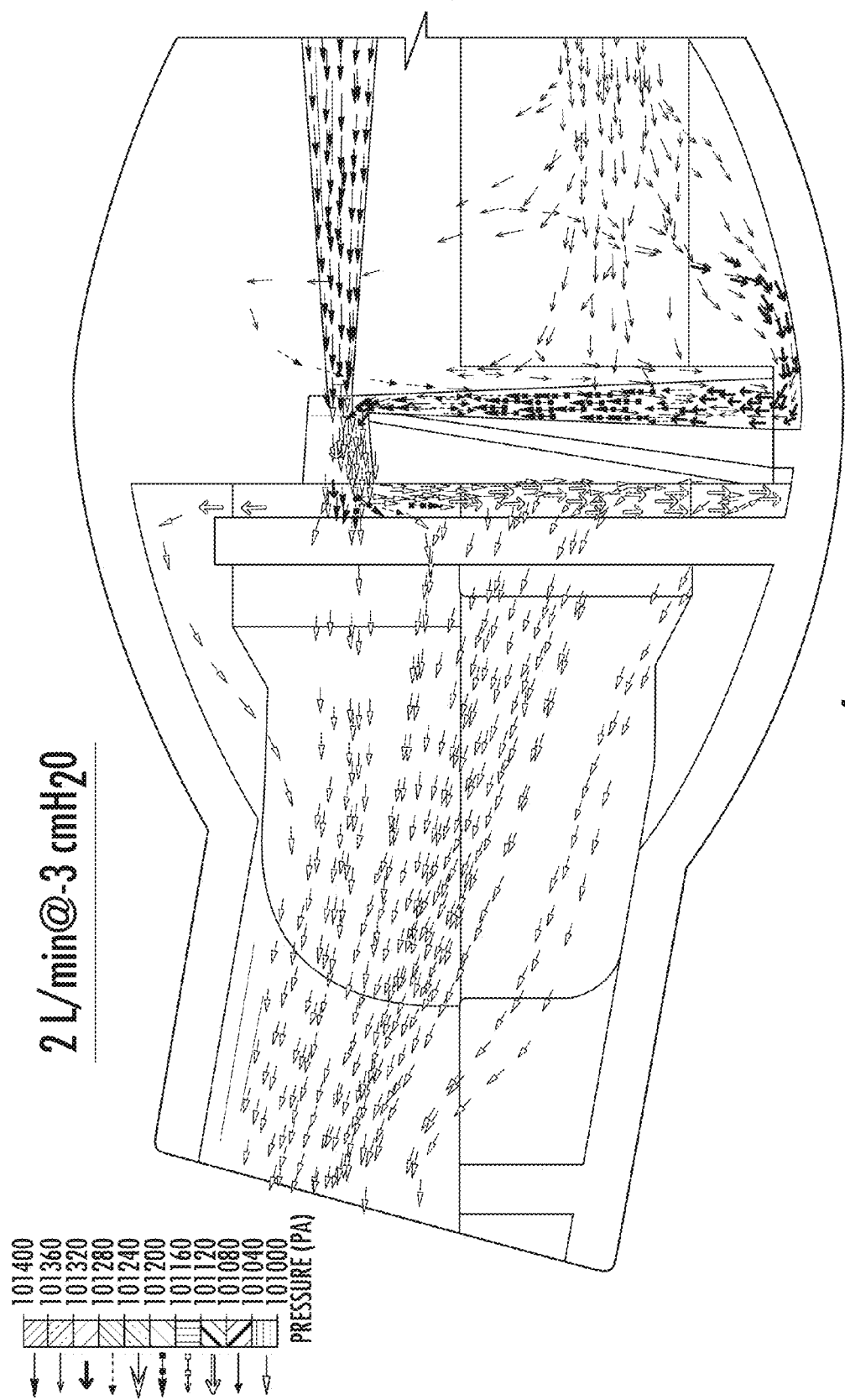
FIGS. 4-5 are flow diagrams showing the airflow through the nebulizer of FIG. 1 at 2 L/min at −3 $cmH_2O$.
Figure 5:
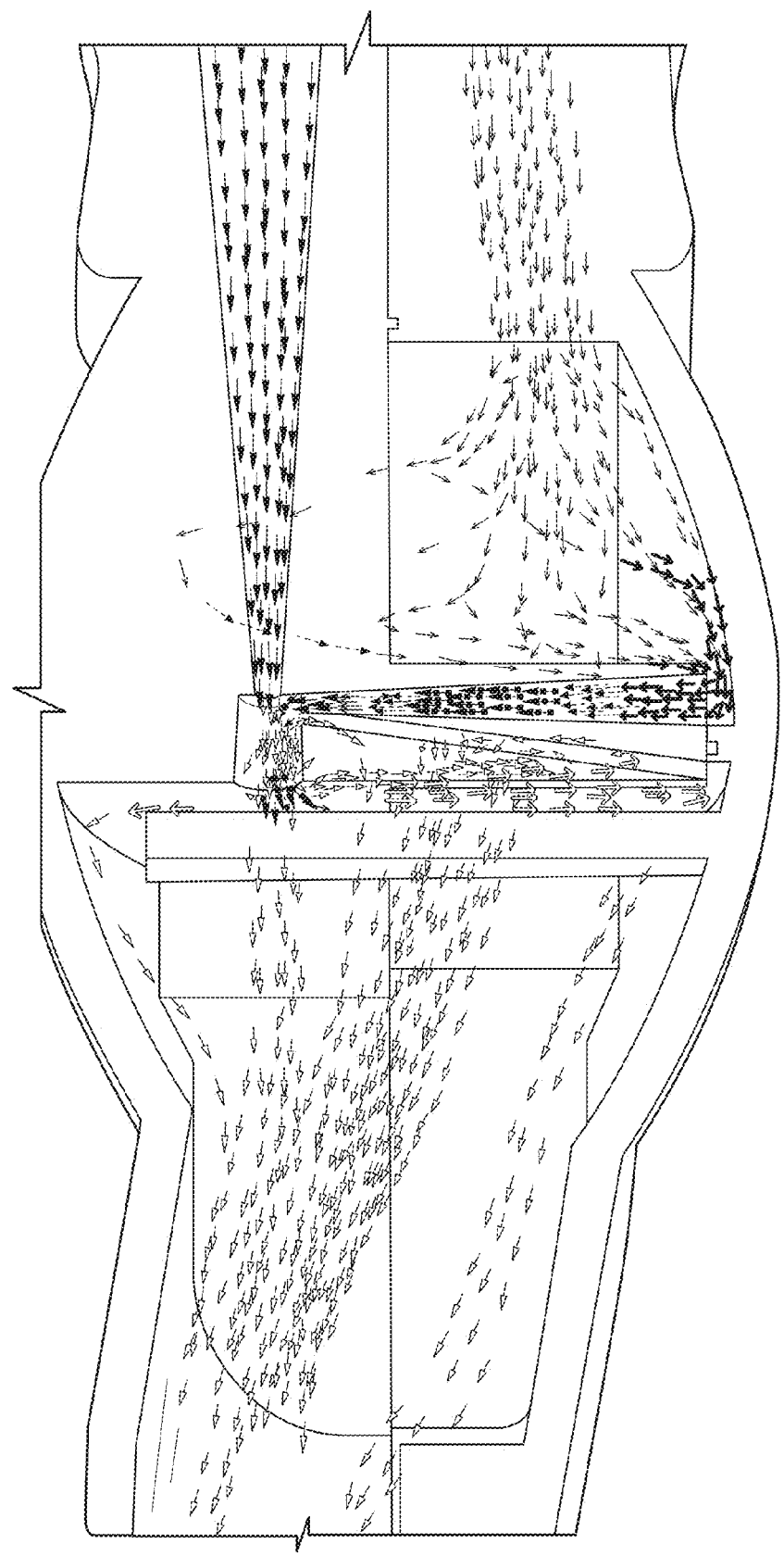
Figure 6:
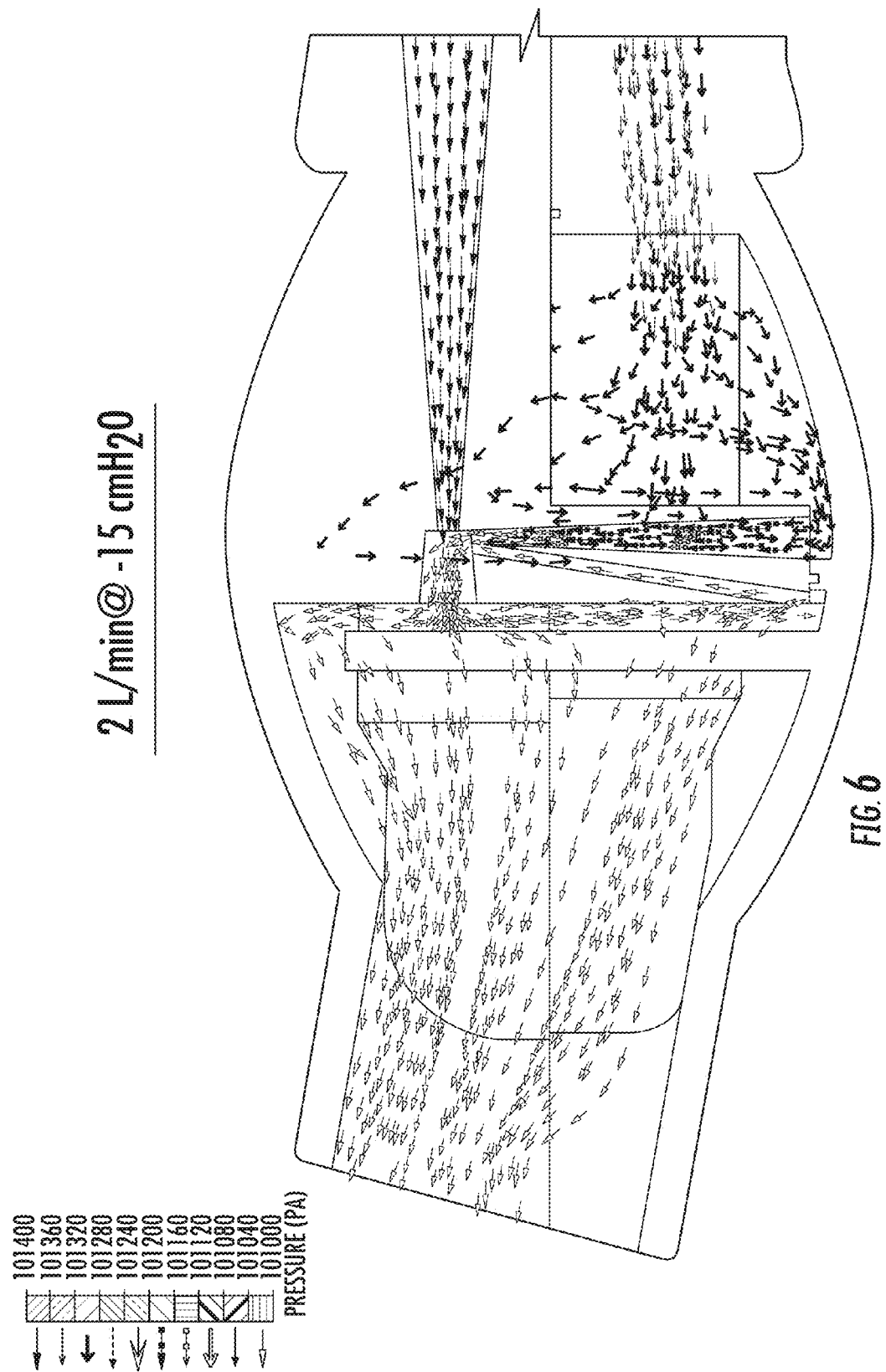
FIGS. 6-7 are flow diagrams showing the airflow through the nebulizer of FIG. 1 with 2 L/min at −15 $cmH_2O$.
Figure 7:
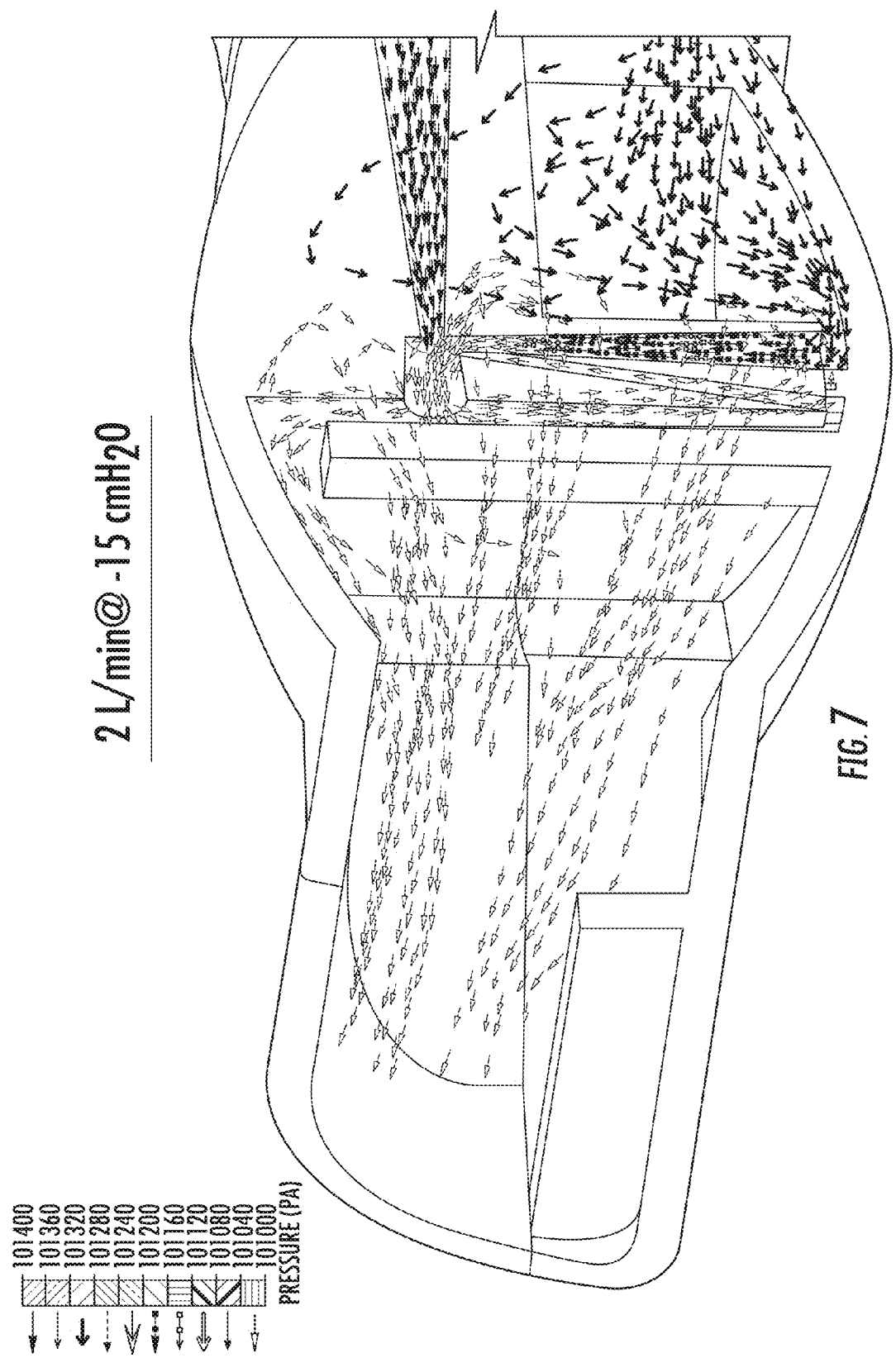
Figure 8:
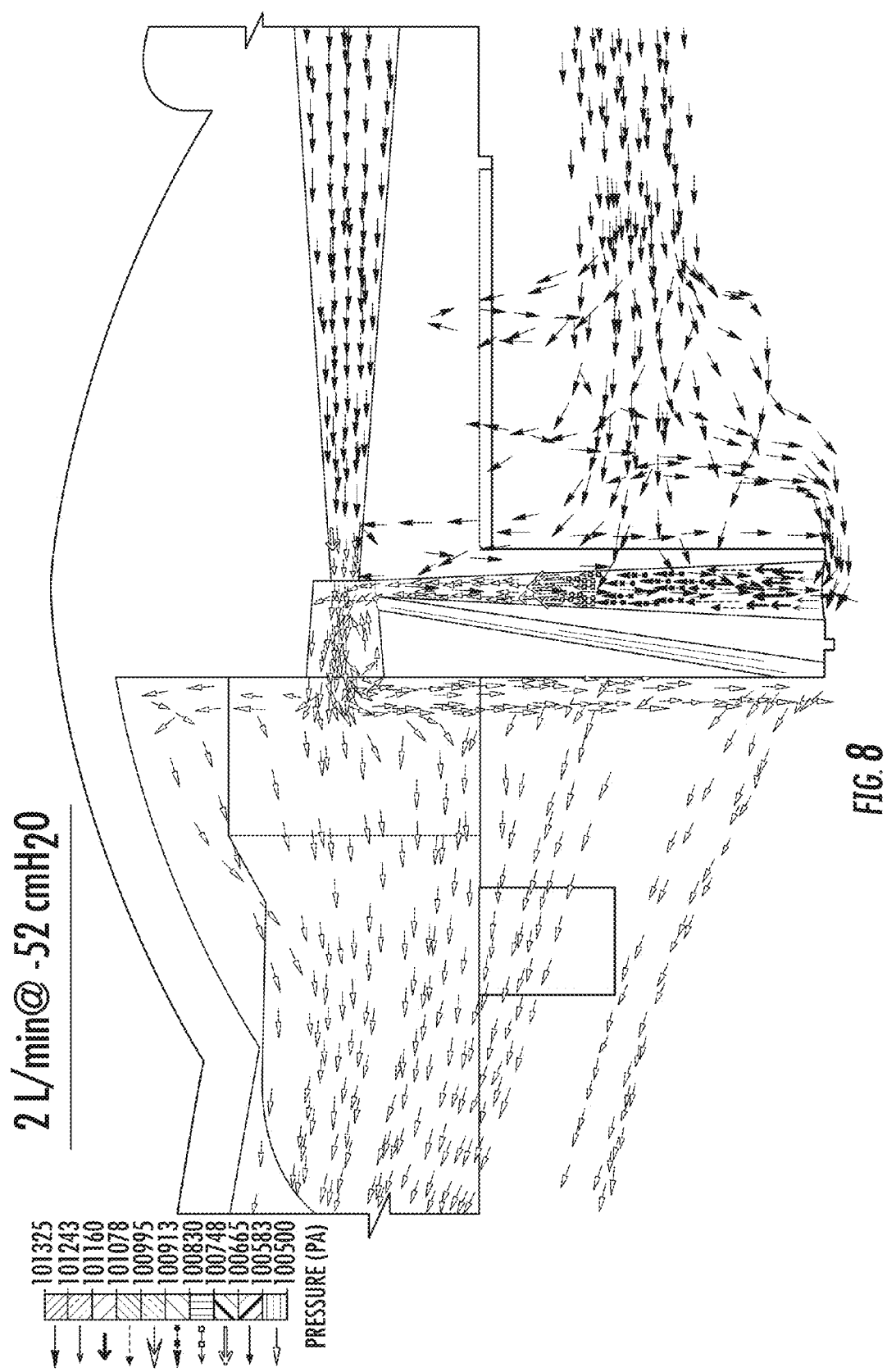
FIGS. 8-9 are flow diagrams showing the airflow through the nebulizer of FIG. 1 with 2 L/min at −52 $cmH_2O$.
Figure 9:
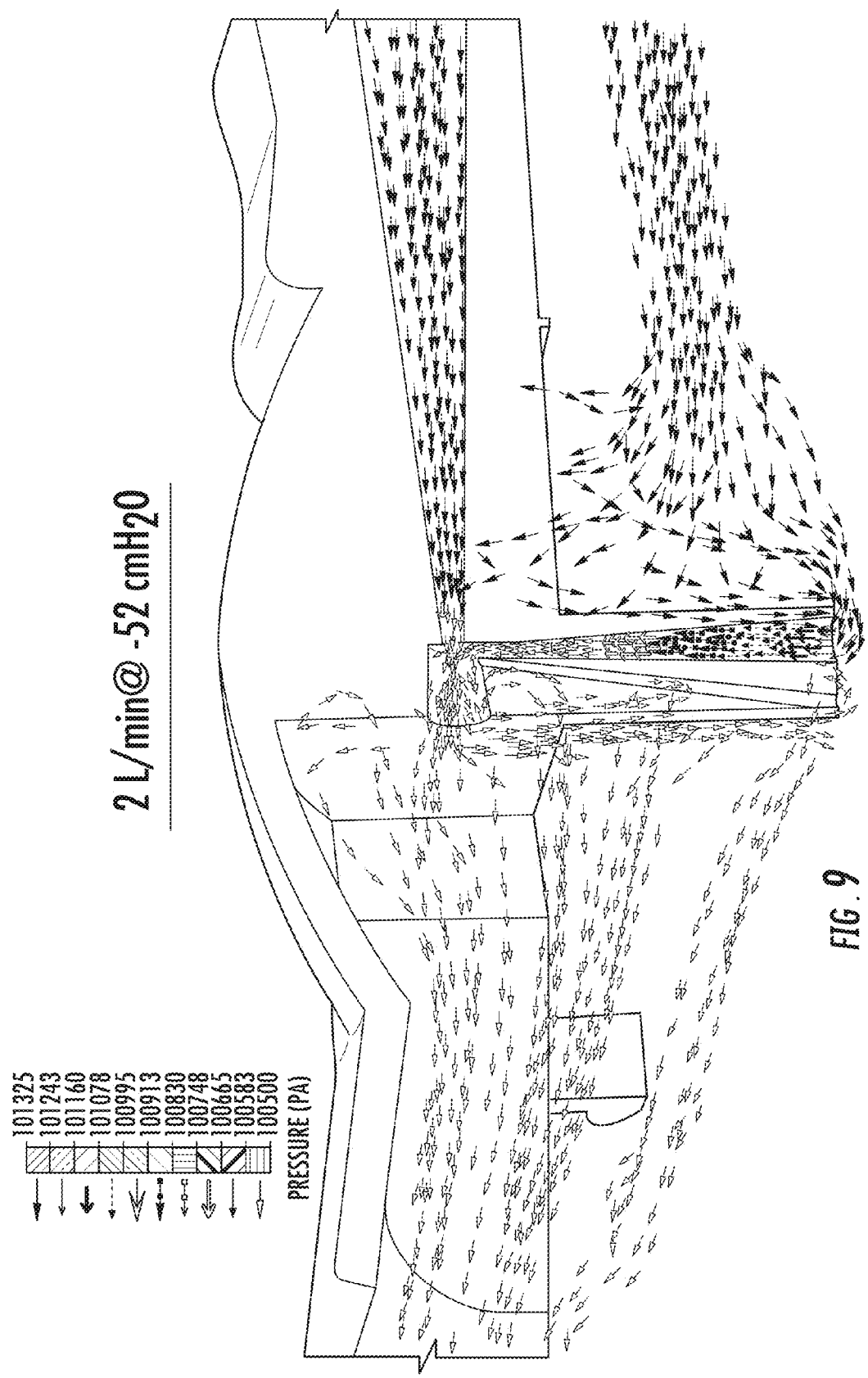
Figure 10:
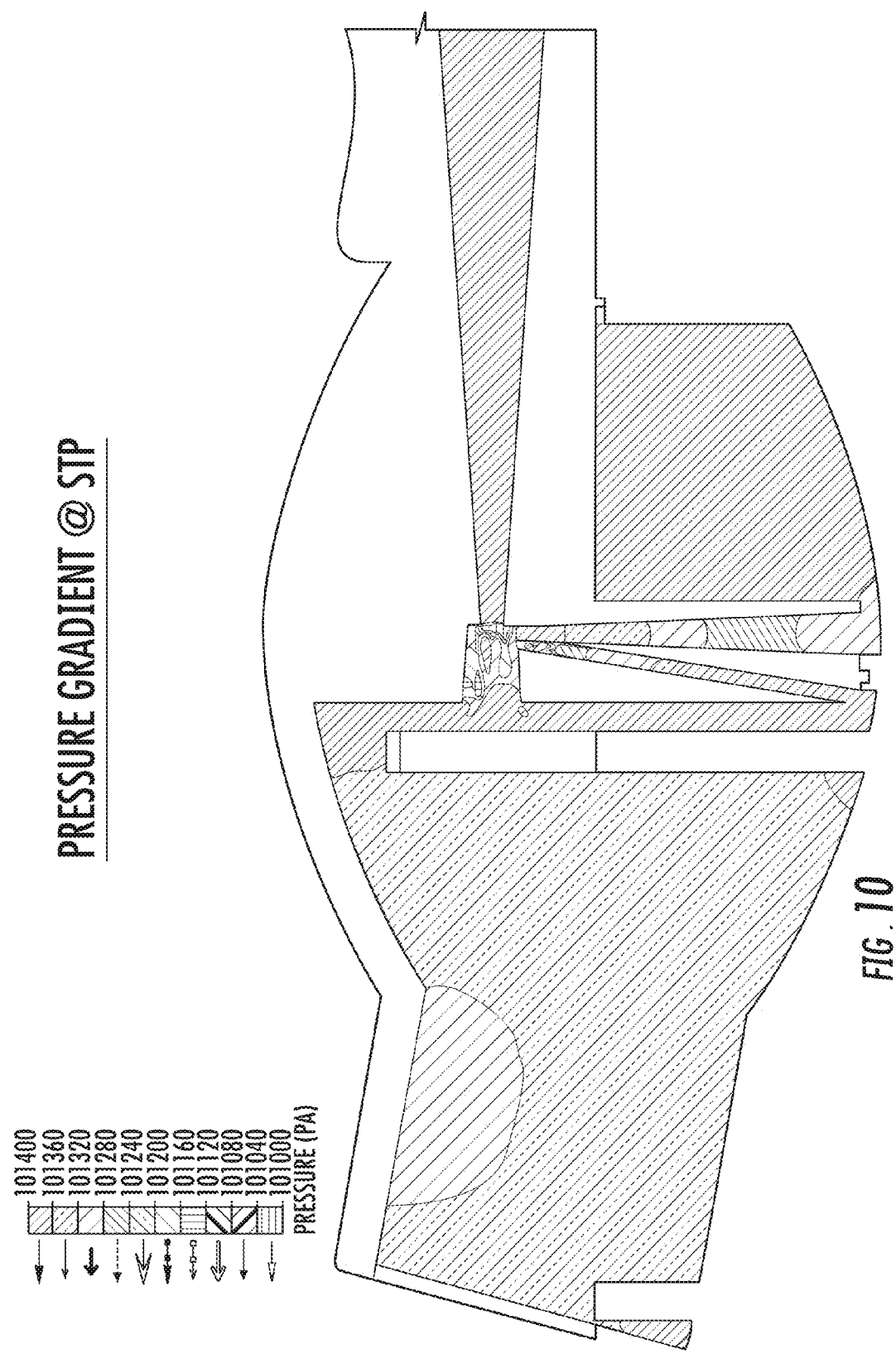
FIG. 10 is a diagram showing the pressure gradient in the nebulizer of FIG. 1 at standard temperature and pressure.
Figure 11:
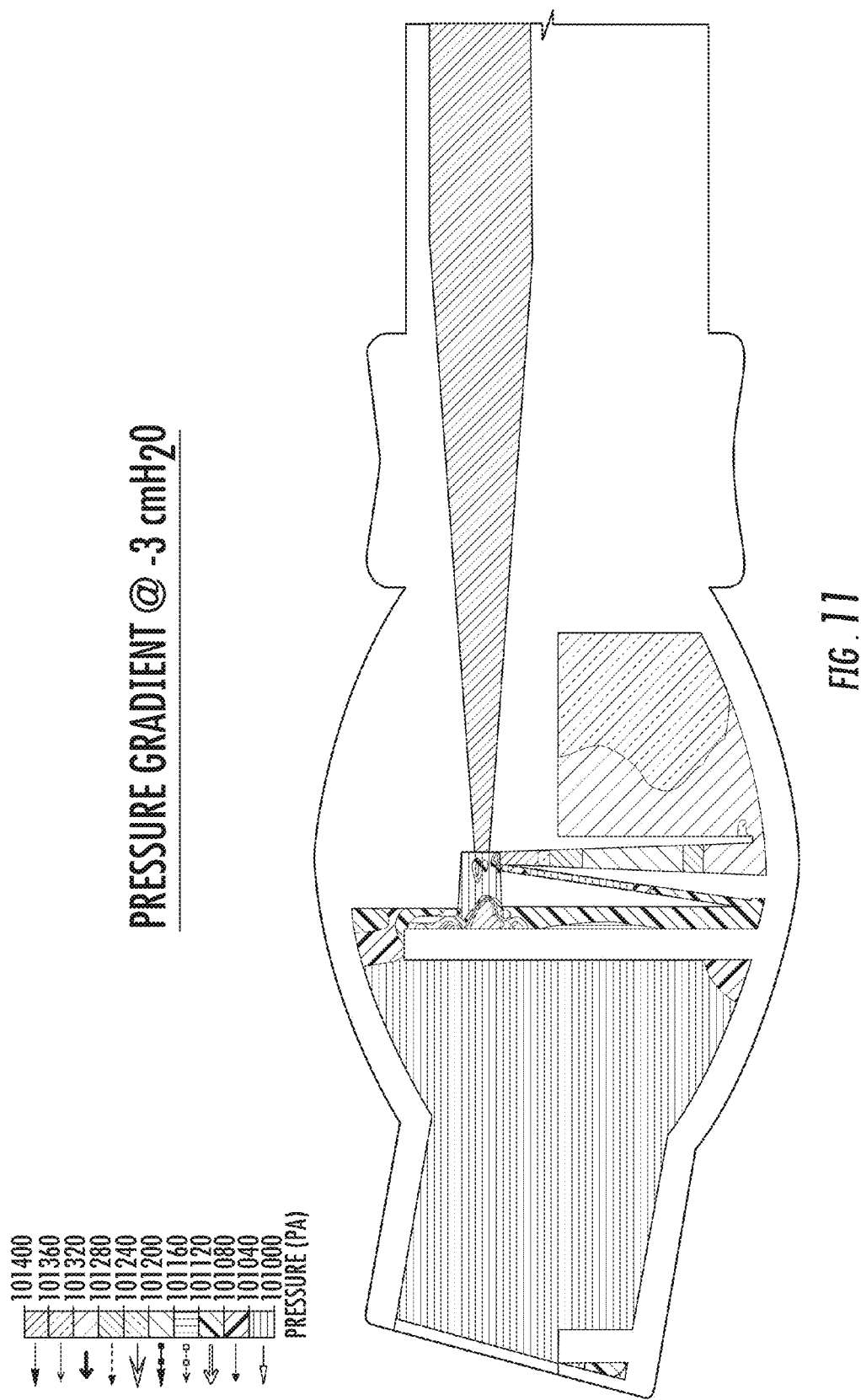
FIG. 11 is a diagram of the nebulizer of FIG. 1 showing the pressure gradient at −3 $cmH_2O$.
Figure 12:
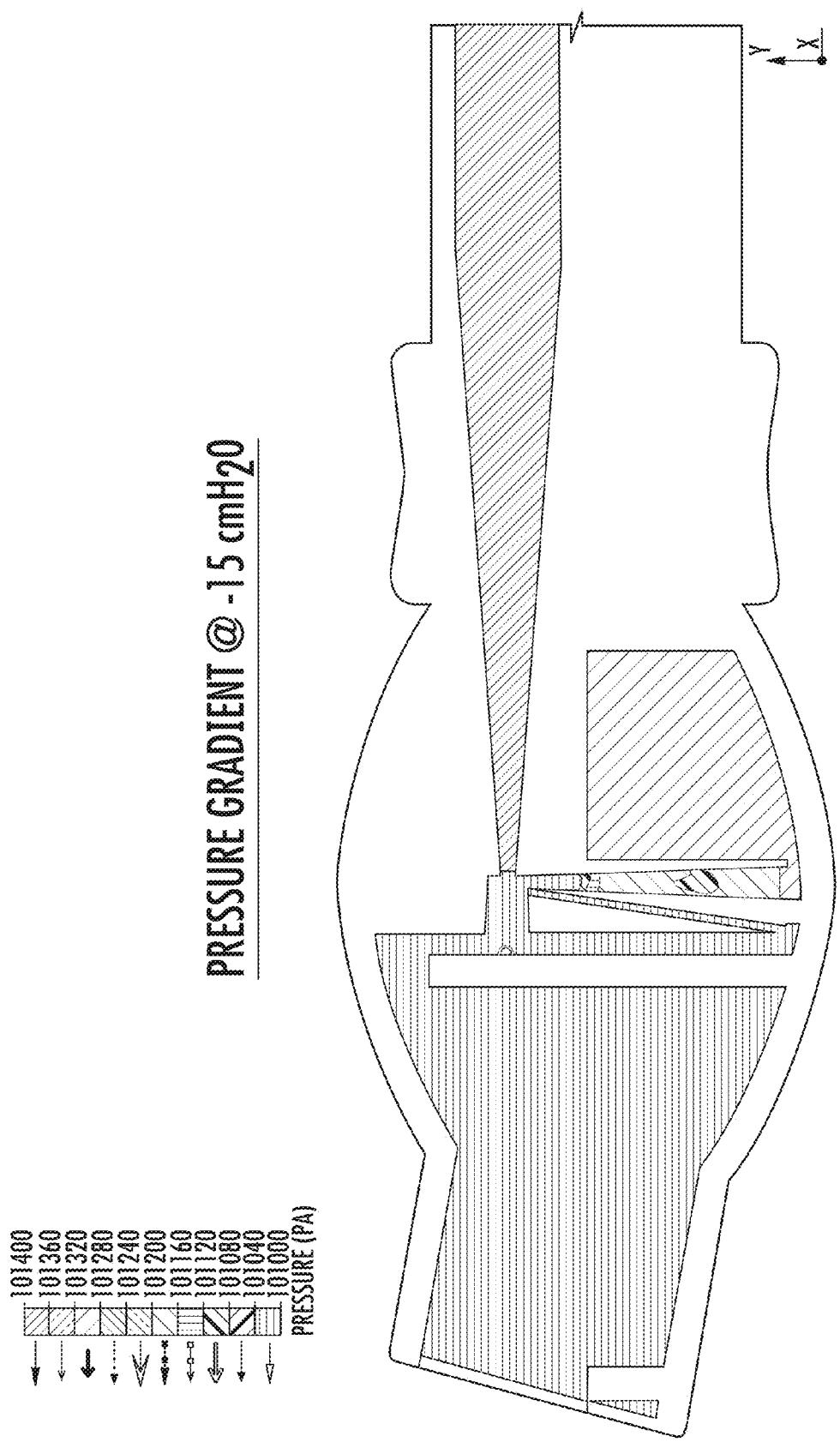
FIG. 12 is a sectional view of the nebulizer of FIG. 1 showing the pressure gradient at −15 $cmH_2O$.
Figure 13:
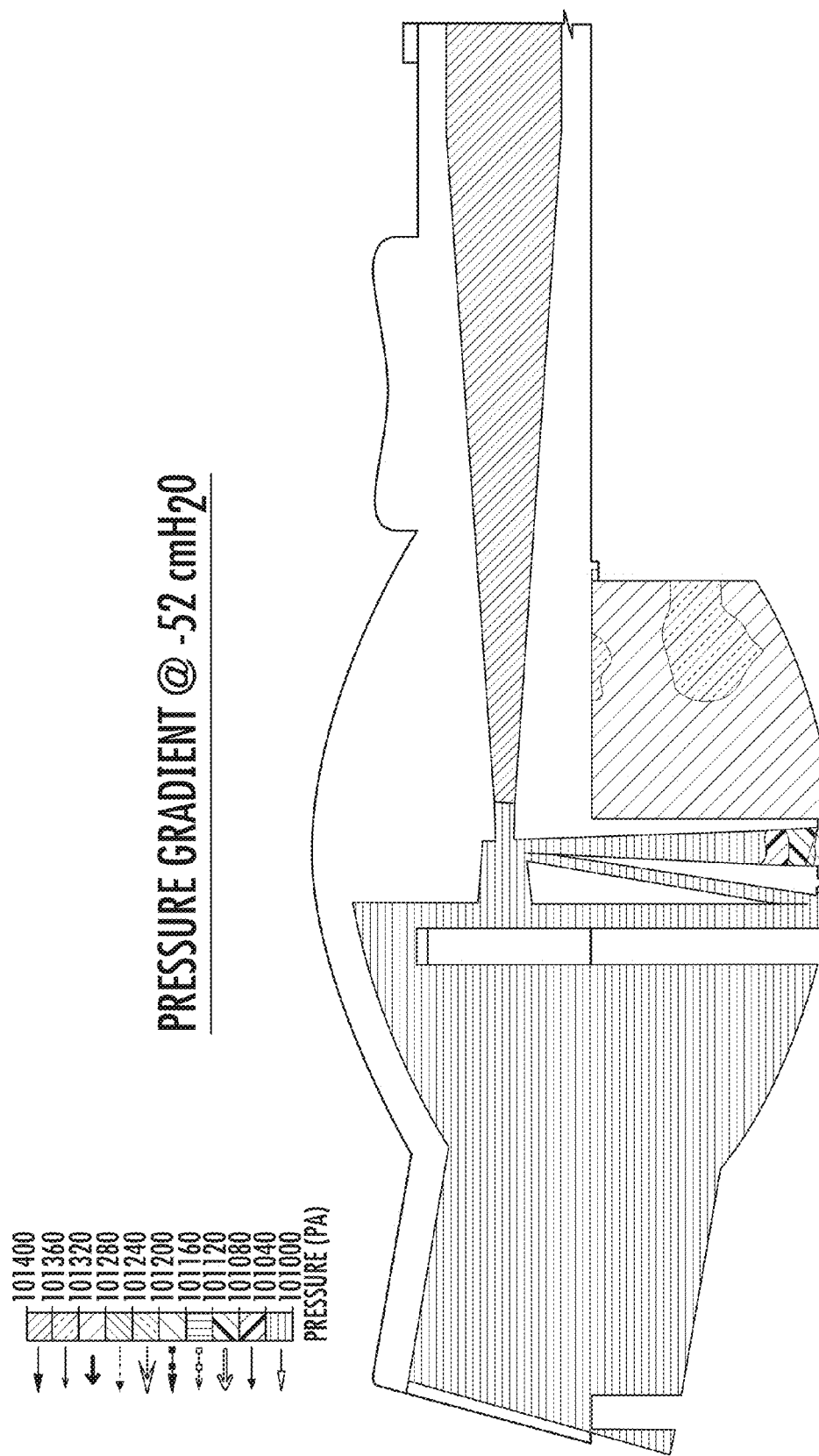
FIG. 13 is a sectional view of the nebulizer of FIG. 1 showing the pressure gradient at −52 $cmH_2O$.
Figure 14:
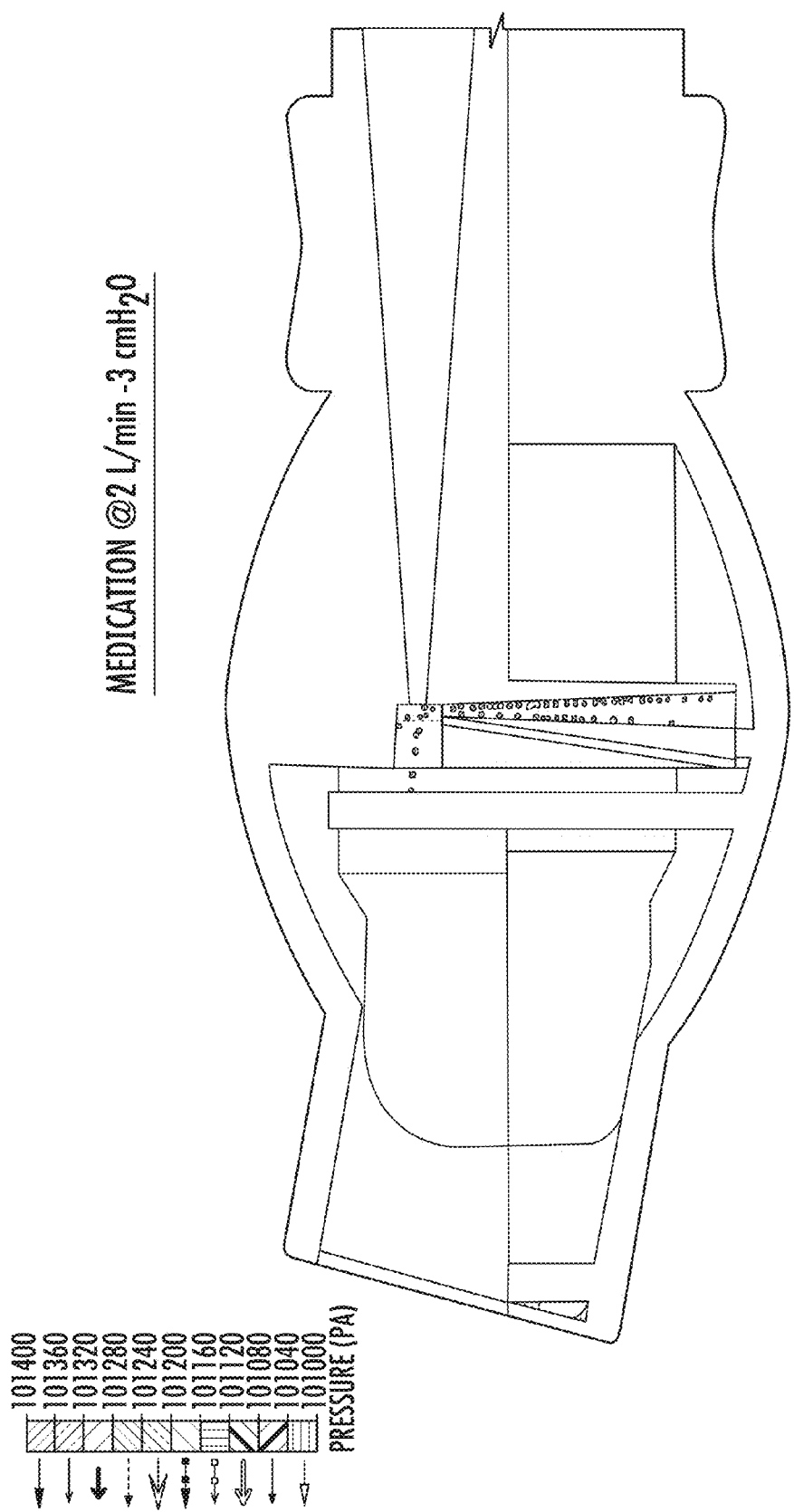
FIG. 14 is a sectional view of the nebulizer of FIG. 1 showing the medication flow upward at 2 L/min −3 $cmH_2O$.

Referring now to FIG. 1, there is disclosed an improved horizontal nebulizer 50 having a nebulizer body 51 with a breath activated venturi nozzle 52 that together with other components creates the differential pressure between the venturi nozzle 52 and the medication reservoir 58 when air is passed through the venturi nozzle 52. The nebulizer body 51 includes an air channel section 54 and medication reservoir 58 and a nebulizer outlet 60 configured to be received within an oral cavity of the patient. The nebulizer body is generally horizontally configured and includes a mouthpiece portion 62. In one embodiment, a pacifier housing 64 is added as shown by the dashed line, to form a pacifier or lollipop configuration at the nebulizer outlet. An air line 66 extends into the air channel section and includes the venturi nozzle 52 that is configured with the air channel section to form at its end a low pressure mixing chamber 68. FIGS. 2 and 3 show in greater detail the air line 66 and venturi nozzle 52 that are configured with the air channel section to form that low pressure mixing chamber, which is somewhat conically shaped.

A primary suction line 70 extends from the medication reservoir 58 to the low pressure mixing chamber 68 through which medication is drawn upward and mixed with air from the venturi nozzle 52 and nebulized for discharge through the nebulizer outlet 60. A compressed air line 72 can connect to the end of the body via an appropriate fitting 74. The venturi nozzle 52, low pressure mixing chamber 68 and air channel section 54 are configured such that at standard temperature and pressure (STP), a differential pressure results in no medication that is drawn upward through the primary suction line 70 for atomization, and none discharged through the nebulizer outlet, until a negative inspiratory pressure is created from inhalation by a user.

Figure 26:
FIG. 26 is a fragmentary plan view of a handheld processing device that can be used in conjunction with the nebulizers having the airflow sensors and which can be configured to wirelessly receive data containing air flow measurements, such as for measuring and processing data regarding the involuntary cough event.

As explained below, nebulization begins at a negative expiratory pressure from about −3 cmH$_2$O to about −52 cmH$_2$O. The venturi nozzle 52 is positioned at a location to be placed within a patient's oral cavity when the nebulizer in use and received in the mouth of the user. As illustrated, a rainfall chamber 76 is formed within the body 51 at the air channel section 54 into which the venturi nozzle 52 and low pressure mixing chamber are formed. As further illustrated, a diffuser 78 acts an impactor upon which the nebulized medication and air exiting the venturi nozzle and low pressure mixing chamber impacts to aid in nebulization. A secondary suction line 80 is formed within the rainfall chamber 76 and draws nebulized medication that had dropped down after impacting the diffuser or impactor. A better view of the secondary suction line is shown in FIGS. 2 and 3. In another example, an airflow sensor 82 can be positioned within the air channel section at the nebulizer outlet and configured to generate signals 83 indicative of air flow generated by a patient's involuntary cough event occurring at nebulization. A processor 84 could be associated with the nebulizer or a separate unit such as a handheld unit as shown in FIG. 26. This processor can receive signals and evaluate the involuntary cough event as explained in greater detail below.

The dashed lines in FIG. 1 show that the nebulizer outlet can be configured as a infant pacifier and be formed as a housing or lollipop. In another example, it is possible for a housing to enclose the body and have an end adjacent to the nebulizer outlet configured as an infant pacifier such as shown relative to FIGS. 21 and 22.

When the nebulizer is operating at a flow condition and at standard atmospheric pressure (STP), the differential pressures cause no fluid flow from the medication reservoir upward through the primary suction line into the low pressure mixing chamber. As the pressure decreases within the nebulizer due to inhalation, i.e., resulting from the negative inspiratory pressure, the differential pressure results in medication flowing up into the low pressure mixing chamber and air flowing through the venturi nozzle.

There is illustrated the medication reservoir 58 that includes the primary suction line where the medication is drawn up into the low pressure mixing chamber and air flows through the venturi nozzle. The nebulizer includes a breath activated venturi. Although the venturi is positioned for intra-oral use, it is not necessary to be in that position and can be located outside the oral cavity. The medication is released during breath activation as a horizontal nebulizer compared to an updraft style. Various medications could be mixed during the intake cycle. The nebulizer in accordance with a non-limiting example is an improvement over those prior art nebulizers that are actuated by pressing a valve for a user regulator while nebulizing.

In the nebulizer shown in FIG. 1, the flow through the venturi nozzle 52 is not activated until there is a negative inspiratory pressure, such as created from inhalation by the patient. In this nebulizer, air pressure is continuous, but nebulization is not. The rainfall chamber 76 is provided, but at STP, there is no flow of medication. At about −3 cm negative pressure, the negative suction actuates air flow and medication to be drawn upward through the primary suction line. When this occurs, the nebulized solution extends from the low pressure mixing chamber 68 and impacts the diffuser 78, i.e., impactor and some droplets fall to be picked up by the secondary suction line 80. There are no residual drops, condensation or agglomeration of nebulized medication that forms in front of the rain chamber, which could result in poor nebulization and air being drawn in by the patient. It is recirculated as a true nebulized medication.

In one example, the average pressure begins nebulizer operation at −52 cm with a 2 liter a minute flow rate. It is possible to begin flow at −3 cm negative pressure, but that has been found to be too sensitive. In another example, the nebulizer is configured to begin flow at −15 cm corresponding to −1 bar. The venturi nozzle and other components of the nebulizer as shown in FIG. 1 can be designed to begin flow from −3 to −100 cm within the venturi nozzle. The nebulizer is a jet nebulizer that requires the negative inspiratory pressure to allow the venturi to begin operating. The medicine fluid will not pass into the airstream until the flow begins through the venturi nozzle. Air is blowing at rest, but no venturi operation with flow occurs until a negative inspiratory pressure is supplied in front of the venturi nozzle at the air channel section to initiate the venturi effect and draw the medication up into the jet stream at the low pressure mixing chamber. As long as the negative inspiratory pressure is applied, there will be flow. If the negative inspiratory pressure stops, there is no flow. One nebulizer configuration is for a 5 liter per minute air flow, but the nebulizer can be configured for 2 liter up to 15 liter air flow. When the venturi nozzle begins operation, the medication hits the diffuser or impactor and some droplets fall downward and are drawn up by the secondary suction line.

The nebulizer shown in FIG. 1 operates when there is negative inspiratory pressure that activates the air flow through the venturi nozzle and into the low pressure mixing chamber. It does not matter if the venturi nozzle is inside or outside the mouth. It is also not a timed type of nebulizer such as with processor monitored breathing or arranging nebulization based on breathing cycles and valves. With the nebulizer shown in FIG. 1, the patient inhales at a certain amount of pressure and the air flow through the venturi nozzle. In one example, it is one bar corresponding to −15 cm of water. The average may be −53 cm and the first −15 cm could activates flow through the venturi nozzle. When inhalation pressure drops below −15 cm, then flow through a venturi nozzle ceases.

FIG. 17 is a chart showing respiratory pressures for measured and predicted MIP (maximal inspiratory pressure) and MEP (maximal expiratory pressure), as an example with the nebulizer shown in FIG. 1.

FIGS. 2-16 are sectional views of the nebulizer of FIG. 1 and showing the air flow through the nebulizer of FIG. 1 at STP and different pressures as showing the variations in pressure and air flow. A flow of 2 L/min is illustrated in most of the diagrams and pressure gradients are shown at STP and other pressures. These figures also show the pressure gradients and medication flow upward through the primary suction line at different inspiratory pressures. As shown in the various FIGS. 2-16 and FIG. 35, the primary suction line is also tapered as a venturi from the medication reservoir upward to the venturi and low pressure mixing chamber. The design and dimension of the venturi relative to the venturi design of the primary suction line, together with the configuration of the low pressure mixing chamber and air channel section, are dimensioned and connected together such that at standard temperature and pressure (STP), a differential pressure results in no medication being drawn upward through the primary suction line for nebulization and discharge through the nebulizer outlet until a predetermined negative inspiratory pressure is created from inhalation by a user. Upon user inhalation that creates the negative inspiratory pressure, air flow begins through the venturi nozzle and medication is drawn upward through the primary suction line and nebulized by the air flowing through the venturi nozzle to be discharged through the nebulizer outlet. Further details regarding the vent configuration as shown in FIGS. 28-35 and other internal components are now illustrated and explained.

FIGS. 28-35 are other views of the nebulizer 50 such as described at FIGS. 1-16. FIG. 28 shows a side elevation view of the nebulizer 50 with a top screw fitting 90 on the nebulizer body 51 that receives a medication reservoir such as a vial or medicine container that may be screwed onto the fitting 90. Other types of fittings may be used. An internal member (not shown) pierces any medicine container to allow medication from the medicine container to flow into the reservoir.

FIG. 29 is an end elevation view of the nebulizer 50 showing the air line 66 and the vent 92 formed in the nebulizer body 51 that communicates with the air channel section 54 and medication reservoir 58 to vent the air channel section 54 and medication reservoir 58 to outside ambient air. The vent may be formed as a valve. The air line 66 receives continuous pressurized air, but it is low pressure. The vent allows balancing of pressures at STP and with the pressurized air so that upon inhalation of the nebulizer, medicine is nebulized.

FIG. 31 is a fragmentary phantom view of a portion of the nebulizer body 51 showing the vent 92 formed in the nebulizer body and communicating with the air channel section 54 and medication reservoir 58 to vent the air channel section and medication reservoir to outside ambient air. Different vent configurations may be used besides the illustrated example. The communication between the sections in the nebulizer body could be by air channels and similar techniques.

FIG. 32 is a more detailed partial cut-away plan view of the nebulizer body 51 showing the air line 66 extending through the air channel section 54 and including the venturi nozzle 56 and its end configured to form a low pressure mixing chamber 68 and the vent 92 formed in the body and communicating with the air channel section 54 and medication reservoir 58. The rainfall chamber 76 is illustrated such that the vent 92 is configured to vent the air channel section 54 and medication reservoir 58 to atmospheric pressure such that at standard temperature and pressure, a differential pressure results between the venturi nozzle 52 and medication reservoir 58. No medication is drawn upward through the primary suction line for nebulization and discharge through the nebulizer outlet until a negative inspiratory pressure is created from inhalation by a user. FIG. 32 also shows a diffuser or baffle 78 upon which the nebulized medication and air exiting the venturi nozzle and low pressure mixing chamber impacts to aid nebulization at the rainfall chamber. FIGS. 33 and 34 show greater details of the internal structure.

FIG. 35 shows air flow such as the medication from a medication container that may be screwed onto the fitting 90 and passes into the reservoir where it is then drawn into the primary suction line (although no arrows are illustrated in this example in the primary suction line). FIG. 35 also shows the processor 84 that may be used in conjunction with a valve (not shown), that may be part of the air flow line and also to receive measurements from an air flow sensor 82 such as positioned in the outlet. Based upon these measurements, adjustments could be made to the pressure of any gas flowing through the nebulizer from a source such as a continuous air flow line or canister that may be connected such as shown in an example of FIG. 46 and flow and pressure changes made.

The nebulizer described in FIG. 1 can advantageously be used for pediatric patients, such as young children and infants. FIGS. 18 and 19 show a nebulizer 100 in a pacifier configuration in which a rainfall chamber design as disclosed in the commonly assigned and incorporated by reference '306 patent includes an outer housing or body 102 that is configured similar to a pacifier or can be configured similar to a lollipop.

This nebulizer in one example could be designed similar to the nebulizer show in FIG. 1 and be activated by negative inspiratory pressure. In another example such as shown in FIG. 20 of the nebulizer, a pressure sensor 104 positioned at the nebulizer outlet senses negative inspiratory pressure. Upon sensing the negative inhibitory pressure, a signal is transferred back to a processor or controller or switch to operate the nebulizer. In a preferred example, however, the nebulizer shown in FIG. 1 is used, and there is no need to use a sensor with the associated processor. If the configuration of FIG. 1 is used, the negative inspiratory pressure begins the flow through the venturi nozzle and initiates medicine flow and nebulization.

Figure 19:
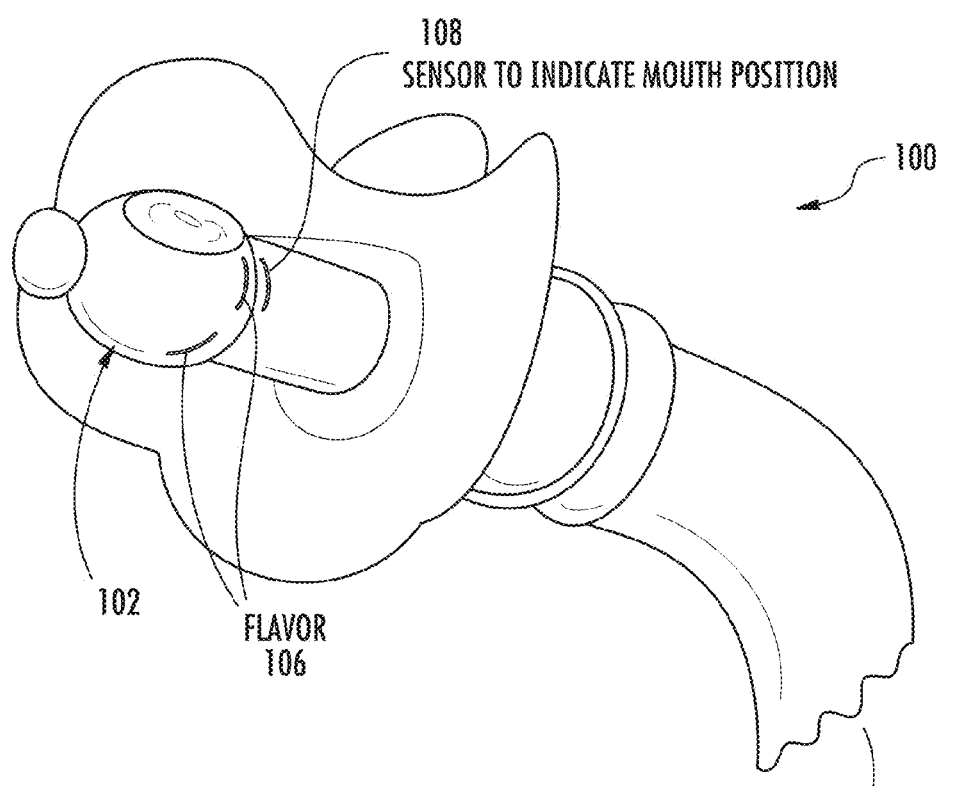
FIG. 19 is a general environmental view of a pediatric nebulizer used by the infant shown in FIG. 18 in accordance with non-limiting examples.
Figure 20:
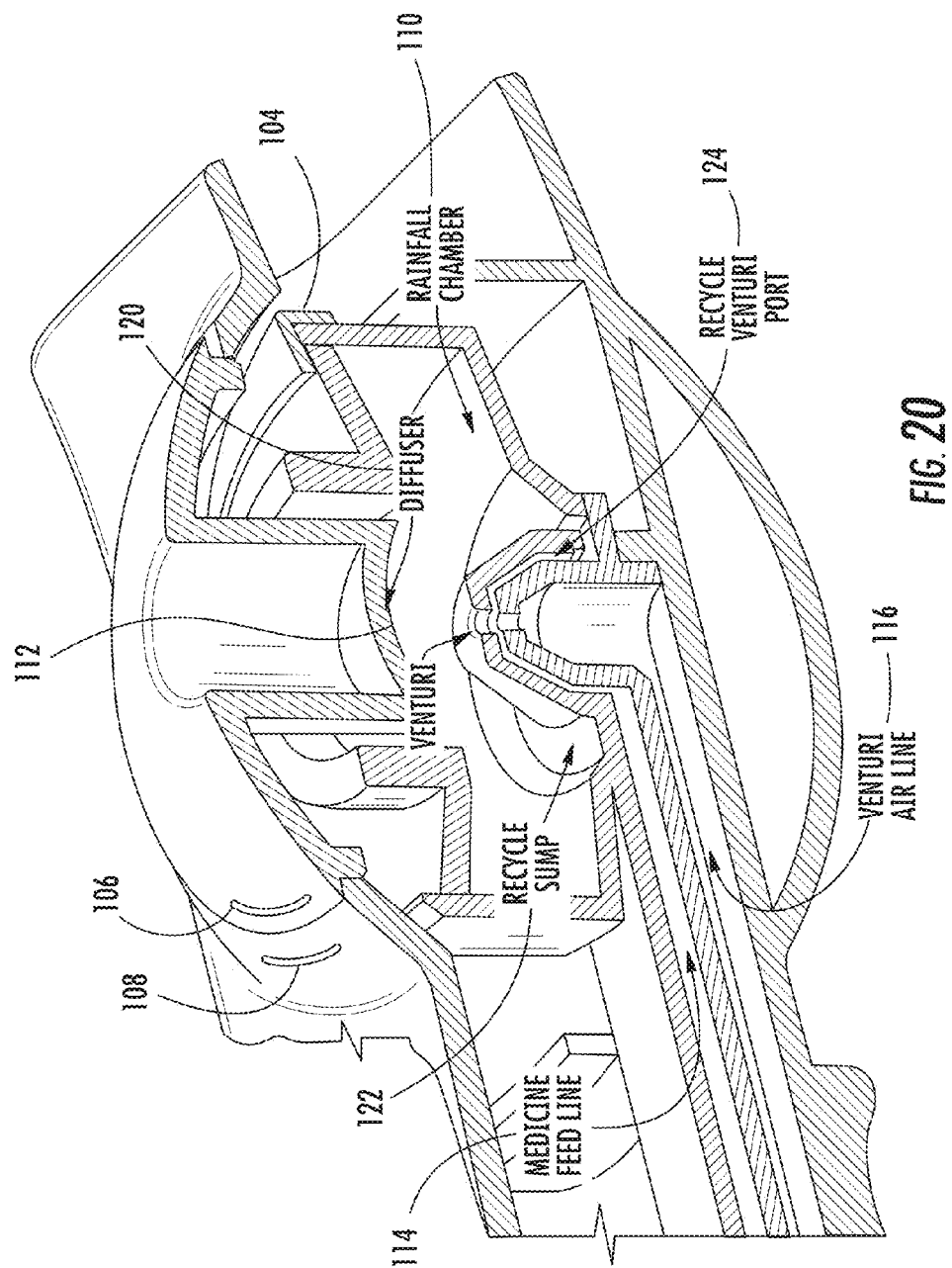
FIG. 20 is a side sectional view in isometric of the pediatric nebulizer shown in FIG. 19 that engages the patient's mouth.

The outer portion of the housing or body of the pacifier section of the nebulizer such as shown in FIGS. 19 and 20 includes a section that has a flavoring 106 and the position sensor 108 to indicate the infant's mouth position. This flavoring section is advantageous for sensor placement when an infant sucks on the pacifier or lollipop configured nebulizer. The infant or child will naturally suck on those areas of the pacifier that have the flavoring, indicative that the infant has positioned the pacifier nebulizer in its mouth in the proper position to allow nebulization to occur. When the infant or child has received the pacifier nebulizer in its the proper position as indicated by the sensor indicating this position, the lips or other portion of the infant's mouth covers the position sensor to indicate the proper mouth position. The position sensor sends a signal back to a controller, for example, to activate the nebulizer for operation. Operation in one example occurs only when the pressure sensor senses the negative inspiratory pressure. In the venturi nozzle design of FIG. 1, however, the negative inspiratory pressure itself begins the air flow through the venturi nozzle and medication to be drawn upward. The controller could actuate a valve to begin air flow, but nebulization would begin only with the negative inspiratory pressure, in one example.

As illustrated, if a nebulizer other than that shown in FIG. 1 is used, the flavoring on the outer portion of the pacifier allows an infant or child to position the pacifier nebulizer in its proper position in its mouth to allow nebulizer operation since the infant or child will naturally position the pacifier in a position where it can sense the flavor. A sugar-free flavoring can be used.

When this occurs, the infant will activate the position sensor that indicates the pacifier is in the proper position in the mouth for full nebulization and it effects. This activates the nebulizer for operation. The other pressure sensor within the intake would sense the negative inspiratory pressure, which then would send a signal back to a processor or controller or switch that is connected to any valves and/or medicine reservoirs and air lines to operate the nebulizer. Valves could open to allow operation in this example.

FIG. 18 shows a configuration in which the pacifier is received within an infant's mouth. The rainfall chamber portion is contained within the nebulizer or lollipop configured body or housing as a nebulizer suction member formed from a flexible material, as shown in FIGS. 19 and 20, while the other sections of the nebulizer such as in the '306 patent, e.g., the medicine reservoir and any other type of medicine containers are contained in a separate housing or body that could be configured similar to a choo-choo train or other infant toy.

Also, the use of more than one medicine container with different medicines can allow simultaneous treatment or delivery of different medicines, actually creating a new drug based upon the combination. It is possible to change the combination depending on infant and child needs. Thus, with the configuration of FIG. 1 an infant can inhale creating the negative inspiratory force to activate the nebulizer, which becomes breath activated in this example. Other configurations can be used where inhalation can cause the nebulizer to open with different valves depending on the design.

FIG. 20 shows a nebulizer configuration such as described in the incorporated by reference '306 patent in which the nebulizer includes the rainfall chamber 110 and venturi 112 and medicine feed lines 114. Although not illustrated, the nebulizer could include a reservoir of medicine and would include at a distal end beyond a medicine port an air intake for an air line feeding the venturi inside the nebulization rainfall chamber. The medicine for the nebulizer can be filled directly into the reservoir or the nebulizer can come preloaded with the medicine. A venturi air line 116 could include a patient air intake port that allows air to be taken in at that port and fed through the body of the nebulizer. A cap could cover a medicine reservoir and be screwed on, snapped on, or otherwise locked on. The cap could be constructed so medicine could be injected into the reservoir through the cap.

FIG. 20 shows the side sectional view of the end of the pediatric nebulizer that engages the patient's mouth in accordance with one aspect of the invention, showing in more detail the rainfall chamber 110 and the venturi 112 and medicine feed lines 114. The venturi nozzle is approximately in the center of the illustration. Right beneath the venturi nozzle is a chamber which is fed by a venturi air line, indicated at the lower portion of the figure to the left of the venturi chamber. Parallel to the venturi air line and located somewhat displaced above the venturi air line is the medicine feed line 114. Medicine from the reservoir flows through the medicine feed line and through a relatively small opening just prior to the venturi in order to dispense medication into the air flow of the venturi. The venturi effect causes a reduction in pressure which causes the medicine to flow from the reservoir through the medicine feed line and into the venturi space where it is mixed with the air in traditional venturi fashion. The medicine that is nebulized by action of the venturi is expelled from the venturi port in an upward direction toward the diffuser 120. The diffuser in this case, is shown as textured. It is not necessary that it be textured but texturing may facilitate the break up of the droplets from the venturi into smaller sizes. As the droplets from the venturi bounce off the diffuser and break up, the sizes may not be totally uniform. The air pressure, the feed rate, the velocity with which droplets impact the diffuser and other well known factors can facilitate production of droplets of desired sizes. In fact, droplets can be generated utilizing this arrangement in sizes less than 0.1 microns. Nevertheless, larger droplets may coalesce as they diffuse throughout the rainfall chamber space. As droplets coalesce, they become larger and fall toward the bottom of the chamber where medication that is not utilized is gathered in a recycle sump 122. Medication found in the recycle sump, is recycled through the recycle venturi port 124 to the proximity with the venturi intake to be reutilized. In this manner, very little medication is wasted and the amount of medication delivered to the patient can be tightly controlled.

When the infant places his mouth on the patient inhale port, air from the infant inhale air path will circulate over the rainfall chamber and around the diffuser causing the extraction of droplets from the rainfall chamber for delivery to the patient. The patient inhale air path may go not only over the rainfall chamber but around it to either side with the actual sizing depending upon the need for the amount of air flow to be delivered to the patient during administration of medication.

Dose reliability and reproducibility is enhanced by using unit dose medicine containers. High lung-deposition efficiency is vastly improved over the prior art because the venturi is located near or preferably inside the oral cavity. Very fine particles can be produced in accordance with the invention.

Figure 20A:
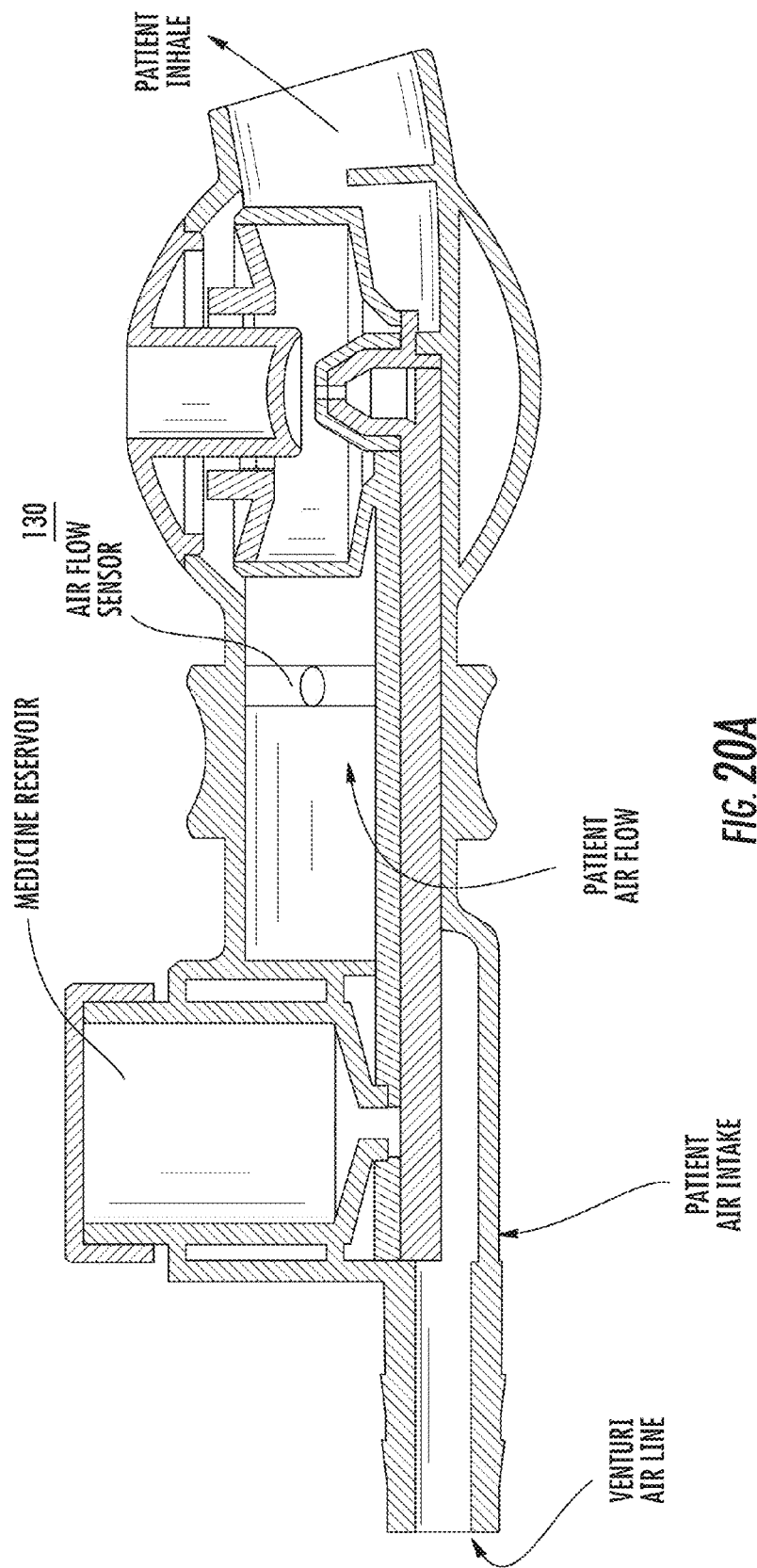
FIG. 20A is a more detailed view of the pediatric nebulizer body with the rainfall chamber, which includes an airflow sensor in accordance with non-limiting examples.
Figure 23:
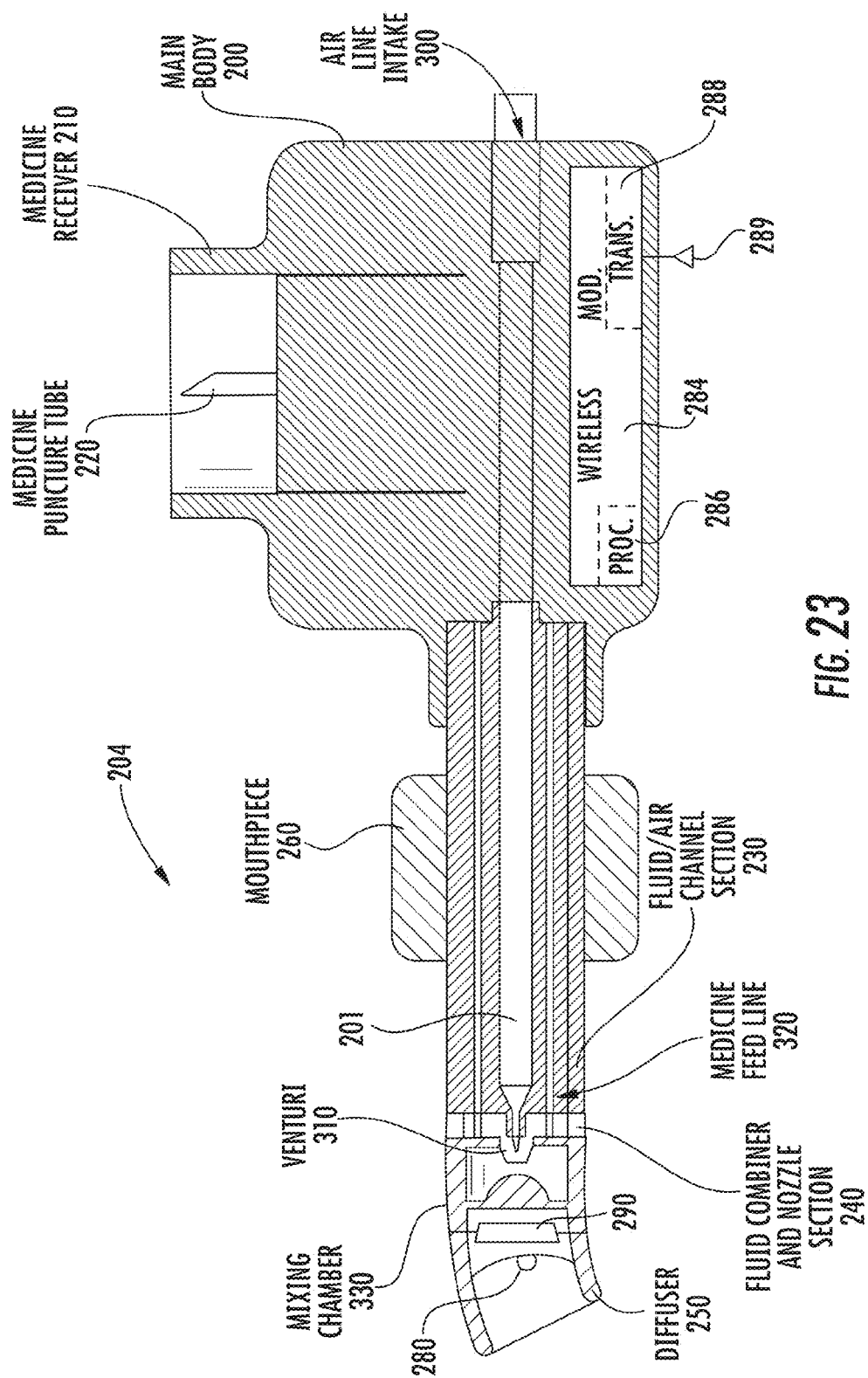
FIG. 23 is a sectional view of another embodiment of the nebulizer in accordance with a non-limiting example and showing an airflow sensor such as a spinning fan wheel and associated with the main body, and a wireless module that includes a processor and transceiver that can receive measured airflow and wirelessly transmit data containing measured airflow to a separate device such as a handheld processing device in accordance with the non-limiting example.

FIG. 20A shows a more complete view of the nebulizer as shown in FIG. 20, which also includes an air flow sensor 130 within the patient air flow channel. The pediatric nebulizer that incorporates this design could include air flow sensing ability to determine the capabilities of the infant as to one capacity and other details, but also give an indication of response, if necessary, to an involuntary reflex cough test. The air flow sensor could be connected by a wireless interface with a processor and transceiver such as shown in FIG. 23 and described below. Thus, functional components as shown relative to FIG. 23 can also be included in the nebulizer such as shown at FIG. 20A.

Figure 21:
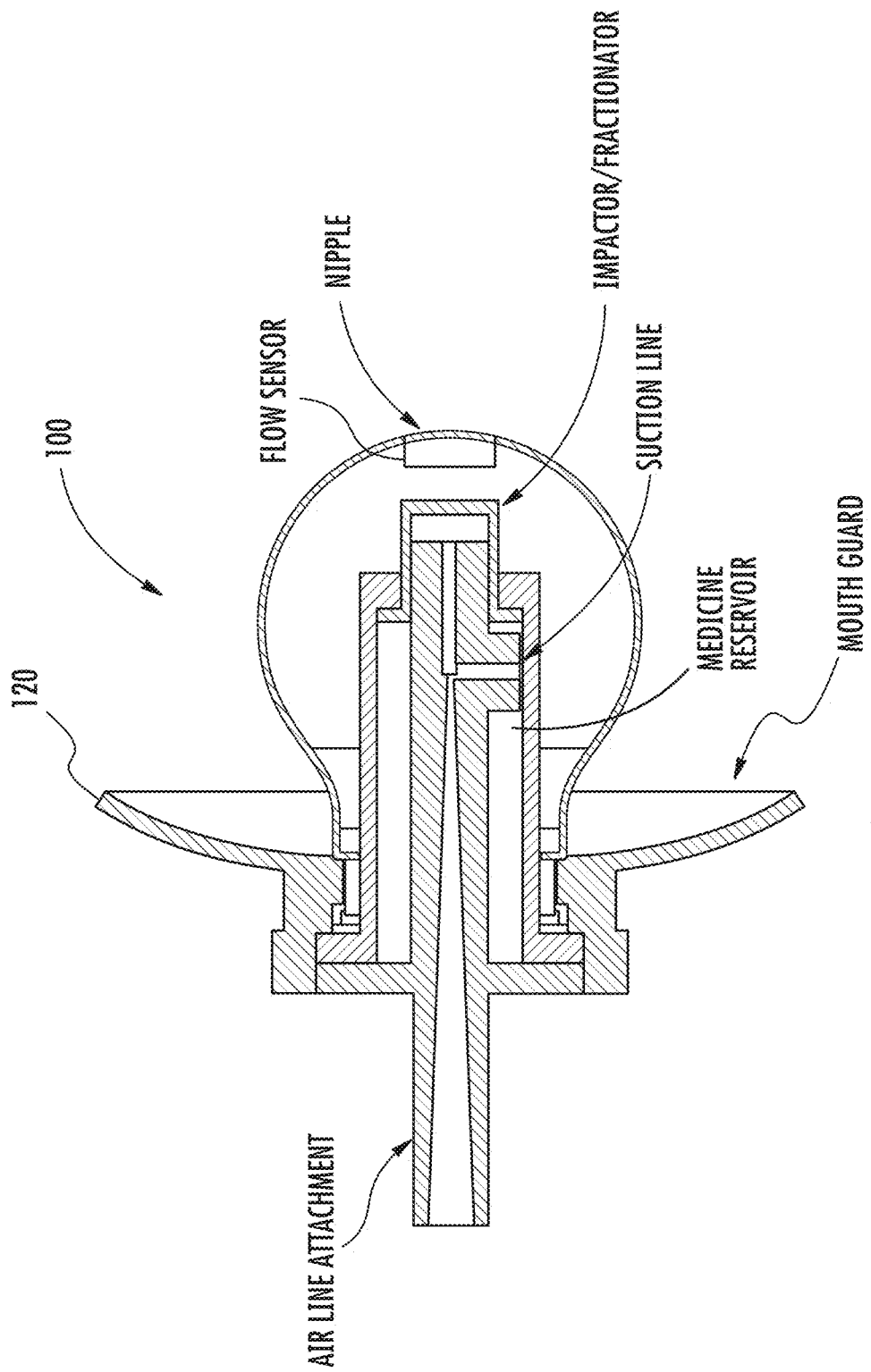
FIG. 21 is another side sectional view of a pediatric nebulizer in accordance with non-limiting examples.
Figure 22:
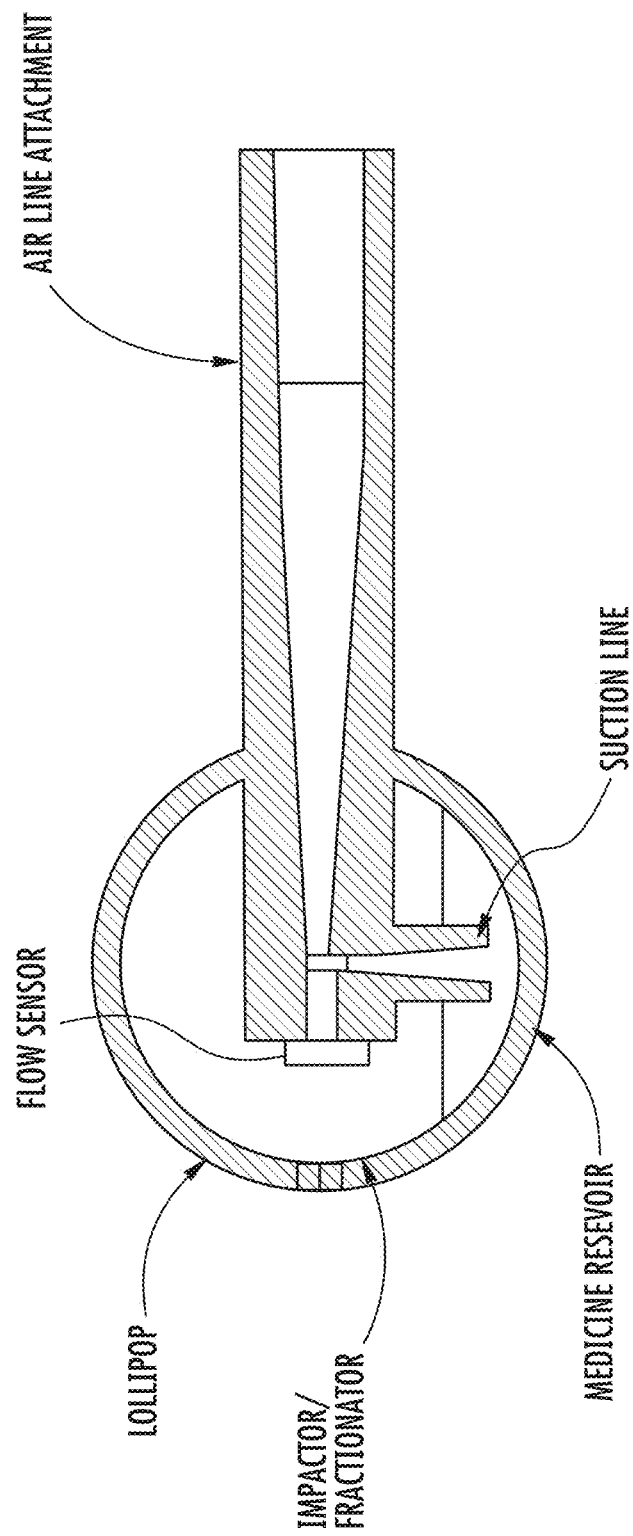
FIG. 22 is another side sectional view of a different embodiment of a pediatric nebulizer in accordance with the non-limiting example.

FIGS. 21 and 22 show other nebulizers configured for pediatric use. The venturi can be designed for breath activation as described before. Although the suction line is illustrated as a primary suction line, it should be understood that a secondary suction line can be used. FIG. 21 shows a nipple configuration and FIG. 22 shows a lollipop configuration.

FIG. 21 shows a different configuration for the nebulizer 100 that includes a mouth guard 110 and a suction line with the air line attachment. A different type of impactor/fractionator is disclosed and the nebulized medicine will impact against the impactor/fractionator and be discharged though the orifice at the nipple. The drops are spread throughout the open area defined by the pacifier housing. In another example, the nebulizer can operate in timed sequence to permit nebulization at specified times. A mouth guard is also illustrated.

FIG. 22 shows a modified lollipop configuration in which the air line attachment is shown in the primary suction line with the interior surface of the lollipop housing forming the impactor/fractionators to create greater fractionation. It is possible to insert a flow meter device such as a fan wheel that can operate to determine air flow for testing purposes. The air flow sensor could be connected to a small processor or communicate with a plug-in in which a handheld device such as shown in FIG. 26 can be plugged into the rear of the lollipop configured nebulizer.

Figure 15:
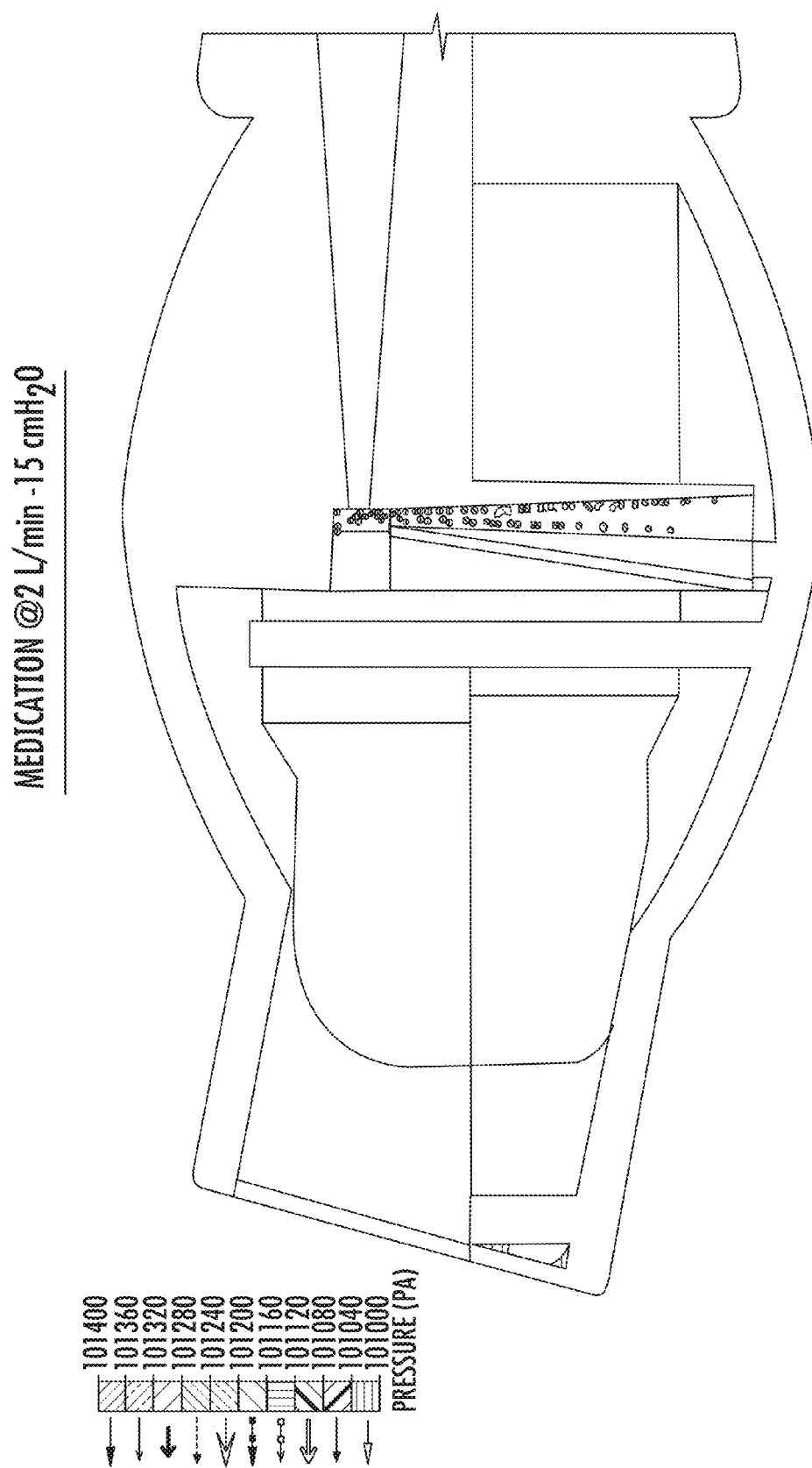
FIG. 15 is a sectional view of the nebulizer of FIG. 1 showing the medication flow upward at 2 L/min −15 $cmH_2O$.

It should also be understood that new medicines can be designed by use of the venturi system. It is possible to preload the drug and form a new drug as a method. The nebulizer could operate as a trihaler or quadhaler. It can be placed in a solution in one container as a new drug and combined with a delivery system. It is possible to form the nebulizer and preload with the drug. Blow, fill and seal technology could be used to form a throw away nebulizer that is used one time. It could be filled and sealed at the manufacturing line. There could be a prefill port of any different shape or form and different types of medication delivery configurations. An example of different configurations for medicine supply as shown in FIGS. 15 and 16 of the commonly assigned U.S. Pat. No. 8,109,266.

The use of a second nozzle or secondary suction line 80 can be advantageous because when condensation or agglomeration occurs, a drug will drop down through gravity feed and be redrawn to aid in mixing especially with preloaded medicine. Thus, the nebulizer shown in FIG. 1 can be formed as a sterile preloaded medicated nebulizer as a throw away device. Multiple new drugs can be developed through mixing with the nebulization and a venturi action.

It is also desirable to incorporate a flow meter function as described in the commonly assigned U.S. Pat. No. 8,109, 266. This incorporated by reference patent application shows two types of flow meter designs that could operate as a clip-on device onto the various nebulizers disclosed and incorporated by referenced patents identified above. Other designs are in-line and are the preferred design with the nebulizer configurations shown in FIG. 1 or any pediatric nebulizers. In one desired design, a spinning wheel is used instead of the designs shown in the incorporated by reference application. In the embodiments described in the instant application, the nebulizer can be used to measure involuntary cough and measure the expiatory flow for the voluntary cough and what is the response. This could be beneficial with the pediatric nebulizer using the pediatric nebulizer for diagnoses. A spinning wheel for some type of spirometers could be incorporated into the nebulizers and used with the C5 stimulus, in which the involuntary cough occurs on the average of 4.8 times (average of 5 times) or 4.8 seconds on an average. The spinning wheel can calibrate a processor to measure peak flow and time over the inspiration and expiration and form a graph. It is possible to form the nebulizer where a button is pressed to activate the nebulizer, resulting in the involuntary cough. A flow sensor can be integrated with the nebulizer measures air flow at the time of the involuntary cough or at the time the button is hit. It is possible to plug the hand held device into the nebulizer as illustrated. The nebulizer device can perform the pulmonary function test (PFT) that is adequate for use with kids, such as using the lollipop nebulizer as shown in FIG. 21. It is possible to measure the velocity of the airflow and draw a graph of the inspiration and expiration over time. The system can draw loop interfaces to the processor or other PC and be compared relative to voluntary cough. During the C5 event it is possible to establish the normal versus the abnormal range.

Reference is made to the commonly assigned and incorporated by reference to U.S. Pat. No. 8,597,184 and U.S. Patent Publication Nos. 2011/0046653 and 2011/0040211, the disclosures which are hereby incorporated by reference in their entirety. It is possible to diagnose GERD and perform other analysis as explained in those incorporated by reference patent applications, including diagnosing stress urinary incontinence and problems with the lower esophageal sphincter.

The flow meter could be formed within an extension as a collar or molded into the nebulizer itself.

There is now described the nebulizers and flow meter sensor relative to FIGS. 23-27, similar to the description taken from the incorporated by reference U.S. Pat. No. 8,109,266.

FIG. 23 shows a nebulizer 204 that includes the main body 200 having an air channel section 201 that is formed by the air line intake 300 and fluid/air channel section 230 and related sections of the main body as illustrated and including a mixing chamber 330 and venturi 310 positioned to be placed within close proximity or within the patient's oral cavity in this non-limiting example and configured to receive medicine and air and mix the medicine and air within the mixing chamber and receive the air flow through the venturi and cause the medicine entering the mixing chamber to be atomized by the action of air flowing through the venturi. In this embodiment, an air flow sensor 280 is associated with the main body, and in this example at diffuser 250, and configured to measure the air flow created by the patient's one of at least inhaling and exhaling air. In this example, the air flow sensor 280 is positioned within the air channel section 330 and as illustrated at the exit side of the mixing chamber within the diffuser such that air flow is measured when the patient is at least one of inhaling and exhaling air through the diffuser in this example.

The air flow sensor 280 senses and measures the air flow and sends a signal through communications signal lines 282

(shown in FIG. 24) back to a wireless module 284 positioned in the main body 200. The wireless module 284 in this example includes a processor 286 and wireless transceiver 288 such that the signals from the air flow sensor 280 are processed and in this example wirelessly transmitted through an antenna 289 (which could be a conformal antenna positioned on the main body 200) to a handheld processing device 560 such as shown in FIG. 26 and with its processing capability illustrated in block diagram at FIG. 27. The outlet at the diffuser on the exit side of the mixing chamber in this example chamber includes an air flow metering valve 290 positioned within the air flow channel and configured to adjust the resistance to air flow to a predetermined level for respiratory exercise training and incentive spirometry use. In this example, the air flow metering valve 290 is formed as a baffle or similar mechanism that can be adjusted to vary the amount of air flow resistance. The adjustment can be indexed such that any adjustment and air flow resistance can be predetermined, for example, using a manual adjustment or servo drive (actuator) for adjusting the valve. The air flow sensor 280 in this non-limiting example is shown as paddle wheel type sensor or could be a flap with actuators, such as MEMS actuator, which inter-operate with a processor to determine air flow adjacent the air flow metering valve 290. The air flow metering valve 290 in an example includes a small drive mechanism such as an actuator attached thereto, allowing adjustments to be made based upon a signal such as from the processor 286 and feedback signal from the air flow sensor to adjust and vary the amount of resistance to air flow for respiratory exercise training and incentive spirometry use. The valve 290 can also in one example be manually adjusted by a patient and include settings to aid in adjustment as noted before.

In a non-limiting example, the handheld processing device 560 is configured to process the measured air flow over time to determine a respiratory function of the patient. This device 560 is also configured in another example to process measured air flow over time to determine a neurological deficiency in a patient based on air flow measurements derived from an involuntary reflex cough. For example, the analysis of the voluntary cough and involuntary reflex cough test is disclosed in commonly assigned U.S. Patent Publication Nos. 2007/0135736; 2007/0255090; 2011/0046653; and 2011/0040211; and U.S. Pat. Nos. 8,597,183; 8,602,987; and 8,597,184, the disclosures which are hereby incorporated by reference in their entirety. These commonly assigned published patent applications and issued patents set forth details of the voluntary cough testing and involuntary reflex cough testing in which the nebulizer as described in the instant application can be used to aid in the type of testing as set forth in those incorporated by reference applications. Such testing is advantageously used to diagnose stress urinary incontinence or problems in the lower-esophageal sphincter as a non-limiting example.

Figure 25:
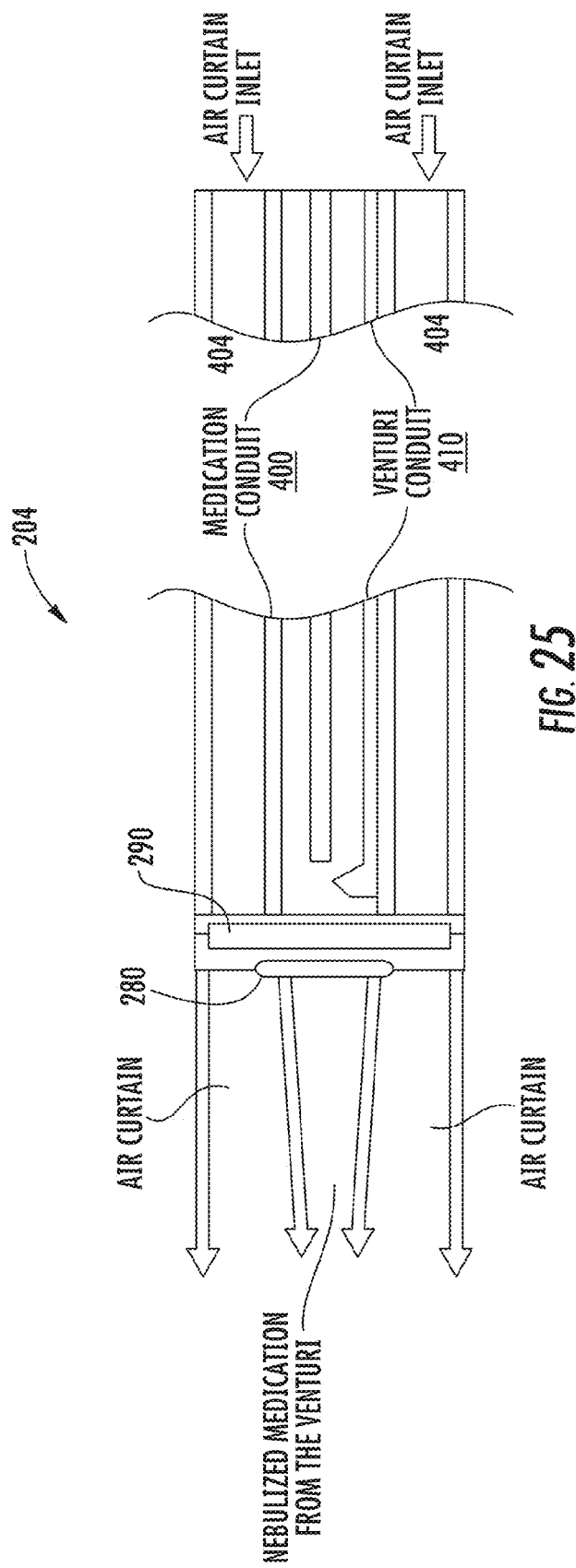
FIG. 25 is a cross-section view of another nebulizer configuration that provides air curtains and showing an air flow sensor mounted at the mixing end of the nebulizer in accordance with the non-limiting example.

FIG. 25 shows a modified nebulizer such as the type disclosed in commonly assigned U.S. Publication No. 2007/0137648, the disclosure which is hereby incorporated by reference in its entirety. This application shows air curtain inlets created by air curtain conduits 404 that are used to supply a curtain of air above and below the nebulized medicine and air passing through medication conduit 400 and to enhance penetration of nebulized medicine into the airway of the patient. The air flow sensor 280 as a paddle wheel type device is positioned at the exit end of the nebulizer 204 as illustrated and in this example includes the air flow metering valve 290 as illustrated and incorporates a manual or automatic adjustment mechanism such as an actuator as may be needed.

It should be understood that different types of air flow sensors 280 can be used besides the illustrated spinning wheel configuration. As disclosed in the incorporated by reference U.S. Pat. No. 8,109,266, it is possible to design the air flow sensor 280 as a mass air flow sensor that converts the amount of air drawn or expelled into and out of the nebulizer into a voltage signal. Different types of mass air flow sensors could be used such as a vane air flow meter, including using any necessary MEMS technology or using a Karmen vortex or a semiconductor based MAF sensor. It is possible to use a hot wire MAF sensor such as a thermistor, platinum hot wire or other electronic control circuit to measure temperature of incoming air, which is maintained at a constant temperature in relation to the thermistor by an electronic control circuit. As heat is lost, electronic control circuitry can compensate by sending more current through the wire. This is only one example. The wire typically will be kept cool enough such that the temperature does not impact a patient. The hot wire can be placed further into the diffuser and/or main body within the air channel. It is also possible to use an Intake Air Temperature (IAT) sensor.

Another possible air flow sensor is a vane air flow meter that includes basic measuring and compensation plates and other potentiometer circuits. In another example, the air flow sensor uses a "cold wire" system where an inductance of a tiny sensor changes with the air mass flow over that sensor as part of an oscillator circuit whose oscillation frequency changes with sensor inductance. In another example, the flow sensor is an electronic membrane placed in the air stream that has a thin film temperature sensor such as printed on an upstream side and another on the downstream side and a heater in the center of the membrane that maintains a constant temperature similar to the hot-wire. Any air flow causes the membrane to cool differently at the upstream side from the downstream side and this difference indicates the mass air flow. MEMS technology can be used such as MEMS sensors. In this type of sensor, a MEMS sensor has a silicon structure and sometimes combined with analog amplification on a microchip. It includes an analog-to-digital converter on a chip in another example and can be fused with analog amplification and the analog-to-digital converters and digital intelligence for linearization and temperature compensation. The MEMS testing in one example is used for an actuator to control the valve 290.

It should be understood that although the air flow sensor is shown located at the discharge end of the nebulizer at the diffuser on the exit side of the mixing chamber, other locations and positions for the air flow sensor or number of air flow sensor members are possible as well as the valve 290.

Figure 24:
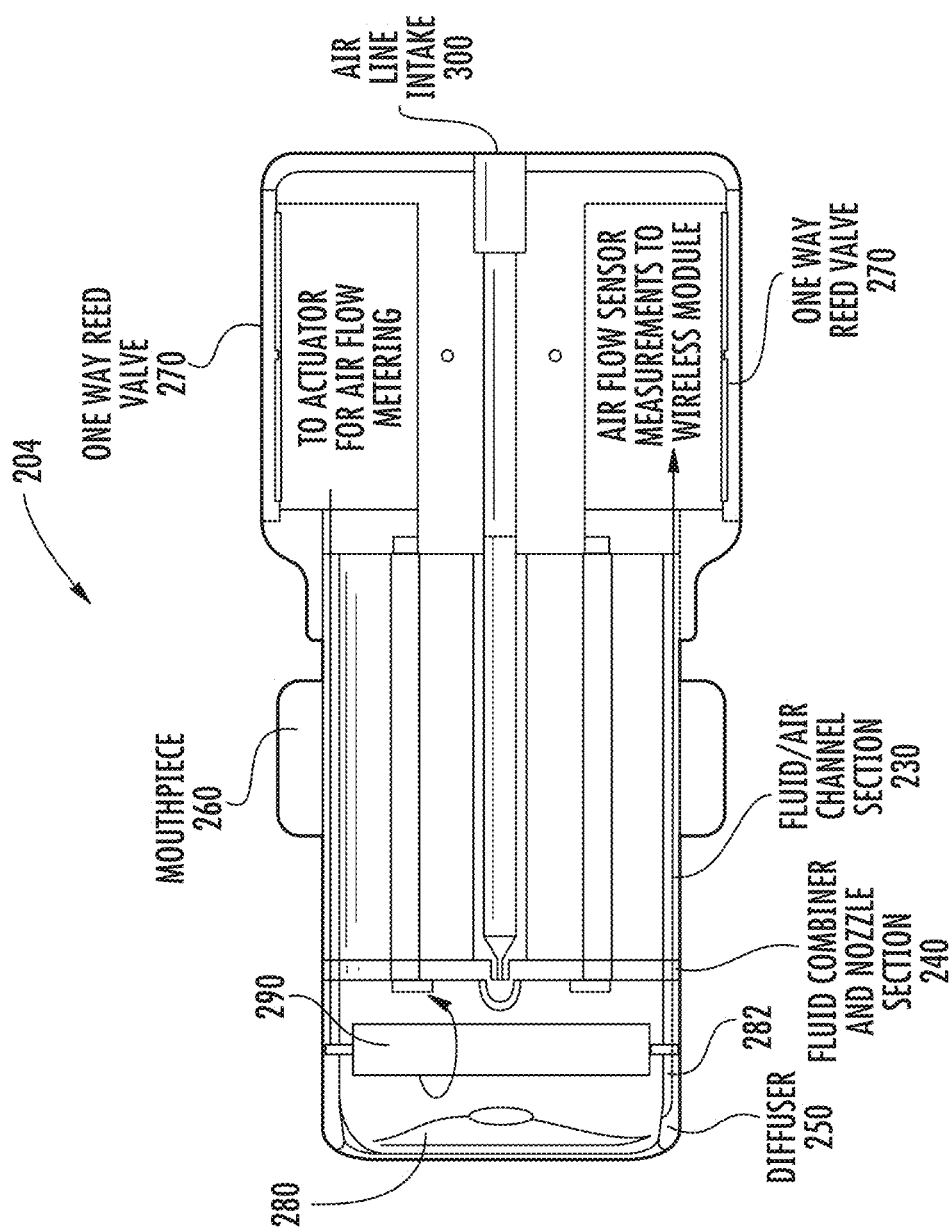
FIG. 24 is a plan view of the nebulizer of FIG. 23 and showing an air flow sensor mounted within the air channel section of that nebulizer.

It should also be understood that the nebulizer using the waterfall chamber as described in incorporated by reference patent publications also in an example has the flow meter function as described and includes the air flow sensor and wireless module as illustrated in FIGS. 23 and 24 and can be positioned in different locations within that device. The air flow sensor can be located at the discharge end on the exit side of the rainfall chamber or other locations in which the air flow can be measured. The valve 290 is also included in another embodiment and includes an actuator in yet another embodiment.

Air flow can be measured in pounds per second (lbs./sec.) and operate for pulmonary function testing calculations and incentive spirometry use. The nebulizer in this example can work as a differential pressure transducer and connect to a pneumotachygraph (or have a self-contained chip with such function) to record the velocity of respired air. It is possible to process associated data as air flow, air pressure, air resistance, and other Pulmonary Function Testing (PFT) results for respired air and data results from voluntary cough (VC) and involuntary reflex cough testing (iRCT). The pulmonary function testing can use spirometry to assess the integrated mechanical function of the lungs, chest wall and respiratory muscles and measure the total volume of air exhaled from a full lung for total lung capacity and empty lungs as residual volume. The Forced Vital Capacity (FVC) can be measured and a forceful exhalation ($FEV_1$) can be repeated. Spirometry can be used to establish baseline lung function, evaluate dyspnia, detect pulmonary disease and monitor effects of therapies used to treat respiratory disease and evaluate respiratory impairment and evaluate the operative risk and perform surveillance for occupational-related lung disease. Pulmonary function testing can be used to determine how much air volume is moved in and out of the lungs and how fast the air in the lungs is moved in and out. This testing can determine the stiffness of the lungs and chest wall for compliance. The flow meter function using the air flow sensor and the associated air flow metering valve together with any processing capability can be used for Inspiratory Muscle Training (IMT) to provide consistent and specific pressures for inspiratory muscle strength and endurance training. The adjustable valve or other adjustable mechanism can ensure consistent resistance and be adjustable such as manually or through microprocessor control for specific pressure settings. It is possible to use the same nebulizer for exercise treatments and therapy and spirometer treatments. The handheld processing device 560 captures the data and can be marketed together with the nebulizer and any necessary catheters for reflex cough testing as a kit. The pneumotachygraph function can be placed in a single chip within the nebulizer or as a separate flow meter device explained below relative to FIG. 25 and connected to the nebulizer. Data containing air flow measurement results can be wirelessly transmitted to the handheld processing device or other processor.

The nebulizer also operates in a non-limiting example as a differential pressure transducer. If the nebulizer is to measure voluntary cough or the involuntary reflex cough, an air channel can be connected to the medicine and gas canister (for tartaric acid in one example) and measure the voluntary cough and involuntary reflex cough for in-phase duration from the time from onset to peak and expulsive phase and in-phase volume such as the duration of the glottic closure as explained in greater detail below. It is also possible to measure in-phase peak flow and the expulsive phase peak flow using such device.

A patient (or clinician or physician) can perform a medical treatment with the nebulizer. It is also possible to operate the flow meter after nebulization to determine if the patient has improved due to the use and administration of the drug such as the tartaric acid. It is possible to measure and graph results through an air flow sensor as part of the flow meter device and transfer data to the handheld device (or other processing device) and measure flow and pressure over time.

FIG. 26 is an illustration of an exemplary handheld processing device 560. More particularly, it should be understood that this handheld processing device 560 can be used by a nurse practitioner or doctor and receive input as wireless signals for flow meter testing as described above. Also, this handheld processing device 560 can incorporate the circuit and functions as disclosed in the various copending and commonly assigned applications identified above. Catheters and other inputs can be connected to this handheld processing device 560 as explained in the above-identified and incorporated by reference patent applications.

Figure 27:
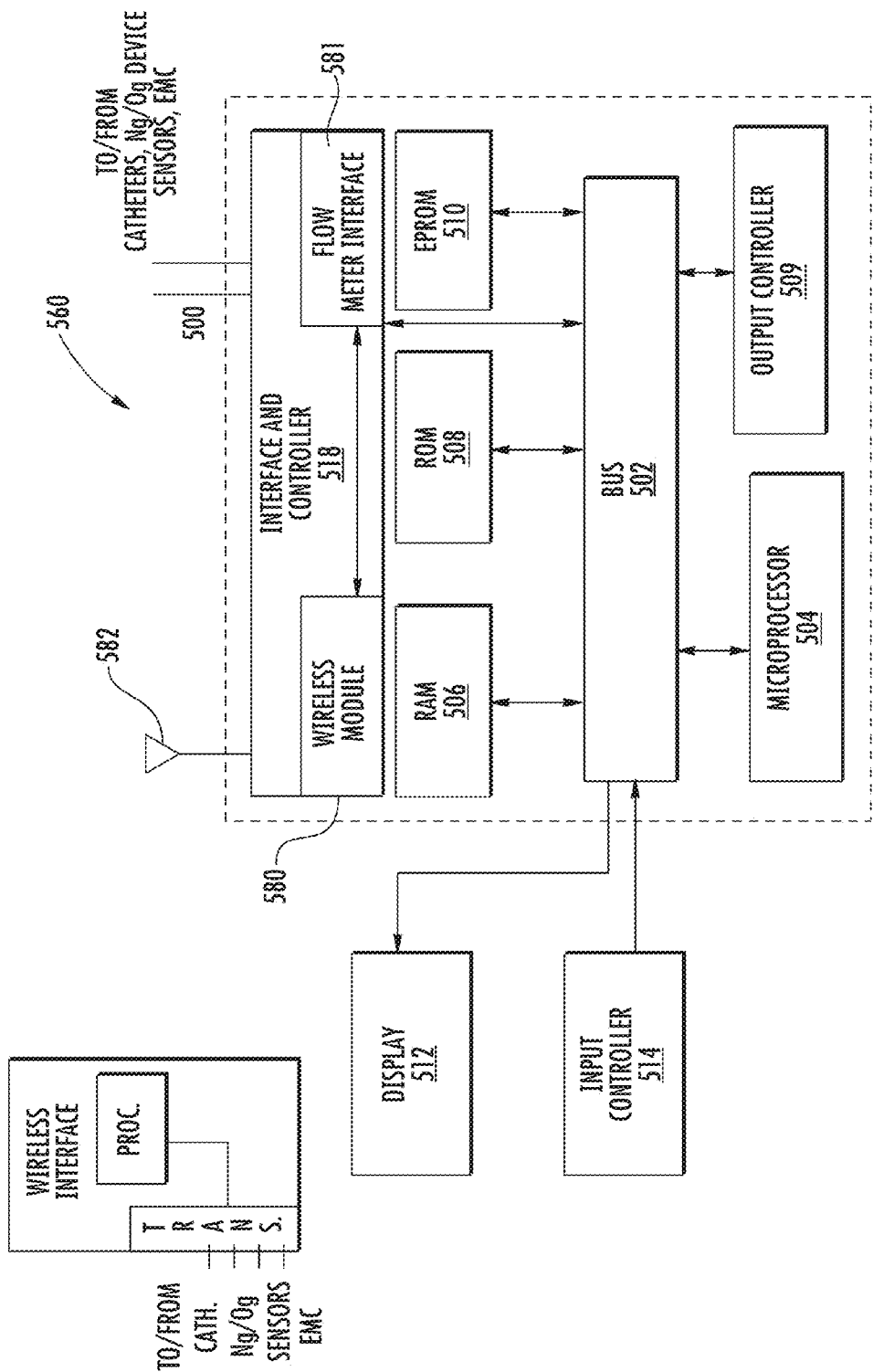
FIG. 27 is a block diagram showing example components of a hand held processing device such as shown in FIG. 26, which can receive data from a nebulizer containing air flow measurements.

FIG. 27 is a block diagram that illustrates a computer system 500 for the handheld processing device 560. Computer system 500 includes a bus 502 or other communication mechanism for communicating information, and a processor 504 coupled with bus 502 for processing information. Computer system 500 also includes a main memory 506, such as a random access memory (RAM) or other dynamic storage device, coupled to bus 502 for storing information and instructions to be executed by processor 504. Main memory 506 also may be used for storing temporary variables or other intermediate information during execution of instructions to be executed by processor 504. Computer system 500 further includes a read only memory (ROM) 508 or other static storage device coupled to bus 502 for storing static information and instructions for processor 504.

Computer system 500 may be coupled via bus 502 to a display 512, such as a LCD, or TFT matrix, for displaying information to a computer user. An input device 514, for example buttons and/or keyboard, is coupled to bus 502 for communicating information and command selections to processor 504. Another type of user input device is cursor control, such as a mouse, a trackball, or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane.

Computer system 500 operates in response to processor 504 executing one or more sequences of instruction. Execution of the sequences of instructions causes processor 504 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 504 for execution. Such a medium may take many forms, including but not limited to, non-volatile media, volatile media, and transmission media. Non-volatile media includes, for example, optical or magnetic disks. Volatile media includes dynamic memory, such as main memory 506. Transmission media includes coaxial cables, copper wire and fiber optics, including the wires that comprise bus 502. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 504 for execution. For example, the instructions may initially be carried on a magnetic disk of a remote computer. The remote computer can load the instructions into its dynamic memory and send the instructions over a telephone line using a modem. A modem local to computer system 500 can receive the data on the telephone line and use an infrared transmitter to convert the data to an infrared signal. An infrared detector can receive the data carried in the infrared signal and appropriate circuitry can place the data on bus 502. Bus 502 carries the data to main memory 506, from which processor 504 retrieves and executes the instructions. The instructions received by main memory 506 may optionally be stored on storage device 510 either before or after execution by processor 504.

The handheld device 560 preferably uses wireless technology that could include infrared (IR), Bluetooth, or RFID technology for communicating with the wireless transceiver in the wireless module of the nebulizer or a separate wireless interface as illustrated. It can be connected directly also. The handheld processing device 560 includes a wireless module 580 that works in conjunction with the pressure transducer interface and controller 518 and the respiratory air flow sensor (flow meter) interface 581 and sends and receives readings through the antenna 582 or other system that could be used. The wireless module 580 could be located at different locations.

There now follows details regarding a particle characterization when the nebulizer as described with FIGS. 1-16 before is used relative to FIGS. 36A-41 and a test set-up and results for nebulizer performance under pulsed flow conditions in FIGS. 42-45B and using the modified nebulizer such as shown in FIG. 46. A description of a metered dose nebulizer is described relative to FIGS. 47-53 and a metered dose atomizer as a modified form of the metered dose nebulizer is shown in FIG. 54. FIG. 55 shows an infant pacifier nebulizer with SNIP capability.

Figure 36A:
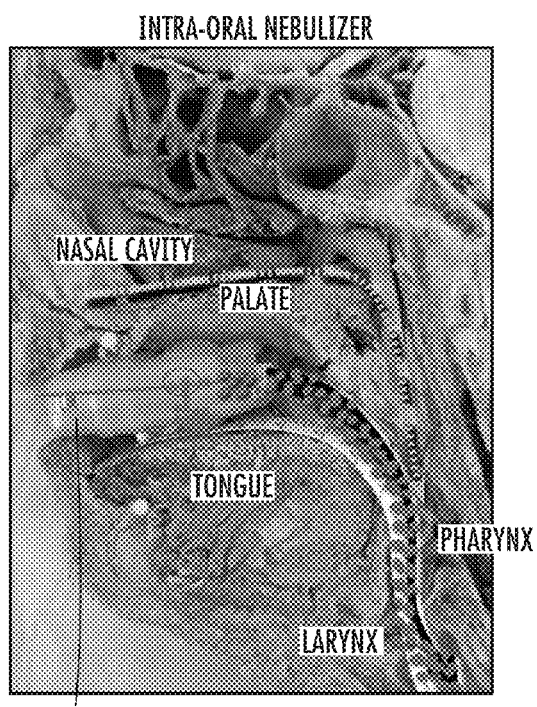
FIG. 36A is an anatomical, sectional view of a patient's oral and nasal passages and showing the positioning in the oral cavity of an intra-oral nebulizer in accordance with a non-limiting example and showing the nebulized medication generated in the mouth and passing into the air passageway.

FIG. 36A shows an anatomical cut-away view with the intra-oral nebulizer 50 such as shown in previous figures in accordance with a non-limiting example and positioned within the oral cavity and showing how aerosol generation occurs in the mouth. Use of the horizontal venturi nozzle allows nebulized medication to travel less distance to the deposition area and permits little condensation, while achieving a targeted Mean Mass Aerodynamic Diameter (MMAD) with a low Geometric Standard Deviation (GSD) such as about 1.5 to about 2.0 at a low residual volume. A mouthpiece from a standard jet nebulizer such as a vertical nebulizer is shown as received in the oral cavity in a comparison anatomical sectional view of FIG. 36B. The drawbacks of such a prior art device are evident and requires significant more surface area and distance to travel to the target with increased flow rates that are required to compensate for this loss. The nebulizer 50 as described is advantageous and allows a shortened drug and device development time and can be used for matched drug and device and novel drug delivery for insulin, HIV, cancer treatments, pulmonary treatment, and pain medications.

Turbulent flows at the orifice intersection as described before cause high aerodynamic shear stress on the medicine and the catastrophic break-up occurs at the primary droplet formation region. Additional impaction may occur within the nozzle prior to exiting towards the baffle or diffuser such as the diffuser 78 shown in FIG. 1 and subsequent drawings. There is a secondary droplet formation as described before and the reduced primary droplet formation decreases the required energy to create a desired particle size after impaction. A large portion of particles will travel past the baffle or diffuser 78 without impaction. Remaining particles will impact the baffle and the velocity of particles will exceed the critical velocity required for splashing to occur.

Figure 36B:
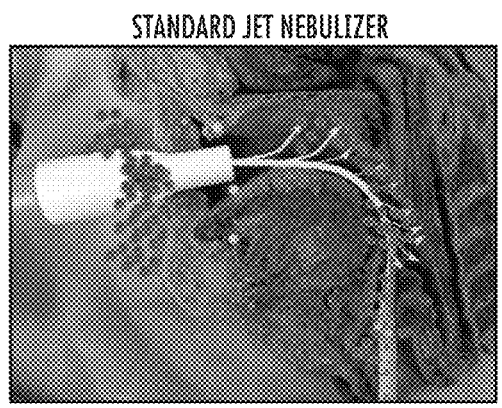
FIG. 36B is another anatomical, sectional view similar to that of FIG. 36A and showing the positioning in the oral cavity of a standard jet nebulizer and showing the nebulized medication generated in the mouth and passing into the air passageway and requiring an increased flow rate as compared to the nebulizer example of FIG. 36A.
Figure 37:
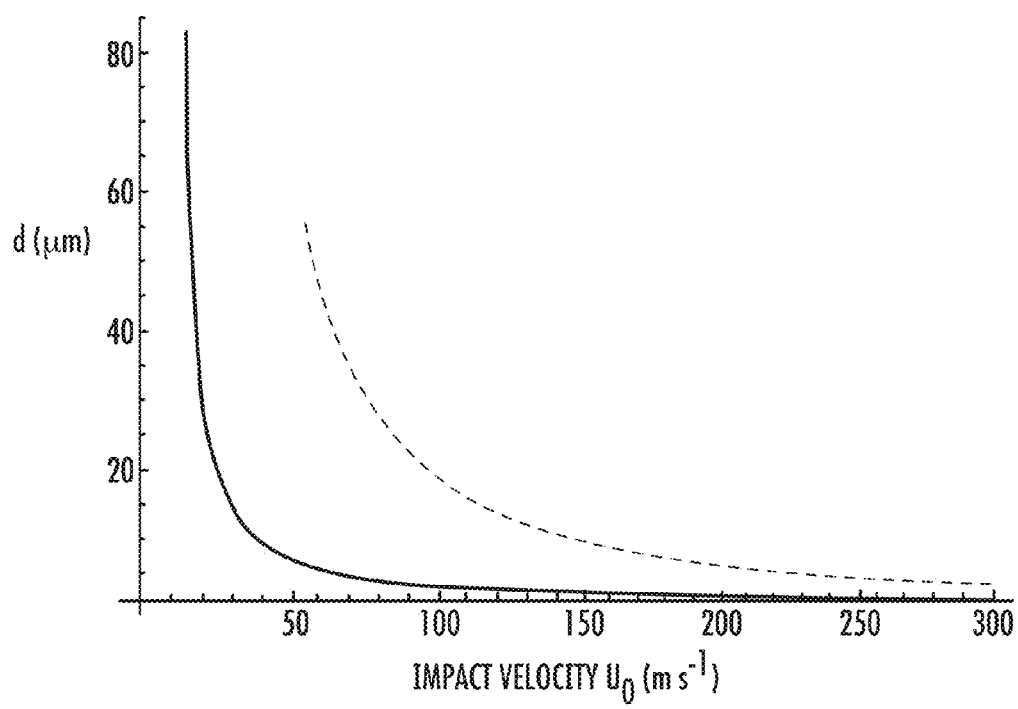
FIG. 37 is a graph related to secondary droplet formation in the nebulizer as described relative to FIGS. 1-16 and showing a critical diameter for splashing to occur on the baffle or impactor of the nebulizer in accordance with a non-limiting example.

FIG. 37 shows a graph of the critical diameter for splashing to occur on the baffle. For example, the horizontal nebulizer 50 as described in accordance with a non-limiting examples in FIG. 1 and subsequent drawings causes additional non-uniform turbulence during the primary droplet formation and allows for the decreased droplet size as compared to more traditional vertical nebulizers such as shown in FIG. 36B that use significant more surface area and require greater distance to travel to the target.

Figure 38:
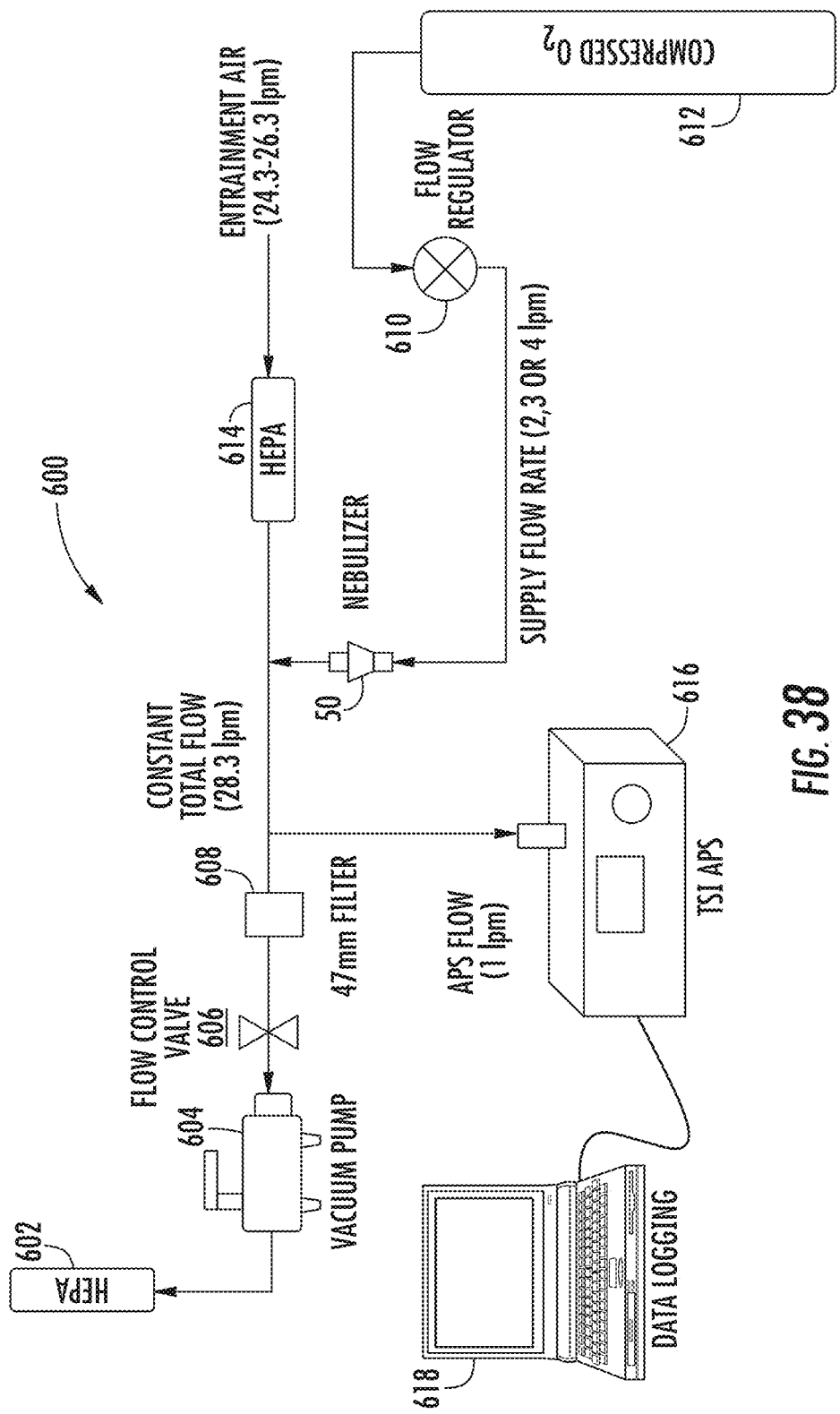

The described nebulizer 50 in accordance with a non-limiting example may operate at lower flow rates of 2-4 liters per minute as compared to 6-8 liters per minute for traditional nebulizers such as the vertical nebulizer example shown in FIG. 36B. The low flow rates offer a small MMAD and GSD (Geometric Standard Deviation) with an equivalent deposition in the lungs with reduced use of medication and less ambient medication exposure. For example, a low density nebulized medication dose allows 70 mg per minute as a non-limiting example. A Design of Experiments (DOE) for the nebulizer 50 was conducted using different nebulizer parameters and the test set-up as shown in FIG. 38 to determine particle size distribution and calculate an average MMAD and GSD during the trials, and show changes in MMAD and GSD during the nebulization process. There was analysis downstream with 47 mm glass fiber filter for the total mass of nebulized albuterol. The testing occurred with different nebulizer configurations and two nozzle variations using a smaller and large diameter and an albuterol sulfate respule (2.5 mg/2.5 ml) and a 500 UL fill for the nebulizer test. The flow rate varied between 2, 3, and 4 liters per minute (LPN), and with the sample of the APS at 12 centimeters distance from the output of the nebulizer. The test was based on the ISO 13320 standard. The MMAD and Particle Size Distribution (PSD) and the test distance were taken into account with intra-oral operation of the nebulizer and USP 90 bend with the Andersen cascade impactor at 12 cm distance. During testing, the delivered medication dosage varied and two nozzle variants as a larger diameter feed orifice and smaller diameter feed orifice were used with the results shown graphically in FIGS. 39 and 40.

Figure 40:
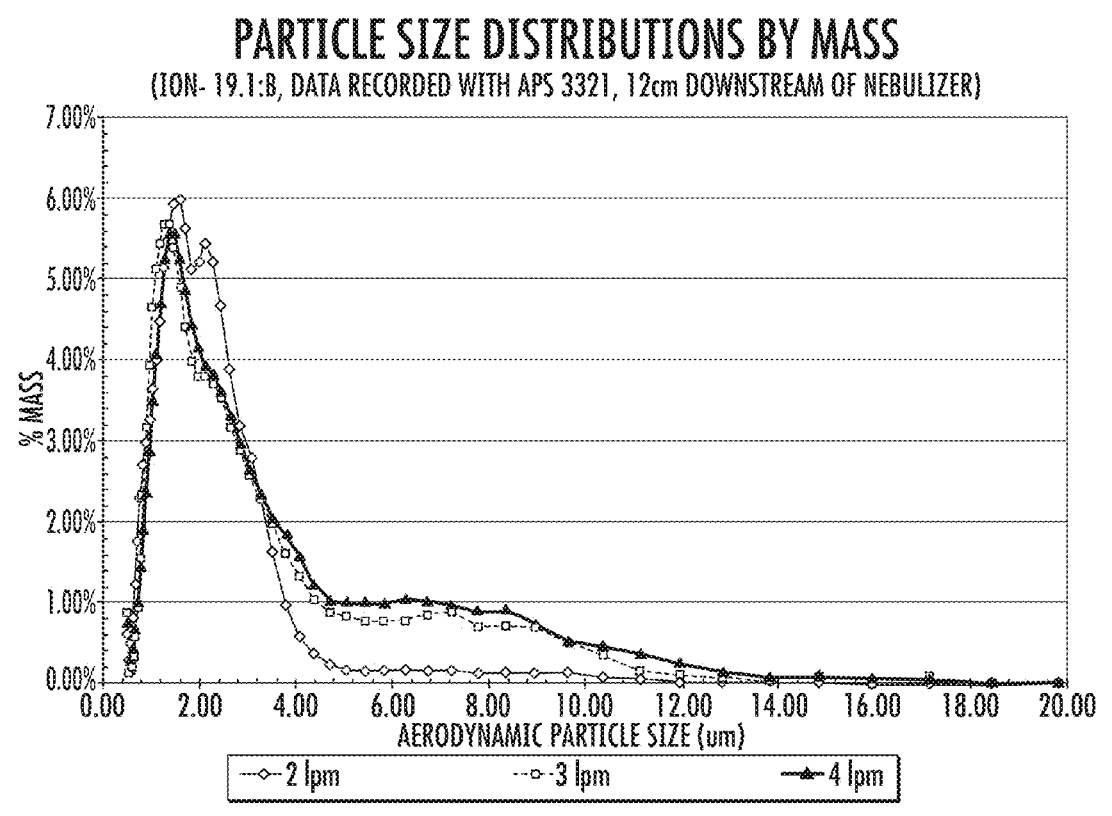
Figure 41:
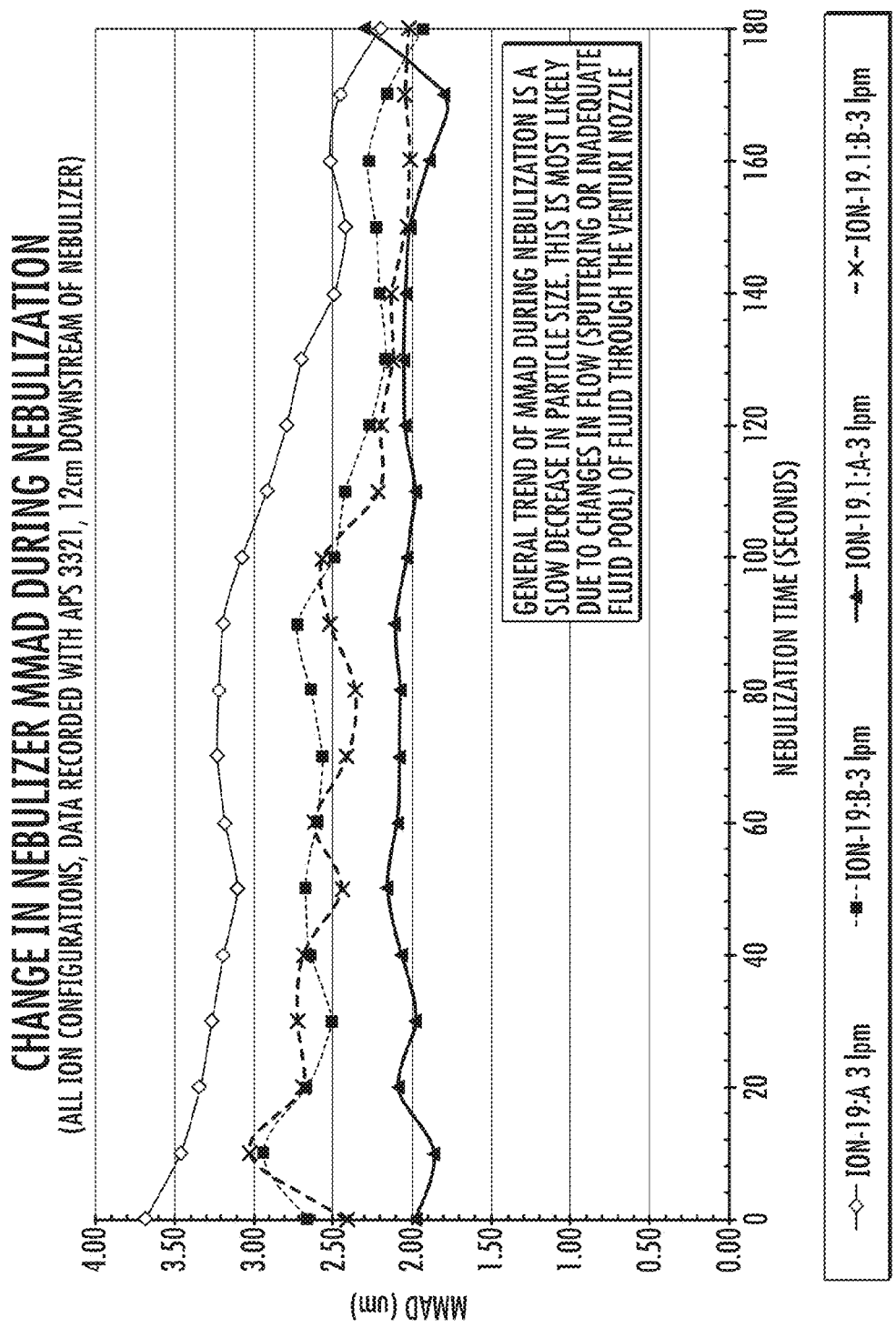

FIG. 38 shows the test set-up 600 and shows a Hepa filter 602 and a vacuum pump 604, flow control valve 606, 47 millimeter filter 608, the nebulizer 50 in-line with a flow regulator 610 and a variable supply flow rate of 2, 3 or 4 liters per minute from canister 612. Entrainment air passes through the Hepa filter with a constant total flow of 28.3 liters per minute as drawn by the vacuum pump and controlled by the flow control valve. The Aerodynamic Particle Sizer (APS) 616 flow was 1 liter per minute and provided by TSI Group with data logging 618. Compressed oxygen from the canister 612 provided the air flow through the flow regulator 610. The air flow rate was held constant for all trials at 28.3 liters per minute. The nebulizer air feed from the canister 612 was a research grade oxygen. The Aerodynamic Particle Sizer 616 was an APS Model 3321 to obtain the particle size data with a capture filter used for total aerosol output. The filter was analyzed via a Beckman Coulter DU800 scanning UV spectrophotometer with a four point calibration standard for albuterol. The results are shown in the graphs of FIGS. 39-41.

Figure 39:
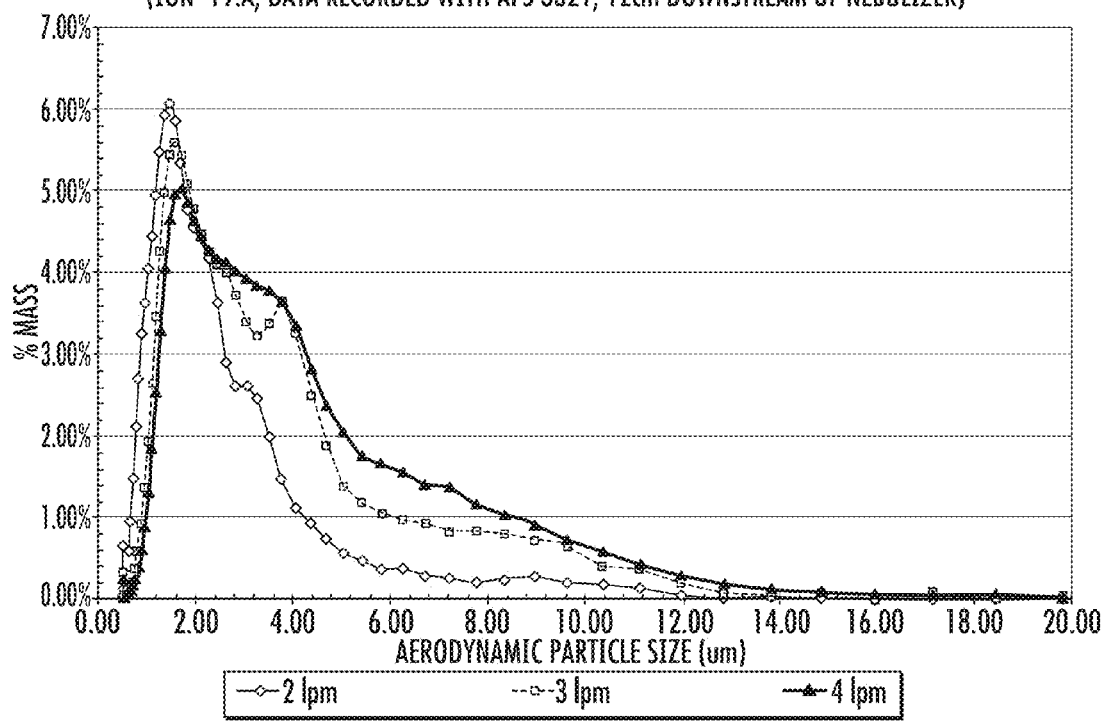

FIG. 39 shows a particle size distribution by mass for a larger diameter feed orifice nebulizer listed as the ION-19:A example nebulizer and showing results for flows of 2, 3 and 4 liters per minute. FIG. 40 is another example similar to that shown in FIG. 39, but for a smaller diameter feed orifice nebulizer listed as the ION 19.lB example nebulizer. FIG. 41 shows a change in nebulizer MMAD during nebulization with the various nebulizers at 3 liters per minute for different configurations with A configuration corresponding to the larger diameter feed orifice and B configuration corresponding to the smaller diameter feed orifice. This graph in FIG. 41 shows that the general trend of the MMAD during nebulization is a slow decrease in particle size such as resulting from changes in flow with sputtering or inadequate fluid pool of fluid through the venturi nozzle.

As indicated from the test results, as the nebulizer flow increases, larger particles escape. Traditionally, as nebulizer flow increases, the shear forces increase and thus produce smaller particles. This is most likely caused by increased turbulence within the nebulizer body allowing larger particles to escape rather than impacting on internal surfaces. The impactions on the wall or flow patterns are most likely reducing a respirable mass output. The results also show that the MMAD increases as flow rate to the nebulizer increases and the MMAD decreases as a function of nebulization time. The GSD increases as the nebulizer flow increases and the GSD increases as a function of nebulization time. The mass output increases with nebulizer flow. In some tested nebulizer variants, the increase in mass from 3 liters per minute to 4 liters per minute is minimal possibly because the nebulizer begins to sputter because of a lack of nebulization fluid. An interpretation is the MMAD increases with nebulizer flow and the particle size data shows that there are larger particles being produced but only at higher flow rates as they are able to escape. Testing with water when the APS sample nozzle is placed in the opening/inside of the nebulizer shows a MAD of around 4 micrometers and the APS suction is pulling out the particle that normally gets trapped. It is possible to change the impaction plate (diffuser) within the nebulizer, which may increase the total mass output. Adding a larger drug reservoir will also increase mass output and should prevent the nebulizer from sputtering in a three-minute treatment.

FIG. 42 is another test set-up 630 to determine the nebulizer 50 performance under pulsed flow conditions using albuterol sulfate. The pulse duration and pulse feed pressure are varied and particle size characterization is obtained for each trial condition. FIG. 42 shows the test set-up similar to that shown in FIG. 38 with common elements of the data logging computer 632, TSI APS 634 and a vacuum pump 636 and compressed air source 638 into the pressure regulator 640. What is different is the location of the vacuum pump 636 as connected to the 47 mm filter 640 into a flow tube 642 with a gauge 644 and the nebulizer connected into the other end of the flow tube from the 47 mm filter. A hand actuated solenoid controller 646 is operatively connected to the solenoid 648 and extends between the nebulizer 50 and pressure regulator 640. The nebulizer 50 was tested with two different pressures at 7.2 PSI and 15.5 PSI and a pulse duration of 0.5 second, 1.0 second, and 2.0 seconds. Albuterol sulfate respules were 2.5 mg/2.5 ml and a 500 UL fill. Data collection occurred and the particle size data was obtained using the TSI aerodynamic particle sizer model 3321 with a sample port 12 cm downstream of the nebulizer. The 47 millimeter absolute filter used for the total drug delivery and analysis occurred via HPLC with a thermo ultimate 3000 nano-HPLC. The test set-up tested multiple feed pressure and pulse durations with the flow tube of approximately 28.3 liters per minute.

FIG. 45B shows a chart of the total delivered drug results and the feed pressures selected based on the equivalent steady state flow at 2 and 3 liters per minute for the nebulizer at 7.2 and 15.5 PSI. Pulse duration as shown in the chart was for 0.5, 1.0 and 2.0 seconds per actuation for the nebulizer with 10 or 20 total actuations depending on the trial and averaged for the nebulizer. In one example, the nebulizer was hand actuated with a metronome used as the timing aid and 0.5 ml (500 MCG) fill of albuterol sulfate per trial for the nebulizer.

Figure 43:
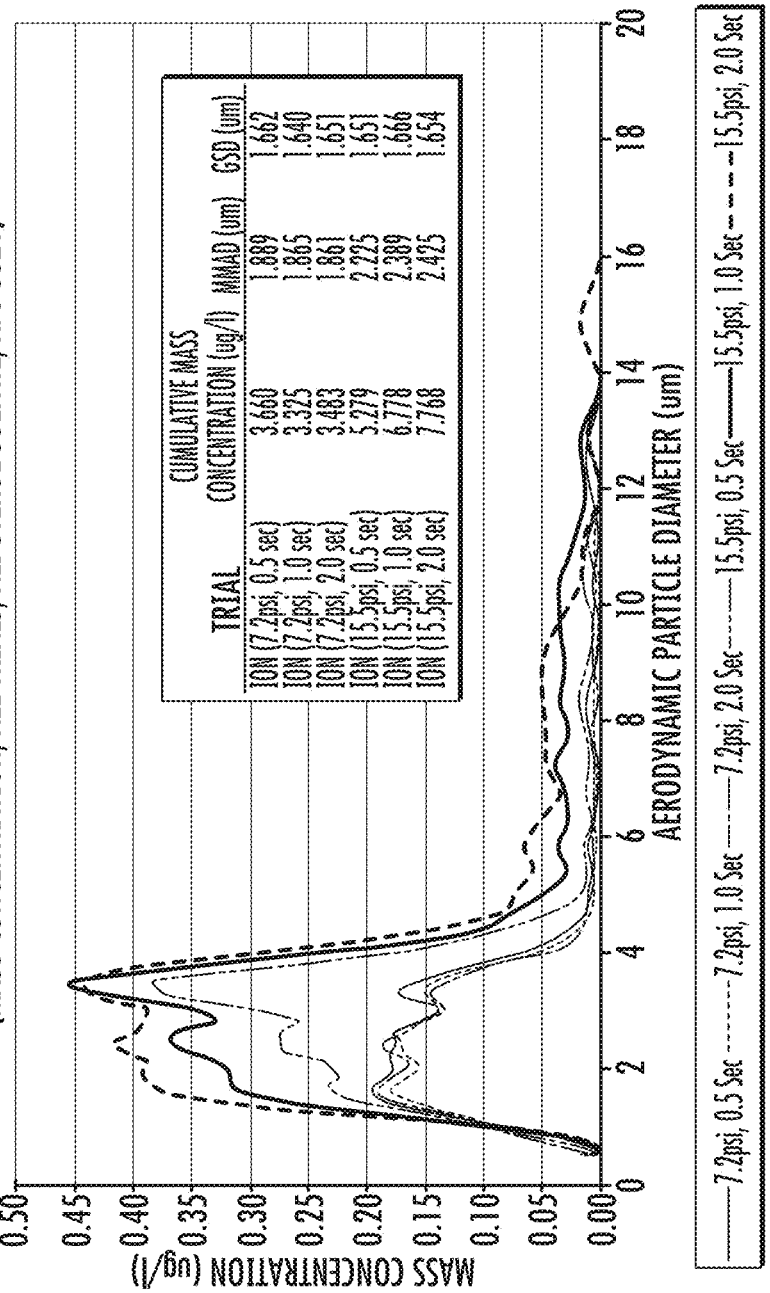

FIG. 43 shows the average peak particle size distribution for all trials and FIG. 44 shows the average peak particle size distribution for the mass concentration and average for each pressure. FIG. 45A shows a bar chart of the delivered drug per actuation. FIG. 45B is a chart showing the total delivered drug results with the nebulizer total delivery having an average total dose of 0.5 to 6.0 micrograms per actuation depending on the pressure and actuation duration. Higher drug concentrations yield the higher dose/actuation values with the albuterol sulfate respule of 1 mg/ml.

FIG. 46 is a modified nebulizer 50' similar to that shown in the side elevation view of FIG. 28, but modified to include a canister 94' as a source of compressed air that connects into a valve 95' to permit pulsed or continuous air flow. Other elements shown in FIG. 46 are common to FIG. 28, but illustrated with a prime notation such as the nebulizer outlet 60', nebulizer body 51', and screw fitting 90'. Different types of valve systems 95' may be used as known to those skilled in the art to provide the pulsed or continuous air. For example, the valve 95' may be adjusted to provide for the range of pressures as described in the total delivered drug results shown in FIG. 45B. Manual or automatic adjustment can be accomplished via manually adjustable controls 96' positioned at the back of the valve as illustrated or such valve 95' can be electronically controlled or pneumatically controlled and use different technologies including a pneumatic or air pulse valve.

FIGS. 47-51 show a non-limiting example of a metered dose nebulizer (MDN) 700 in accordance with a non-limiting example. This nebulizer 700 provides a metered flow of gas at a predetermined pressure and time to provide timed release of gas that may be variable per drug. It still uses a horizontal nebulizer outlet configuration and a horizontal venturi nozzle as best shown in the sectional view of FIG. 50 and the larger exploded, perspective view of FIG. 51, showing the outlet of the nebulizer.

FIG. 47 shows the nebulizer 700 that includes a nebulizer body 702 that is substantially L-shaped and has an air channel section 704, a nebulizer outlet 706 and medication receiver 708 received at the lower or horizontal portion 702a of the L-shaped nebulizer body as best shown in the sectional view of FIG. 50. An air line 710 extends through the air channel section and has an inlet 710a and an outlet 710b and a venturi nozzle 714 positioned at the outlet end 710b of the air line. A medication container 720 is received within the medicine receiver 708 at the lower, horizontal portion 702a as shown in FIGS. 51 and 53. A canister port 722 is positioned at the inlet end 710a of the air line and receives a gas canister 724 as shown in the figures. A valve 725 is positioned at the canister port 722 and actuable to allow a metered flow of compressed gas at a predetermined pressure and time to flow from the gas canister through the air line and venturi nozzle 714.

It should be understood that the valve 725 can be formed similar to the valve shown and described relative to that of FIG. 46 and allow for a pulsed air delivery. A cylindrical receiving sleeve 730 is received within the nebulizer body 702 on the vertical portion 702b formed by the vertically extending portion of the L to securely receive the gas canister in a vertical configuration. The sleeve 730 is dimensioned to allow the gas canister to be slidable therein and includes a bottom sleeve member 732 that engages slidably against the valve 725 via a plunger 732a. As shown in the sectional view of FIG. 50 and the cut-away sectional and perspective view of FIG. 52, a suction line 736 extends from the medication receiver 708 to the venturi nozzle 714 and draws medication upward and mixes it with air passing through the venturi nozzle 714 and nebulizes the medication for discharge through the nebulizer outlet 706.

As best shown in FIG. 52, the venturi nozzle 714 and suction line 736 are formed together and replaceable within the nebulizer body as one unit. For example, the venturi nozzle 714 and suction line 736 may be injection molded to form an integral nozzle and suction line unit as illustrated. The medication receiver 708 includes a top support surface 709. The suction line 736 includes a flange 737 that is seated on the top support surface 709 to support the venturi nozzle and suction line in position within the nebulizer body. The combination venturi nozzle 714 and suction line 736 are received in the outlet and the suction line 736 pressed downward through the top support surface of the medication receiver.

In one example, the medication container 720 is snapped and twisted into place and the gas receiving end of the venturi nozzle received into communication with the air line outlet end 710b as illustrated. As shown in FIG. 50, the gas receiving end of the venturi nozzle 714 is received over the outlet end of the air line 710b in a press fit while the suction line snaps downward into the medication container 720, which includes knob extensions 720a to lock it into place (FIG. 51).

The various components of the nebulizer can be made from injection molded plastic or other materials. The medication container 720 snaps and twist locks into the medicine receiver and snaps into connection with the bottom of the suction line 736 to allow communication with the medication container and draw medication upward through the suction line 736 to the venturi 714. No impactor or diffuser is used in this example since the suction line and venturi are dimensioned and formed together to include respective tapers as illustrated to allow the desired flow of air and medication whether using a continuous or pulsed flow. Because no impactor is required and thus a rainfall chamber is not required. The medication container 720 can be designed to hold a one day, a one month or longer medication supply depending on end user requirements. A secondary suction line is not required with no baffle or impactor.

The nebulizer embodiment shown in FIGS. 47-51 may be press activated by pressing the portable gas canister 724 downward to activate gas flow from the canister through the gas line 710. In the example shown in FIG. 51, the canister is inserted within the sleeve and the bottom sleeve member 732 slid and locked into place. It is also possible to modify a nebulizer to be breath actuated as in the previous examples of the nebulizer described relative to FIGS. 1-18 as long as the valve allows the flow of air where the venturi and nebulizer can be breath actuated. Variable timing is supplied by the valve that extends between the air canister and the air line as best shown in FIG. 50 and described before.

The medicine container 720 may accept liquid solution as opposed to dry powder. The venturi nozzle 714 is interchangeable together with the suction line 736 and can be configured into different designs so that in conjunction with the controlled pressure and velocity of air released through the valve 725, a different nebulized gas is created based upon the timed release of gas, which may be variable for a specific drug. The medicine container that is inserted from the bottom may contain a month's supply of albuterol or just a single dosage depending on the design as an example. It is possible to have a pacifier design as in FIG. 48 (dashed line) with the valve 725 actuated by SNIP.

FIG. 54 is a modified structure of that nebulizer shown in FIG. 51, but formed as a metered dose atomizer in which the front portion corresponding to the horizontal portion of the "L" is modified as an atomizer. A venturi nozzle is still used. The atomizer is formed to allow a mist of medication to be formed as is typical with an atomizer. The valve may also be modified to permit a more variable, metered dose that enhances the atomization of the medication and gas. Many of the other components may remain similar as in the nebulizer embodiment.

The atomizer 800 shown in FIG. 54 is described by using the same reference numerals for common components as in the nebulizer embodiment of FIGS. 47-53, except using the 800 series. The venturi nozzle 814 is positioned at the outlet end 810b at the air line 810 and has a venturi discharge that is oriented horizontally when in use and forms a mixing chamber 811 at its discharge end as illustrated in FIG. 54. A medication receiver 808 is carried by the atomizer body 802 proximal to the venturi nozzle 814 and mixing chamber 811. A suction line 836 extends from the venturi nozzle 814 and mixing chamber 811 to the medication receiver 808 that draws medication upward from the medication container 820 received within the medication receiver and mixes it with gas passing through the venturi nozzle into the mixing chamber and atomizes the medication into a mist. Similar in design to the nebulizer, the atomizer includes an atomizer body 802 that includes the air channel section 804 and atomizer outlet 806. The atomizer outlet 806 is formed as a flared extension 807 in this example.

The atomizer 800 also includes at the mixing chamber 811a diffuser 813 upon which the gas that is mixed with medication in the mixing chamber 811 impacts to aid in forming the mist. As in the nebulizer, a canister port 822 is positioned at the inlet end 810a of the air line 810 and receives a gas canister 824. A valve 825 is positioned at the canister port and actuable to allow a metered flow of gas at a predetermined pressure and time to flow from the gas canister through the air line 810 and venturi nozzle 814. The valve 825 is actuated to deliver gas when pressure is applied downward on the gas canister similar to the nebulizer design. A medication container 820 is received within the medication receiver 808 and the suction line 836 connects into the medication container. The valve actuates a pulsed and metered flow of gas during atomization.

As in the nebulizer 700 embodiment, the atomizer 800 includes a substantially L-shaped atomizer body 802 forming a vertical portion 802b and a horizontal portion 802a. The venturi nozzle 814, mixing chamber 811 and suction line 836 are formed together and replaceable as one unit and supported by the medication receiver 808. The suction line 836 extends through the top support surface 809 of the medication receiver and connects into the medication container received within the medication receiver such as by a snap fit similar to the nebulizer embodiment. The suction line includes its flange 837 that is seated on the top support surface 809 of the medication receiver to support the venturi nozzle 814, mixing chamber 811 and suction line 836 and positioned within the atomizer body. The combination of the integrally formed unit of the venturi nozzle, mixing chamber and suction line can be removed and a different design employed that will generate a different mist and determine what type of mist and particle size could be produced.

It is also possible to use the pediatric nebulizer as disclosed at FIGS. 18 and 19 with SNIP (Sniff Nasal Inspiratory Pressure) as shown in FIG. 55, which interoperates with the nasopharyngeal airstream, which prevents or discourages the drug from hitting the posterior pharynx when released with breath activation. A SNIP sensor could be located in the nose and have feedback to a valve or other mechanism in the nebulizer to allow activation of air flow, such as for later activation by inhalation. The nasopharyngeal airway (NPA) and its oral air flow also aid to pull the drug into the lungs. For example, it may be possible for micro dosages of medicine to be given with nasal respiratory rates in 60's/minute. The pediatric nebulizer could be designed to release every third SNIP. The pressure from the NPA may be used to activate the pediatric pacifier nebulizer to release medicine. The SNIP inspiration pressure may be an aid in medicine delivery. A cough depresses the tongue, which is in the way with medicine inspiration delivery. The nebulizer as disclosed in accordance with a non-limiting example will bypass that obstacle. The SNIP inspiration pressure could activate the release of nebulized medicine.

When using SNIP in a pediatric nebulizer, the frequency modulation of a motor pattern may occur as part of a sensory feedback loop and provide the central pattern generator (sCPG) with information about the phase of the motor behavior. The non-nutritive suck occurs and the SNIP follows, which releases the medicine. The SNIP activation of the pacifier nebulizer is advantageous and confirms the nasopharyngeal airstream significance and when used intranasally with the nozzle/venturi and with a micro feedline. SNIP could activate from the back of the nose and could be advantageous over use of a face mask.

For purpose of technical instruction, there now follows a general description of physiology for the involuntary reflex cough test (iRCT), which activates the Nucleus Ambiguus, which is also disclosed in some of the incorporated by reference patent applications. The nebulizer with the flow sensing function is adapted for measuring both voluntary cough and involuntary reflex cough, such as explained in the incorporated by reference patent applications. The iRCT selectively activates the Medial Motor Cell Column (MMCC) of the spinal cord rather than the (Lateral) LMCC to fire muscles embryologically predetermined to be involuntary cough activated muscles in the pelvis. In the past, urologists did not selectively activate MMCC without overtly activating the LMCC. Magnetic stimulation or electrical spinal cord stimulation activate both cell columns and thus it is not possible to sort out pathology with these. Magnetic stimulation or other approaches from CNS activation set off both columns.

The pelvic muscles that typically are activated with MMCC cough activation include the lumbar-sacral L5/S1 paraspinal axial musculature, which facilitates inpatient continence screening. An example is through MMCC iRCT muscle activation, obtaining L5/S1 paraspinal firing but not L5/S1 lateral gastrocnemius activation because the gastroc muscles are limb muscles activated primarily through the LMCC.

The L-S paraspinals are easier to access with a large pad placed above the sacrum on the midline that contains active, reference and ground combined. It is not important to determine lateralization of the activity like needle EMG for radiculopathy, but only if activation occurs reflexively where the onset latency is under the pressure activation of the abdomen such as the Levator Ani. This is a poor muscle for these purposes because people train it to activate and set their pelvis if the person senses any intra-abdominal pressure elevation. Also, it is difficult to get pads to stick to that area with hair, perspiration, fungal infections or bowel/bladder incontinence present, and other factors.

Some examples have been developed and studied, including a normal CNS patient with Lumax bladder and bowel catheters and pads at L5/S1 paraspinals and a separate EMG machine and electrodes at the pelvic floor in a standard 3:00 and 9:00 o'clock set-up to demonstrate simultaneous involuntary activation with iRCT. This sets off the pelvic floor muscles. Thus, normal airway protection data is obtained and normal CNS data to L1 (where spinal cord ends). The set-up includes a complete T12 that cannot void and needs intermittent catheterization with the same set up, thus demonstrating data for normal airway but no L5/S1 EMG activation by MMCC with all the other data necessary to prove an unsafe bladder by the algorithm. A quadriplegic can demonstrate abnormal airway protection and abnormal EMG activation at both paraspinal and pelvic floor muscles with unsafe bladder measurements that follow the algorithm.

It should be understood that iRCT is an involuntary maneuver that activates embryologically predetermined muscles for airway protection and continence that travel primarily through the MMCC in the spinal cord. Different varieties of lesions are captured and determined with summated interval data approach for general screening purposes.

It is known that the laryngeal cough reflex (LCR) is a strong brainstem-mediated reflex that protects the upper airway by preventing aspiration, or the entrance of secretions, food, and/or fluid into the airway below the level of the true vocal cords (rima glottidis), through elicitation of an involuntary cough. The LCR is activated through the stimulation of cough receptors in the vestibule of the larynx. One way this is achieved is through the inhalation of chemostimulants, such as tartaric acid. Studies have shown that if the LCR is intact, the subject will involuntarily cough (normal LCR) upon inhaling a solution containing TA.

In one non-limiting example, the iRCT involves the inhalation of a nebulized 20% normal saline solution of L-TA (Tartaric Acid). Subjects are asked to perform 1 to 3 effective, full inhalations (about 15-20 second exposure by mouth for tidal breathing wearing a nose clip) from a standard jet nebulizer with at least 50 psi from an oxygen wall unit or tank that produces an average droplet diameter of 1 to 2 microns or less. The nebulizer output is 0.58 mL/min. The initiation of an involuntary cough reflex after any one of the inhalations is the end point of the procedure.

Nebulized TA is a chemical tussive that stimulates irritant receptors in the mucosa of the laryngeal aditus. Mild irritation of these receptors results in nerve impulses being conveyed by the internal branch of the superior laryngeal nerve (ibSLN) to bulbar centers of the brainstem. This nerve constitutes the afferent sensory component of the LCR arc. The efferent component of the LCR is mediated through the vagus, phrenic, intercostals and thoracoabdominal nerves.

Inhaled TA is selective in stimulating rapidly adapting ("irritant") receptors (RARs), in the supraglottic region. In humans, bilateral anesthesia of the ibSLN abolishes TA-induced cough and permits tidal breathing of the nebulized vapor without coughing, supporting the idea that the RARs are responsible for TA-induced cough.

The physiological response from inhalation of TA in a normal subject is abrupt, forceful coughing of short duration. Using a 20% solution of inhaled nebulized TA is a safe, reliable way to assess the sensation in the supraglottic laryngeal region and subsequently the neurologic circuitry of the LCR. In addition, the ability of the iRCT to predict the integrity of the protective LCR in subjects with stroke has been studied.

A 20% solution of TA as an aerosol causes cough by stimulating sensory nerves in and under the laryngeal epithelium. These nerves have been identified histologically, and the reflexes they cause have been identified. The sensory nerves can be stimulated by both non-isosmolar and acid solutions. Tartaric acid may act in both ways, but the balance between them is uncertain.

The nerves are stimulated by the opening of membrane channels in the nerve terminals. More than 20 categories of channels have now been identified, the opening of which will allow calcium flow into the nerve (and also sodium, with exit of potassium), with the result that an action potential is set up, which travels to the brainstem in the central nervous system (CNS), and reflexively induces cough.

Several different types of sensory nerve ending in the larynx have been identified that may mediate cough and other defensive reflexes. They have been extensively studied, mainly in experimental animals by recording the action potentials in their nerve fibers. The probable candidates for cough are the RARs or 'irritant' receptors. These are highly sensitive to mechanical stimuli, to hyperosmolar solutions, and to acids.

Once stimulated, the sensory nerves will induce a variety of defensive reflexes, which protect the lungs from invasion of harmful material. These include cough (an inspiration, followed by a forced expiration against a closed glottis, followed by opening of the glottis with an expiratory blast); the laryngeal cough expiratory reflex (LCER, a powerful expiratory effort with the glottis open); and the glottal closure reflex. In some instances a reflex apnea can be produced. The balance of these reflexes may depend on the nature and the strength of the stimulus. In the case of TA, the LCER seems to be dominant, possibly followed by glottal closure, and the pathophysiological advantage of this response in preventing aspiration is obvious.

There now follows an analysis and test results in greater detail that explain the advantageous use of the involuntary reflex cough test (iRCT) for investigating and diagnosing not only SUI, but also physiological abnormalities such as neurologic deficiencies. The nebulizer as described can be used in conjunction with testing. It should be understood that there are differences between normal and neurological patients.

The EMG from the parineal muscles respond almost simultaneously to the onset of the voluntary cough because the patient does not want to leak. With the involuntary reflex cough test, on the other hand, the fast fibers that are set off reach the abdominal muscles quickly, such as in 17 milliseconds as an example. The patient is not able to set their pelvis. In some of the graphs reflecting urodynamic testing as will be described, it is evident that the onset of the EMG activity does not happen at the same time the pressure rises. Some people that have neuropathy, for example, spinal stenosis or nerve injury (even if it is mild), have a situation that prevents the reflexes from closing before the pressure has changed to push on the bladder. It is not possible to obtain this diagnostic tool methodology unless the involuntary cough reflex test is accomplished. When the involuntary reflex cough test is accomplished, it is possible to demonstrate a latency delay and show that the pathophysiology is a neuropathic problem rather than a structural problem. It is possible to separate the pathophysiology using the involuntary reflex cough test and methodology as described.

In one example, a female patient could have a weak spinal cord and her physiology is normal. This patient may not leak during the test, but the patient cannot protect her airway. Thus, using the methodology apparatus and system associated with the involuntary reflex cough test, in accordance with non-limiting examples, it is possible not only to diagnose an unprotected airway, but also to diagnose normal bladder physiology, including the neurophysiology to the patient's sphincter closure process. This is advantageous because it is then possible to determine when someone cannot protect their airway, even though they may have a normal bladder. Conversely, there are patients with a normal airway, but cannot control their bladder. This process and system as described is able to make that diagnosis and thus the involuntary reflex cough test is an advantageous medical diagnostic tool. For example, it is possible to have a patient with a poorly functioning bladder and normal airway and use of the test allows a doctor to find lower urinary tract symptoms and neuropathology. It becomes possible to diagnose a level of lesion in a patient with a full comprehensive neurologic examination using the involuntary reflex cough test, methodology and apparatus as described.

As will be described in detail later, the various components such as the nebulizer, one or more catheters, any pads for the paraspinal muscles when EMG is used, and drug as part of the nebulizer are inserted in a kit for use at the clinic, hospital or setting. Those components can be discarded after use. The handheld device, of course, will be used again. Use of the kit provides a clinician, doctor or other medical professional the readily available diagnostic tool to determine if a patient has a questionable airway and determine bladder physiology at the same time, all with the use of the one kit.

A kit that is marketed for the iRCT diagnostic tool could include the nebulizer and its drug as TA in one example and one or more pads for the electrodes at the paraspinal and use with EMG. The pad may only be necessary for stress incontinence determinations. A catheter is included in another kit example for use in measuring airway and intra-abdominal pressure. In one non-limiting example, a pad can be placed on a catheter to determine urine leakage and aid in determining stress incontinence. Pressure data is sent to the handheld device in some examples. Obtaining any EMG values from the paraspinal in conjunction with the urology analysis is advantageous. It is possible in one example to measure pressure from a bladder catheter and determine at the same time EMG signals using the EMG electrodes at the L5/S1 in conjunction with the measured involuntary reflex cough test and urology catheter sensing. This is advantageous compared to placing electrodes at the perineal muscles on each side of the sphincter.

It has been found that EMG signals obtained from the perineal muscles have EMG activity from the non-involuntary muscles, i.e., the voluntary muscles blacking out and making analysis difficult because of the signal interference. When the electrodes are placed at the back at the L5/S1 junction, on the other hand, there is nothing else but the paraspinal muscles. It is bone below on each side at the L5/S1 junction. The electrical impulses can be obtained that determine the number of cough impulses coming down through the patient. This is accomplished even if a person has much adipose. The electrode pad used at the L5/S1 junction, in one non-limiting example, typically has an active reference and ground. A pad holds this active reference and ground and the leads as the active reference and ground are plugged into the handheld device (or wireless sensing device in another example) and transmit data to the processor. At least one catheter is also plugged into the handheld device (or wireless sensing device) and measures bladder pressures. A rectal catheter can also be used in some examples. The processor receives EMG signals and determines when the cough event is over.

The involuntary coughs are not hidden by interference when measured from the lower back at the paraspinals as described. This allows a clinician to determine coughs from the bladder when the EMG located at the L5/S1. In one aspect, the area under curve and the average pressure is determined for the cough event corresponding to the involuntary reflex cough test. When this involuntary component of the cough ends, in one example, it becomes silent EMG activity for a period of time. The pressures are at baseline for a period of time, which corresponds in one example to an inhalation. The involuntary component is over.

Sometimes with the involuntary reflex cough test, the cough occurs six times without breathing, but when the patient stops to breathe, the event is over. Using the programming applied with the processor in the handheld device, it is possible to calculate the variables inside the wave as to the involuntary cough and determine airway protection capability. Thus, it is possible to determine and measure cough by defining through appropriate data processing the involuntary cough event compared to the whole cough epoch. For example, a patient could cough ten times, but only the first four are part of the involuntary cough event. The coughs after that event are not part of the epoch.

The programming includes algorithm branches resulting in a conclusion of unsafe bladder based on the data analysis. It is possible to calculate from the waveforms information necessary for assessing airway protection ability. It should be understood that taking the EMG from the L5/S1 is also a better situation for the doctor or clinician, and the patient, since it is more acceptable in a hospital, outpatient or inpatient setting. The doctor or clinician does not have to bend down or stoop and look near the crotch area and place pads since the EMG can now be taken from the paraspinals. Also, the placement of pads and electrodes at the paraspinals is advantageous when patients are standing. If pads are placed at the perineal area, sweat and other problems could cause those pads to become loose and good signals may not be obtained. Also, it should be understood that the perineal muscles do not fire involuntarily. The sphincter may fire involuntarily, but that would create more noise as noted before. Electrodes are not placed at the vagina, but are placed at the paraspinal area instead.

This information obtained from iRct and the EMG taken at the paraspinals allows the doctor or clinician to obtain data leading directly to a diagnosis. For example, some patients that have urinary stress incontinence may have a normal airway in this analysis. It has been found by experimentation that the normal airway is about 50 centimeters water average intra-abdominal pressure. It should be understood that the vesicular pressure (bladder pressure) can track intra-abdominal pressure and terms are often similar and used together. "Bladder" or intravesicular pressure is often used to determine and equate with intra-abdominal pressure. The two are sometimes used interchangeably. Stress urinary incontinence and/or bladder physiology can be diagnosed. The system and method as described leads directly to diagnosis. Fifty centimeters average intra-abdominal pressure over time has been found to correspond to an involuntary reflex cough test normal airway. Thus, the standard deviations or other percentages from that value are used in one non-limiting example to determine an abnormal airway. In a conducted study, the actual value is determined to be about 50.6 centimeters water as compared to voluntary cough values of about 48 centimeters of water. In an outpatient setting, it is possible to have the nebulizer (and drug) and only a pad and test SUI. In hospitalized patients or inpatient settings, this combination is used to measure airway and bladder physiology and the test combination includes a catheter.

It should be understood that the involuntary cough reflex test (iRCT) gives a higher pressure average than obtained using a voluntary cough test. The involuntary cough reflex test is thus a valuable medical diagnostic tool. In one example, four variables are significant in this analysis. These variables include: (1) duration of the event; (2) average intra-abdominal pressure of the event; (3) peak intra-abdominal pressure (max) of the event; and (4) area under the curve. Using these four variables, it is possible to process the received data and obtain a specific diagnosis that could not otherwise be obtained without the use of the involuntary reflex cough test. Individual deficits in a specific variable or combination of variables are used to characterize specific diseases and problems and useful as a medical diagnostic tool.

This application is related to copending patent applications entitled, "PULSED NEBULIZER," and "METERED DOSE NEBULIZER," which are filed on the same date and by the same assignee and inventors, the disclosures which are hereby incorporated by reference.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. An atomizer, comprising:
   a atomizer body comprising an air channel section and atomizer outlet;
   an air line extending through the air channel section and having an inlet and an outlet, including a flared extension at the outlet;
   a venturi nozzle at the outlet end of the air line and having a discharge end and oriented horizontally when in use;
   a canister port at the inlet end of the air line that receives a gas canister, and a valve positioned at the canister port and actuable to allow a metered flow of gas at a predetermined pressure and time to flow from the gas canister and through the air line and venturi nozzle;
   a medication receiver carried by the atomizer body proximal to the venturi nozzle and configured to receive and lock in position a medication container, the medication container including knob extensions to lock it into position; and
   a suction line having a proximal and distal end, and the proximal end connected to the discharge end of the venturi nozzle and having a tapered bore and extending from the venturi nozzle to the medication receiver and configured to connect at its distal end into the medication container locked in position at the medication receiver, wherein the proximal end of the suction line includes a diffuser configured with the suction line and venturi nozzle as a mixing chamber, wherein gas that is mixed with medication in the mixing chamber impacts the diffuser to aid in forming a mist, wherein the venturi nozzle, suction line and diffuser are connected as an integral one-piece replaceable unit, wherein the venturi nozzle outputs air in a direction that is normal to the suction line.

2. The atomizer according to claim 1, wherein the valve is actuated to deliver gas when pressure is applied downward on the gas canister.

3. The atomizer according to claim 1, wherein the valve actuates a pulsed and metered flow of gas during atomization.

4. An atomizer, comprising:
- a substantially L-shaped atomizer body forming a vertical portion and a horizontal portion and comprising an air channel section and atomizer outlet;
- an air line extending through the air channel section and having an inlet and outlet, including a flared extension at the outlet;
- a venturi nozzle at the outlet end of the air line within the horizontal portion of the atomizer body and oriented horizontally when in use;
- a canister port at the inlet end of the air line within the vertical portion of the atomizer body that receives a gas canister, and a valve positioned at the canister port and actuable to allow a metered flow of gas at a predetermined pressure and time to flow from the gas canister and through the air line and venturi nozzle;
- a medication receiver carried in the horizontal portion of the atomizer body proximal to the venturi nozzle and configured to receive and lock in position a medication container, the medication container including knob extensions to lock it into position; and
- a suction line having a proximal and distal end, and the proximal end connected to the discharge end of the venturi nozzle and having a tapered bore and extending from the venturi nozzle to the medication receiver and configured to connect at its distal end into the medication container locked in position at the medication receiver, wherein the proximal end of the suction line includes a diffuser configured with the suction line and venturi nozzle as a mixing chamber, wherein gas that is mixed with medication in the mixing chamber impacts the diffuser to aid in forming a mist, wherein the venturi nozzle, suction line and diffuser are connected as an integral one-piece replaceable unit, wherein the venturi nozzle outputs air in a direction that is normal to the suction line.

5. The atomizer according to claim 4, wherein the valve is actuated to deliver gas when pressure is applied downward on the gas canister.

6. The atomizer according to claim 4, wherein the valve actuates a pulsed and metered flow of gas during atomization.

7. An atomizer, comprising:
- a atomizer body comprising an air channel section and atomizer outlet;
- an air line extending through the air channel section and having an inlet and an outlet and including a flared extension at the outlet;
- a venturi nozzle at the outlet end of the air line and having a discharge end and oriented horizontally when in use;
- a canister port at the inlet end of the air line that receives a gas canister, and a valve positioned at the canister port and actuable to allow a metered flow of gas at a predetermined pressure and time to flow from the gas canister and through the air line and venturi nozzle;
- a medication receiver carried by the atomizer body within the air channel section proximal to the venturi nozzle and configured to receive and lock in position a medication container and comprising a cylindrical support including a top support surface having an orifice, the medication container including knob extensions to lock it into position; and
- a suction line having a proximal and distal end, and the proximal end connected to the discharge end of the venturi nozzle and having a tapered bore and extending from the venturi nozzle through the orifice of the top support surface to the medication receiver and configured to connect at its distal end into the medication container locked in position at the medication receiver, wherein the proximal end of the suction line includes a diffuser configured with the suction line and venturi nozzle as a mixing chamber, wherein gas that is mixed with medication in the mixing chamber impacts the diffuser to aid in forming a mist, wherein the venturi nozzle, suction line and diffuser are connected as an integral one-piece replaceable unit, wherein the venturi nozzle outputs air in a direction that is normal to the suction line.

8. The atomizer according to claim 7, wherein said suction line includes a flange that is seated on the top support surface of the medication receiver to support the venturi nozzle, mixing chamber and suction line in position within the atomizer body.

9. The atomizer according to claim 7, wherein the valve is actuated to deliver gas when pressure is applied downward on the gas canister.

10. The atomizer according to claim 7, wherein the valve actuates a pulsed flow of gas during atomization.

* * * * *